United States Patent
Ko et al.

(10) Patent No.: US 8,673,852 B2
(45) Date of Patent: Mar. 18, 2014

(54) METHODS OF TREATING NEURONAL DISORDERS USING MNTF PEPTIDES AND ANALOGS THEREOF

(75) Inventors: Pui-Yuk Dorothy Ko, Monterey Park, CA (US); Mark S. Kindy, Mt. Pleasant, SC (US)

(73) Assignee: Genervon Biopharmaceuticals, LLC, Pasadena, CA (US)

(*) Notice: Subject to any disclaimer, the term of this patent is extended or adjusted under 35 U.S.C. 154(b) by 1139 days.

(21) Appl. No.: 11/939,384

(22) Filed: Nov. 13, 2007

(65) Prior Publication Data
US 2009/0048162 A1    Feb. 19, 2009

Related U.S. Application Data

(60) Provisional application No. 60/858,022, filed on Nov. 10, 2006.

(51) Int. Cl.
*A61K 38/18* (2006.01)
*A61K 38/00* (2006.01)
*A61K 38/16* (2006.01)

(52) U.S. Cl.
USPC ............................................ 514/8.3; 514/1.1

(58) Field of Classification Search
CPC .... C07K 14/475; C07K 14/48; A61K 38/185; A61K 38/00; A61K 38/1703; A61K 8/64
USPC ........ 514/1.1, 8.4, 17.7, 18.9, 8.3, 12.2, 16.5; 530/300, 329, 330; 435/368, 375
See application file for complete search history.

(56) References Cited

FOREIGN PATENT DOCUMENTS

WO    WO 2004065410 A2 *   8/2004

OTHER PUBLICATIONS

Pardridge. CNS drug design based on principles of blood-brain barrier transport. J Neurochem. May 1998;70(5):1781-92.*
Nageswari et al. Therapeutic Efficacy of Basic Fibroblast Growth Factor on Experimental Focal Ischemia Studied by Magnetic Resonance Imaging. J Stroke Cerebrovasc Dis. Sep.-Oct. 2005;14(5):187-92.*
Broadwell et al. Serum proteins bypass the blood-brain fluid barriers for extracellular entry to the central nervous system. Exp Neurol. Apr. 1993;120(2):245-63.*
Greenburg et al. From angiogenesis to neuropathology. Nature. Dec. 15, 2005;438(7070):954-9.*

* cited by examiner

*Primary Examiner* — Gregory S Emch

(57) ABSTRACT

The present disclosure relates to methods for treating neuronal disorders using a motoneuronotrophic factor (MNTF) or its peptide analogs. The present disclosure further relates to methods for treating a spinal cord injury, a neurodegenerative disease, a stroke or cerebral ischemia, Huntington's Disease, Parkinson's Disease, Multiple Sclerosis, amyotrophic lateral sclerosis (ALS), Alzheimer's Disease, and diabetic neuropathy in a subject by administration of motoneuronotrophic factor (MNTF) or its peptide analogs.

21 Claims, 50 Drawing Sheets

Figure 6
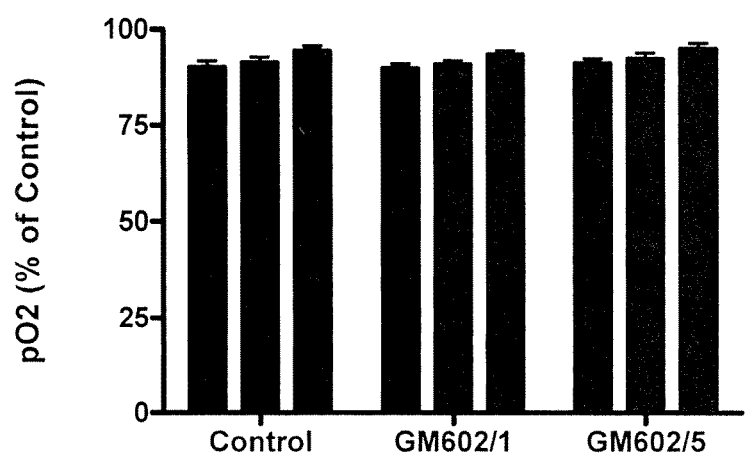
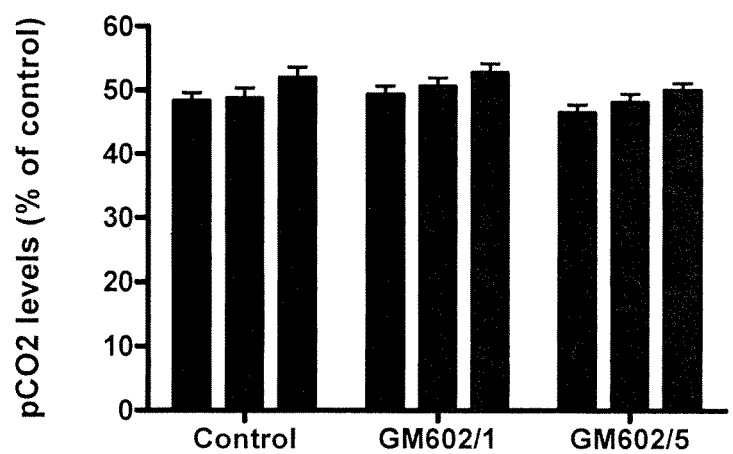

| | 26 | 27 | 28 | 29 | 30 | 31 | 4 | 32 | 33 | 34 | 35 | 36 | 37 | 38 | 39 | 40 | 41 | 42 | 43 | 44 | 5 |
|---|---|---|---|---|---|---|---|---|---|---|---|---|---|---|---|---|---|---|---|---|---|
| | | | | | | | | | | | | | | | | | | | | | |
| | | | | | | | | | | | | | | | | | | | | | G |
| | | | | | | | | | | | E | | | | | | | | | E | |
| | A | A | | | | | | | | A | A | | | | | | A | A | A | |
| | L | L | | | | | L | | | L | L | | | | | | L | L | L | |
| | C | C | | | | C | C | C | C | C | | | | | C | C | C | C | C | |
| | R | R | | | R | R | R | R | R | R | | | | R | R | R | R | R | R | |
| | A | A | | A | A | A | A | A | A | A | | A | A | A | A | A | A | A | A | |
| | Y | Y | | Y | Y | Y | Y | Y | Y | Y | | Y | Y | Y | Y | Y | Y | Y | Y | |
| | R | R | R | R | R | R | R | R | R | R | | R | R | R | R | R | R | R | R | |
| | S | S | S | S | S | S | S | S | S | S | S | S | S | S | S | S | S | S | S | S |
| | F | F | F | F | F | F | F | F | F | F | F | F | F | F | F | F | F | F | F | F |
| | A | A | A | A | A | A | A | A | A | A | | A | A | A | A | A | A | A | A | A |
| | | S | S | S | S | S | | S | S | S | | S | S | S | S | S | | S | S | S |
| | | L | L | L | L | | | L | L | L | | L | L | L | L | | | L | L | L |
| | | M | M | M | M | | | M | M | M | | M | M | M | M | M | | | | M |
| | | W | W | W | W | | | W | W | W | | W | W | W | W | | | | | |
| | | C | C | C | | | | C | C | C | | C | | | | | | | | |
| | | N | N | N | | | | N | N | | | N | | | | | | | | |
| | | L | L | | | | | L | L | | | L | | | | | | | | |
| | | | | | | | | T | | | | | | | | | | | | |

| Pos | T | F | W | G | D | T | L | N | C | W | M | L | S | A | F | S | R | Y | A | R | C | L | A | E | G | H | D | G | P |
|---|---|---|---|---|---|---|---|---|---|---|---|---|---|---|---|---|---|---|---|---|---|---|---|---|---|---|---|---|---|
| 86 | | | | | | | L | N | C | W | M | L | S | A | F | S | R | Y | A | R | C | | | | | | | | |
| 87 | | | | | | | | N | C | W | M | L | S | A | F | S | R | Y | A | R | C | L | A | E | | | | | |
| 88 | | | | | | | | | C | W | M | L | S | A | F | S | R | Y | A | R | C | L | A | E | G | | | | |
| 89 | | | | | | | | | | W | M | L | S | A | F | S | R | Y | A | R | C | L | A | E | G | H | | | |
| 90 | | | | | | | | | | | M | L | S | A | F | S | R | Y | A | R | C | L | A | E | G | H | D | | |
| 91 | | | | | | | | | | | | L | S | A | F | S | R | Y | A | R | C | L | A | E | G | H | D | G | |
| 92 | | | | | | | | | | | | | S | A | F | S | R | Y | A | R | C | L | A | E | G | H | D | G | P |
| 93 | | | | | | | | | | | | | | A | F | S | R | Y | A | R | C | L | A | E | G | H | D | G | |
| 94 | | | | | | | | | | | | | | | F | S | R | Y | A | R | C | L | A | E | | | | | |
| 95 | | | | | | | | | | | | | | | | | | | | | | | | | | | | | |
| 96 | | | | | | | | | | | | | | | | S | R | | A | R | | | | | | | | | |
| 97 | | | | | | | | | | | | | S | A | F | S | R | Y | A | | | | | | | | | | |
| 98 | | | | | | | L | N | C | W | M | L | S | A | F | S | R | Y | A | R | C | L | A | E | | | | | |
| 99 | | | | | | T | L | N | C | W | M | L | S | A | F | S | R | Y | A | R | C | L | A | E | G | | | | |
| 100 | | | | | D | T | L | N | C | W | M | L | S | A | F | S | R | Y | A | R | C | L | A | E | G | | | | |
| 101 | | | | G | D | T | L | N | C | W | M | L | S | A | F | S | R | Y | A | R | C | L | A | E | G | | | | |
| 102 | | | W | G | D | T | L | N | C | W | M | L | S | A | F | S | R | Y | A | R | C | L | A | E | G | | | | |
| 103 | | | | G | D | T | L | N | C | W | M | L | S | A | F | S | R | Y | A | R | C | L | A | E | G | | | | |
| 104 | | | W | | D | | L | N | C | W | M | L | S | A | F | S | R | Y | A | R | C | L | A | E | G | H | | | |
| 105 | | | | | | | | | | | W | M | L | S | A | F | S | R | Y | A | R | C | L | A | E | G | | | |
| 106 | | | | | | | L | | | | | L | S | A | F | S | R | Y | A | R | C | L | A | E | G | H | D | | |

| | 107 | 108 | 109 | 110 | 111 | 112 | 113 | 114 | 115 | 116 | 117 | 118 | 119 | 120 | 121 | 122 | 123 | 124 | 125 | 126 | 127 |
|---|---|---|---|---|---|---|---|---|---|---|---|---|---|---|---|---|---|---|---|---|---|
| G D T L N C W M L | S | A | F | S | R | Y | A | R | C | L | A | E | G | H | D | G | | | | | | |
| T F W G D T L N C W M L | S | A | F | S | R | Y | A | R | | L | A | E | G | H | D | G | P | | | | | |
| T F W G D T L N C W M L | S | A | F | S | R | Y | A | R | | L | A | E | G | H | D | G | P | T | | | | |
| F W G D T L N C W M L | S | A | F | S | R | Y | A | R | | | | | | | | | | | | | |
| W G D T L N C W M L | S | A | F | S | R | Y | A | R | | | | | | | | | | | | | |
| D T L N C W M L | S | A | F | S | R | Y | A | R | C | L | A | E | | | | | | | | | |
| D T L N C W M L | S | A | F | S | R | Y | A | R | C | L | A | E | G | H | | | | | | | |
| D T L N C W M L | S | A | F | S | R | Y | A | R | C | L | A | E | G | H | D | | | | | | |
| D T L N C W M L | S | A | F | S | R | Y | A | R | C | L | A | E | G | H | D | | | | | | |
| D T L N C M L | S | A | F | S | R | Y | A | R | C | L | A | E | G | H | D | | | | | | |
| T L N C W M | | | A | F | S | R | Y | A | R | C | L | A | E | G | H | D | G | | | | |
| L N C W M L | S | A | F | S | R | Y | A | R | C | L | A | E | G | H | D | G | | | | | |
| N C W | | | | | F | S | R | Y | A | R | C | L | A | E | G | H | D | G | P | | |
| | | | | | | | | | Y | A | R | C | L | A | E | G | H | D | G | P | T | |
| | | | | | | | | | Y | A | R | C | L | A | E | G | H | D | G | P | T | Q |
| D T L N C W M L | S | A | F | S | R | Y | A | R | C | L | A | E | G | H | D | G | | | | | |
| G T F W G D T L N C W M L | S | A | F | S | R | Y | A | R | C | L | A | E | G | H | D | G | P | T | | | |
| L G T F W G D T L N C W M L | S | A | F | S | R | Y | A | R | C | L | A | E | G | H | D | G | P | T | | | |

| | | | | | | | | | | | | | | | | | | | | | | | | | 128 | 129 | 130 | 131 | 132 | 133 | 134 | 135 | 136 | 137 | 138 | 139 | 140 | 141 | 142 | 7 | 1 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | Q | Q | Q | Q |
| | | | | | | | | | | | | | | | | | | | | | | | | | | | | | | | | | | | T | T | T | T | | |
| | | | | | | | | | | | | | | | | | | | | | | | | | | | | | | | | | P | P | P | P | | | |
| | | | | | | | | | | | | | | | | | | | | | | | | | | | | | | | G | G | G | G | G | G | | | |
| | | | | | | | | | | | | | | | | | | | | | | | | | | | | | | D | D | D | D | D | D | | | | |
| | | | | | | | | | | | | | | | | | | | | | | | | | | | | | H | H | H | H | H | H | H | | | | | |
| | | | | | | | | | | | | | | | | | | | | | | | | | | | G | G | G | G | G | G | G | | | | | | |
| | | | | | | | | | | | | | | | | | | | | | | | | | | E | E | F | E | E | E | E | E | | | | | | | |
| | | | | | | | | | | | | | | | | | | | | | | | | A | A | A | A | A | A | A | A | A | | | | | | | | |
| | | | | | | | | | | | | | | | | | | | | | | | L | L | L | L | L | L | L | L | L | | | | | | | | | |
| | | | | | | | | | | | | | | | | | | | | | | C | C | C | C | C | C | C | C | C | C | | | | | | | | | |
| | | | | | | | | | | | | | | | | | | | | | R | R | R | R | R | R | R | R | R | R | R | | | | | | | | | |
| | | | | | | | | | | | | | | | | | | | | A | A | A | A | A | A | A | A | A | A | A | A | | | | | | | | | |
| | | | | | | | | | | | | | | | | | | | Y | Y | Y | Y | Y | Y | Y | Y | Y | Y | Y | Y | Y | | | | | | | | | |
| | | | | | | | | | | | | | | | | | | R | R | R | R | R | R | R | R | R | R | R | R | R | R | | | | | | | | | |
| | | | | | | | | | | | | | | | | | S | S | S | S | S | S | S | S | S | S | S | S | S | S | S | | | | | | | | | |
| | | | | | | | | | | | | | | | | F | F | F | F | F | F | F | F | F | F | F | F | F | | F | F | | | | | | | | |
| | | | | | | | | | | | | | | | A | A | A | A | A | A | A | A | A | A | A | | A | | A | A | | | | | | | | |
| | | | | | | | | | | | | | | S | S | S | S | S | S | S | S | S | S | S | S | | | S | S | | | | | | | | |
| | | | | | | | | | | | | | L | L | L | L | L | L | L | L | L | | L | | | | L | L | | | | | | | | |
| | | | | | | | | | | | | M | M | M | M | M | M | M | M | M | M | | | | | M | M | | | | | | | | |
| | | | | | | | | | | | W | W | W | W | W | W | W | W | W | W | | | | | | | | | | | | | | |
| | | | | | | | | | | C | C | C | C | C | C | C | C | | N | | | | | | | | | | | | | | | |
| | | | | | | | | | N | N | N | N | N | N | N | L | | | | | | | | | | | | | | | | | | |
| | | | | | | | | L | L | L | L | L | L | T | | | | | | | | | | | | | | | | | | | | |
| | | | | | | | T | T | T | T | T | D | | | | | | | | | | | | | | | | | | | | | | |
| | | | | | | D | D | D | D | D | G | | | | | | | | | | | | | | | | | | | | | | | |
| | | | | | G | G | G | G | G | W | | | | | | | | | | | | | | | | | | | | | | | | |
| | | | | W | W | W | W | W | F | | | | | | | | | | | | | | | | | | | | | | | | | |
| | | | F | F | F | F | F | | | | | | | | | | | | | | | | | | | | | | | | | | | |
| | | T | T | T | T | T | | | | | | | | | | | | | | | | | | | | | | | | | | | | |
| | L | | | | | | | | | | | | | | | | | | | | | | | | | | | | | | | | | |
| L | G | T | F | W | G | D | T | L | N | C | W | M | L | S | A | F | S | R | Y | A | R | C | L | A | E | G | H | D | G | P | T | Q | | |

Fig. 25G p < 0.001 for 0, 3, 6, 12 hr groups compared to vehicle group.
p = NS for 24 hr group to vehicle group.

p = NS for all samples compared to vehicle.

p = NS for all samples compared to vehicle.

p = NS for all samples compared to vehicle.

p = NS for all samples compared to vehicle.

p = NS for all samples compared to vehicle.

p < 0.001 for 0, 3, 6 hr groups compared to vehicle group.
p < 0.002 for 12 hr group compared to vehicle group.
p = NS for 24 hr group to vehicle group.

p <0.0045 for 2.5 mg/kg group compared to vehicle group.
p < 0.0001 for 10 and 20 mg/kg groups compared to vehicle group p < 0.0001 for CBF of all post-ischemia groups compared to pre-ischemia groups.

p < NS for CBF of post ischemia vehicle groups before vs after saline administration.

p < 0.0001 for CBF of each post permanent ischemic GM602 groups before vs after GM602 administration.

p = NS for all groups compared to vehicle.

p = NS for all groups compared to vehicle.

p = NS for all groups compared to vehicle.

FIGURE 39A. Forelimb Placement
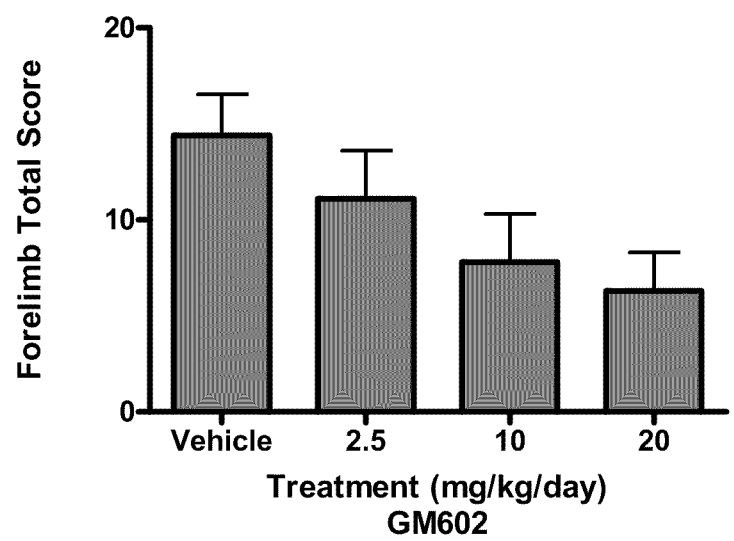

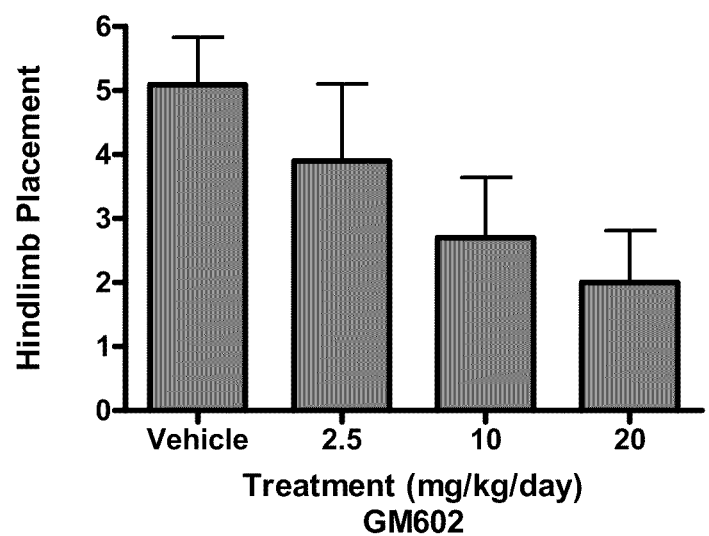
Figure 39B. Hindlimb Placement

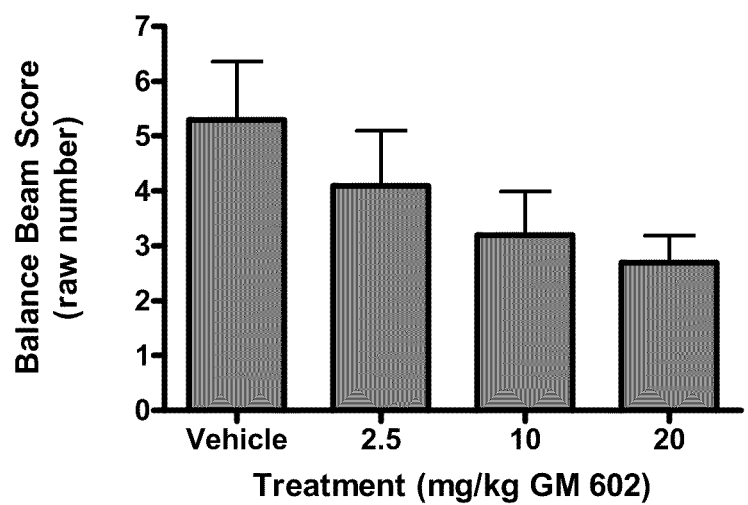
Figure39C. Balance Beam

Figure 39D. Spontaneous Locomotion
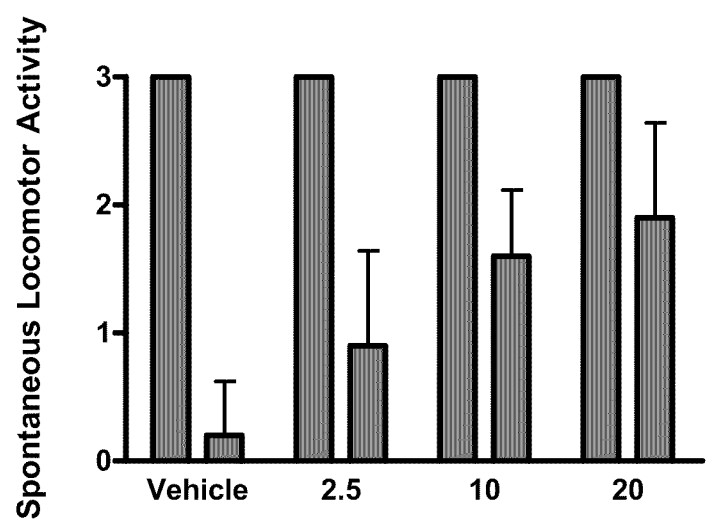

p < 0.005 for group treated with 2.5 mg/kg GM602 compared to vehicle treated group
p < 0.0001 for groups treated with 10 and 20 mg/kg GM602 compared to vehicle treated group.

p = 0.0007 for group treated with 2.5 mg/kg GM602 compared to vehicle treated group
p < 0.0001 for groups treated with 10 and 20 mg/kg GM602 compared to vehicle treated group.

METHODS OF TREATING NEURONAL DISORDERS USING MNTF PEPTIDES AND ANALOGS THEREOF

CROSS-REFERENCES TO RELATED APPLICATIONS

This application is entitled to priority pursuant to 35 U.S.C. §119(e) to U.S. provisional patent application 60/858,022, which was filed on 10 Nov. 2006.

BACKGROUND OF THE DISCLOSURE

The present disclosure relates generally to compositions and methods for treating neuronal disorders using MNTF peptides and analogs thereof.

The following includes information that may be useful in understanding the present disclosure. It is not an admission that any of the information provided herein is prior art, or relevant, to the presently disclosure, or that any publication or document that is specifically or implicitly referenced is prior art.

The survival of embryonic motoneurons has been found to be dependent upon specific trophic substances derived from the associated developing skeletal muscles. Certain skeletal muscles have been reported to produce substances which are capable of enhancing the survival and development of motoneurons by preventing the embryonic motoneurons from degeneration and subsequent, natural cellular death. These substances have been broadly described as neuronotrophic factors (NTFs), which are a specialized group of proteins which function to promote the survival, growth, maintenance, and functional capabilities of selected populations of neurons (e.g. Chau, R. M. W., et al., 6 Chin. J Neuroanatomy 129, 1990).

A variety of neurodegenerative, neuromuscular and neuronal diseases, disorders, or conditions affecting the central and/or peripheral nervous systems may be characterized in whole or in part by acute or progressive loss of functional neural tissues. These include conditions such as, for example, spinal cord injury (SCI), neurodegenerative disease, stroke or ischemia (e.g. cerebral ischemia), Huntington's Disease (HD), Parkinson's Disease (PD), Multiple Sclerosis (MS), amyotrophic lateral sclerosis (ALS), Alzheimer's Disease (AD), and diabetic neuropathy.

U.S. Pat. No. 6,309,877, U.S. Pat. No. 7,183,373, U.S. Pat. No. 6,841,531, U.S. Pat. No. 6,759,389 and US20060052299 report specific neuronotrophic factors (NTFs) termed Motoneuronotrophic Factors (MNTF) which possesses the ability to exert trophic effects on motoneurons. The contents of which are hereby incorporated by reference in their entirety.

BRIEF SUMMARY

Described herein is technology having many attributes and embodiments including, but not limited to, those set forth or described or referenced in this Brief Summary. It is not intended to be all-inclusive and the claims are not limited to or by the features or embodiments identified in this Brief Summary, which is included for purposes of illustration only and not restriction.

Accordingly, in one aspect, the present disclosure is directed to novel peptides and compositions containing portions of the MNTF-molecule that are useful for modulating the viability and proliferation of neuronal cells, thereby providing for neurotrophic peptides that can be readily synthesized and therapeutically efficacious in treating a wide range of neurodegenerative, neuromuscular diseases, disorders, or conditions in the central and/or peripheral nervous systems.

In one aspect, a method of treating motor neuron defects and/or neuronal disorder in a subject comprising administering a motoneuronotropic factor (MNTF) analog to the subject in need thereof, wherein said neuronal disorder is selected from a spinal cord injury, a neurodegenerative disease, a stroke or cerebral ischemia, Huntington's disease, Parkinson's disease, Multiple Sclerosis, ALS, Alzheimer's disease, and a diabetic neuropathy, wherein said motoneuronotropic factor (MNTF) analog is administered in an amount sufficient to treat said neuronal disorder, is provided.

In one aspect, the present disclosure is directed to synthetic and/or purified MNTF peptide analogs comprising a portion of the WMLSAFSRYAR domains (including WMLSAFS, FSRYAR, and other domains from SEQ ID NOs: 1-142) and to molecules that mimic its structure and/or function thereof, including truncated sequence homologs and analogs, useful for inducing or modulating the viability and growth of a neuronal cell.

In certain embodiments, MNTF peptide analogs may include sequence analogs comprising SEQ ID NOs: 1-7 as well as SEQ ID NOs: 8-142 (see FIG. 25).

```
LGTFWGDTLN CWMLSAFSRY ARCLAEGHDG PTQ   (SEQ ID NO: 1)

FSRYAR                                 (SEQ ID NO: 2)

WMLSAFS                                (SEQ ID NO: 3)

MLSAFSRYAR                             (SEQ ID NO: 4)

FSRYARCLAE G                           (SEQ ID NO: 5)

CWMLSAFSRY ARC                         (SEQ ID NO: 6)

MLSAFSRYAR CLAEGHDGPT Q                (SEQ ID NO: 7)
```

MNTF peptide analogs described herein polypeptides derived from MNTF (i.e., from SEQ ID NO: 1) and analogs of such derivative polypeptides. These compounds include polypeptides having the amino acid sequence of one of SEQ ID NOs: 1-142, such as any of SEQ ID NOs: 2-7. include functional derivatives of the MNTF peptide analogs as described in SEQ ID NOs: 1-7. Salts, esters, and other ordinary dosage forms of such polypeptides are useful in the technology described herein, as are polypeptides in which one or more of the amino acid residues has been replaced by a non-naturally-occurring (e.g., D-isomer) amino acid residue. Other analogs (including amino acid residues that are conservative replacements for those disclosed in SEQ ID NO: 1) can be used in place of one or more of these residues, as described herein.

In another aspect, compositions and methods for modulating the viability and/or growth of a neuronal cells by administering the MNTF peptide analogs in vitro to cell cultures or in vivo to an individual suffering from a nerve injury or neurodegenerative disorder, in order to promote cell proliferation or stabilize inappropriate cell death, and/or in either case to restore normal cell behavior.

In one aspect, there is provided a method of repairing damaged neural pathway in a subject comprising administering a motoneuronotropic factor (MNTF) analog to the subject in need thereof, wherein said damaged neural pathway is associated with a spinal cord injury, a neurodegenerative disease, a stroke or cerebral ischemia, Huntington's disease, Parkinson's disease, Multiple Sclerosis, ALS, Alzheimer's, and a Diabetic Neuropathy, wherein said motoneuronotropic factor (MNTF) analog is administered in an amount sufficient to treat said neuronal disorder whereby the damaged neural pathway in said subject is repaired.

In one aspect, there is provided a method of improving motor function in a subject with symptoms of neural pathway damage comprising administering a motoneuronotropic factor (MNTF) analog to the subject in need thereof, wherein said damaged neural pathway is associated with a spinal cord injury, a neurodegenerative disease, a stroke or cerebral ischemia, Huntington's disease, Parkinson's disease, Multiple Sclerosis, ALS, Alzheimer's, and a Diabetic Neuropathy, wherein said motoneuronotropic factor (MNTF) analog is administered in an amount sufficient to treat said damaged neural pathway in said subject whereby motor function is improved.

DESCRIPTION OF THE FIGURES

FIG. 6. Blood gas measurement in mice subject to ischemia/reperfusion injury. All mice were subjected to 1 hour of cerebral ischemia followed by 24 hours of reperfusion. Animals were injected with vehicle (control) or GM602 at 1 mg/kg or 5 mg/kg intravenously at the end of ischemia. For each study group, blood gases (pO2 and pCO2) were measured before ischemia (first column), during ischemia (second column) and after injection of test article (third column).

FIG. 25, consisting of FIGS. 25A, 25B, 25C, 25D, 25E, 25F, and 25G, is a partial listing of exemplary MNTF peptide analogs. Sequences corresponding to respective SEQ ID NOs are highlighted.

FIG. 39. Neurological deficit measurements in rats subject to ischemia injury. All rats were subjected to permanent cerebral ischemia followed by 28 days of recovery. At 3 hours after ischemia onset, animals were injected with vehicle (control), GM602 at 2.5, 10 or 20 mg/kg intravenously. FIG. 39A. Forelimb placement. FIG. 39 B. Hindlimb placement. FIG. 39 C. Balance beam. FIG. 39 D. Neurological deficits (spontaneous locomotor activity) were measured at the end of the study. In FIG. 39 D, first bar is score prior to test article administration and second bar is score at 28 days after test article administration.

DETAILED DESCRIPTION

Figure 1:
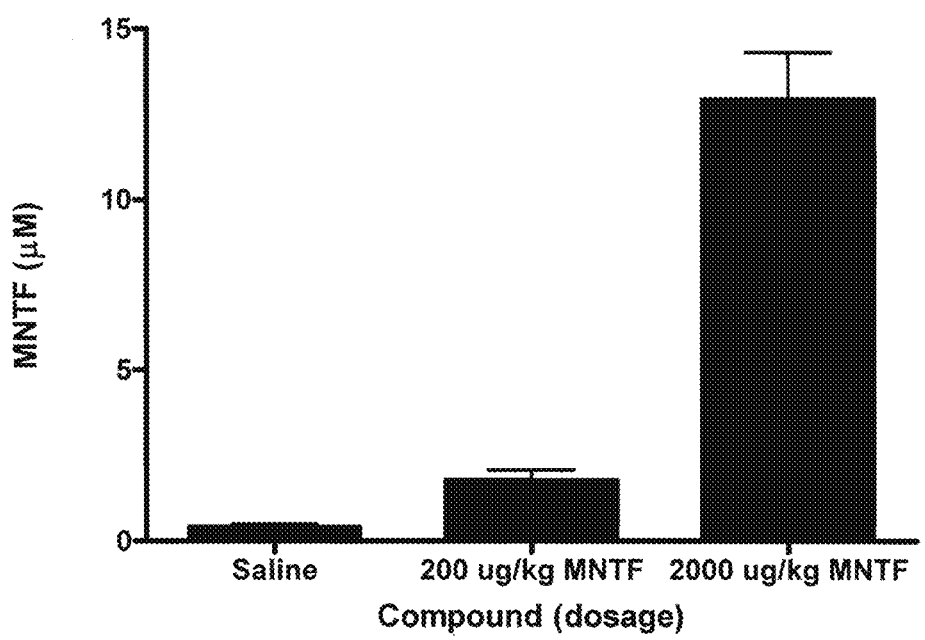
FIG. 1. Illustrates levels of an exemplary MNTF 6-mer peptide analog (GM6; FSRYAR, SEQ ID NO: 2) in the brain of wild type mice. Wild type mice: vehicle control (Saline), MNTF at 0.2 mg or MNTF at 2 mg/kg. The indicated test articles were administered at time 0 and the brains were collected 4 hours later for analysis by ELISA.

The survival of embryonic motoneurons has been found to be dependent upon specific trophic substances derived from the associated developing skeletal muscles. Skeletal muscles have been reported to produce substances which are capable of enhancing the survival and development of motoneurons by preventing the embryonic motoneurons from degeneration and subsequent, natural cellular death. (O'Brian, R. J. and Fischbach, G. D., 6 J. Neurosci. 3265 (1986); Hollyday, M. and Hamburger, V., 170 J. Comp. Neurol. 311 (1976). McManaman, J. L., et al., 263 J. Biol. Chem. 5890 (1988); Oppenheim, R. W., et al., 240 Science, 919 (1988); and Smith, R. G., et al., 6 J. Neurosci. 439 (1986).

Human Motoneuronotrophic Factor (MNTF) is a specific NTF derived from skeletal muscle tissue that has been shown to reduce inflammation at the site of motoneuron injury, enhance nerve regeneration, and promote the survival of motoneurons. MNTF has been tested in various rat nerve systems, including the peripheral sciatic nerve (controlling lower limb muscles), the peripheral musculocutaneous nerve (controlling upper limb muscles), the cranial facial nerve (controlling facial and head muscles), the cranial hypoglossal nerve (controlling the tongue), and the portion of the spinal cord that controls muscles in the neck, chest and upper limbs. In the spinal cord model, MNTF was applied on the nerve graft in a hemi-section spinal cord in rat; MNTF reduced inflammation, limited degeneration and enhanced regeneration of the grafted nerves. A number of studies have demonstrated the efficacy of the synthesized MNTF or peptide analogs thereof in rat peripheral nerve model systems for trophic and tropic effects when MNTF or peptide analog thereof is applied directly on the nerve. In addition, MNTF has been shown to promote the regeneration and survival of motoneurons.

Neuronal cell death occurs in the nervous systems of vertebrates during certain periods of growth and development. Thus, addition of soluble neuronal trophic factors from associated target tissues can serve to mitigate this phenomenon of neuronal death.

Accordingly, aspects and embodiments of the present disclosure provide methods and compositions comprising MNTF peptide analogs and derivatives thereof for the treatment of neuronal disorders.

Aspects and embodiments of the disclosure are directed to a functional protein domains associated with the actions of motoneuronotrophic factors, which has been identified and mapped to short overlapping subsequences in the MNTF1 molecule. These protein domains, which include the "WMLSAFSRYAR," "WMLSAFS," "FSRYAR," and other domains from SEQ ID NOs: 1-142, are sufficient to modulate the viability and proliferation of neuronal cells. Moreover, truncated MNTF1 species encompassing these domains or analogs (sequence fragment analogs or functional analogs thereof) are themselves sufficient to demonstrate stimulatory bioactivity in motoneuron/neuroblastoma cell hybrids.

DEFINITIONS

Certain terms used in the context of the describing the technology to which this disclosure pertains are set forth. Unless indicated otherwise, the following terms have the following meanings when used herein and in the appended claims. Those terms that are not defined below or elsewhere in the specification shall have their art-recognized meaning.

As used herein, a "motoneuronotrophic factor or motoneuron trophic factor" includes those factors involved in the nutrition or maintenance of motor neurons. The terms "motoneuronotropic factor", "MNTF", "MNTF peptide", "motoneuronotropic factor analog", and "MNTF analog" may be used interchangeably as long as they have the functional properties defined herein. These may include sequence and functional homologs of the reference MNTF sequence. Motoneuronotrophic factors, may further the development and differentiation of committed neural progenitor cells, or they may induce or enhance the growth (e.g. neurite outgrowth) and survival of differentiated neural cells. The motoneuronotrophic factors of the present disclosure are typically provided in amounts effective to produce a fully-differentiated neural cell of the CNS or PNS (e.g., a motor neuron). Guidance for the amount is provided herein, and may be readily determined by the skilled artisan based upon known procedures and methods disclosed herein.

Exemplary MNTF peptides and peptide analogs thereof may include those reported in Chau, R. M. W., et al., Muscle Neuronotrophic Factors Specific for Anterior Horn Motoneurons of Rat Spinal Cord. In: Recent Advances in Cellular and Molecular Biology, Vol. 5, Peeters Press, Leuven, Belgium, pp. 89-94 (1992), as well as those found in for example, U.S. Pat. No. 6,309,877, U.S. Pat. No. 7,183,373, U.S. Pat. No. 6,841,531, U.S. Pat. No. 6,759,389 and US20060052299. The contents of which are hereby incorporated in their entirety. In certain embodiments, exemplars may include synthetic and/or purified MNTF peptide analogs comprising a portion of the WMLSAFSRYAR domains (including WMLSAFS, FSRYAR, and other domains from SEQ ID NOs: 1-142) and to molecules that mimic its structure and/or function thereof, including truncated sequence homologs and analogs, useful for inducing or modulating the viability and growth of a neuronal cell.

In addition, exemplary MNTF peptides and peptide analogs thereof may also include those described in Chau, R. M. W., et al., The Effect of a 30 kD Protein from Tectal Extract of Rat on Cultured Retinal Neurons, 34 Science in China, Series B, 908 (1991); Chau, R. M. W., et al., Muscle Neuronotrophic Factors Specific for Anterior Horn Motoneurons of Rat Spinal Cord. In: Recent Advances in Cellular and Molecular Biology, Vol. 5, Peeters Press, Leuven, Belgium, pp. 89-94 (1992); Chau, R. M. W., et al., The Effect of a 30 kD Protein from Tectal Extract of Rat on Cultured Retinal Neurons, 34 Science in China, Series B, 908 (1991); Chau, R. M. W., et al., Cloning of Genes for Muscle-Derived Motoneuronotrophic Factor 1 (MNTF1) and Its Receptor by Monoclonal Antibody Probes, (abstract) 19 Soc. for Neurosci. part 1, 252 (1993), Chau, R. M. W., et al., Cloning of Genes for Muscle-Derived Motoneuronotrophic Factor 1 (MNTF1) and Its Receptor by Monoclonal Antibody Probes, (abstract) 19 Soc. for Neurosci. part 1, 252 (1993), the entire contents of which is hereby incorporated by reference. In certain embodiments, the MNTF or analogs thereof is synthetic or purified.

In certain embodiments, MNTF peptide analogs may include sequences from one of the active sites of the MNTF domain (e.g. an MNTF analog of six amino acids, such as SEQ ID NO: 2).

In certain embodiments, MNTF peptide analogs may include sequence analogs comprising SEQ ID NOs: 1-142.

In certain embodiments, the MNTF peptide analogs may include functional derivatives of the peptide analogs as described in SEQ ID NOs: 1-142.

In certain other embodiments, the MNTF peptide analogs and derivatives may consist of sequences as described in SEQ ID NOs: 1-142.

"Analogs," as used in the present application, means those peptides, in which one or more of the amino acids in the referenced sequences are changed without substantially affecting the MNTF activity. In certain embodiments, analogs in accordance with the present disclosure include "conservative" substitutions. Conservative amino acid substitutions include amino acids replacements with synonymous amino acids within the same group, which have sufficiently similar physicochemical properties that substitution between members of the group will preserve the biological function of the molecule, Grantham, Science, Vol. 185, pp. 862-864 (1974).

The synonymous amino acid groups include those defined in Tables I, II, and III.

TABLE I

Broader Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |

TABLE I-continued

Broader Groups of Synonymous Amino Acids

| Amino Acid | Synonymous Group |
|---|---|
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

Intermediate Groups of Synonymous Amino Acids

| Amino Acid | Synonymous Group |
|---|---|
| Ser | Ser |
| Arg | His, Lys, Arg |
| Leu | Ile, Phe, Met, Leu |
| Pro | Ala, Pro |
| Thr | Thr |
| Ala | Pro, Ala |
| Val | Met, Ile, Val |
| Gly | Gly** |
| Ile | Ile, Met, Phe, Val, Leu |
| Phe | Met, Tyr, Ile, Leu, Phe |
| Tyr | Phe, Tyr |
| Cys | Ser, Cys |
| His | Arg, Gln, His |
| Gln | Glu, His, Gln |
| Asn | Asp, Asn |
| Lys | Arg, Lys |
| Asp | Asn, Asp |
| Glu | Gln, Glu |
| Met | Phe, Ile, Val, Leu, Met |
| Trp | Trp |

TABLE III

Narrower Groups of Synonymous Amino Acids

| Amino Acid | Synonymous Group |
|---|---|
| Ser | Ser |
| Arg | Arg |
| Leu | Ile, Met, Leu |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Ser, Cys |
| His | His |
| Gln | Gln |
| Asn | Asn |
| Lys | Lys |
| Asp | Asp |
| Glu | Glu |
| Met | Ile, Leu, Met |
| Trp | Trp |

Amino acids used in compounds provided herein (e.g., peptides and proteins) can be genetically encoded amino acids, naturally occurring non-genetically encoded amino acids, or synthetic amino acids. Both L- and D-enantiomers of any of the above can be utilized in the compounds. The following abbreviations may be used herein for the following genetically encoded amino acids (and residues thereof): alanine (Ala, A); arginine (Arg, R); asparagine (Asn, N); aspartic acid (Asp, D); cysteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V).

Certain commonly encountered amino acids that are not genetically encoded and that can be present in the compounds described herein include, but are not limited to, β-alanine (b-Ala) and other omega-amino acids such as 3-aminopropionic acid (Dap), 2,3-diaminopropionic acid (Dpr, Z), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle, J); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys); 3-benzothiazol-2-yl-alanine (BztAla, B); and homoserine (hSer). Additional amino acid analogs contemplated include phosphoserine, phosphothreonine, phosphotyrosine, hydroxyproline, gamma-carboxyglutamate, hippuric acid, octahydroindole-2-carboxylic acid, statine, α-methyl-alanine, para-benzoyl-phenylalanine, propargylglycine, and sarcosine. Peptides described herein can have any of the foregoing amino acids in the L- or D-configuration, or any other amino acid described herein or known in the art, whether currently or in the future.

Amino acids that are substitutable for each other generally reside within similar classes or subclasses. As known to one of skill in the art, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. Polar amino acids include amino acids having acidic, basic or hydrophilic side chains and nonpolar amino acids include amino acids having aromatic or hydrophobic side chains. Nonpolar amino acids may be further subdivided to include, among others, aliphatic amino acids. The definitions of the classes of amino acids as used herein are as follows:

"Nonpolar Amino Acid" refers to an amino acid having a side chain that is uncharged at physiological pH, that is not polar and that is generally repelled by aqueous solution. Examples of genetically encoded hydrophobic amino acids include Ala, Ile, Leu, Met, Trp, Tyr and Val. Examples of non-genetically encoded nonpolar amino acids include t-BuA, Cha and Nle.

"Aromatic Amino Acid" refers to a nonpolar amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 3-benzothiazol-2-yl-alanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic Amino Acid" refers to a nonpolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Polar Amino Acid" refers to a hydrophilic amino acid having a side chain that is charged or uncharged at physiological pH and that has a bond in which the pair of electrons shared in common by two atoms is held more closely by one of the atoms. Polar amino acids are generally hydrophilic, meaning that they have an amino acid having a side chain that is attracted by aqueous solution. Examples of genetically encoded polar amino acids include asparagine, cysteine, glutamine, lysine and serine. Examples of non-genetically encoded polar amino acids include citrulline, homocysteine, N-acetyl lysine and methionine sulfoxide.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include ornithine, 2,3-diaminopropionic acid, 2,4-diaminobutyric acid and homoarginine.

"Ionizable Amino Acid" refers to an amino acid that can be charged at a physiological pH. Such ionizable amino acids include acidic and basic amino acids, for example, D-aspartic acid, D-glutamic acid, D-histidine, D-arginine, D-lysine, D-hydroxylysine, D-ornithine, L-aspartic acid, L-glutamic acid, L-histidine, L-arginine, L-lysine, L-hydroxylysine or L-ornithine.

As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar, aromatic and polar. However, the nonpolar ring is dominant and so tyrosine is generally considered to be nonpolar. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

In some embodiments, polar amino acids as contemplated herein may include, for example, arginine, asparagine, aspartic acid, cysteine, glutamic acid, glutamine, histidine, homocysteine, lysine, hydroxylysine, ornithine, serine, threonine, and structurally related amino acids. In one embodiment the polar amino is an ionizable amino acid such as arginine, aspartic acid, glutamic acid, histidine, hydroxylysine, lysine, or ornithine.

Examples of polar or nonpolar amino acid residues that can be utilized include, for example, alanine, valine, leucine, methionine, isoleucine, phenylalanine, tryptophan, tyrosine and the like.

The term "salts" herein refers to both salts of carboxyl groups and to acid addition salts of amino groups of the peptides described herein or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid salts include, for example, salts with mineral acids such as, for example, hydrochloric acid or sulphuric acid, and salts with organic acids such as, for example, acetic acid or oxalic acid. Of course, any such salts must have substantially similar activity to the peptides disclosed herein or their analogs.

The definition "functional derivatives" as herein used refers to derivatives which can be prepared from the functional groups present on the lateral chains of the amino acid moieties or on the terminal N- or C-groups according to known methods and are comprised in the disclosure when they are pharmaceutically acceptable i.e. when they do not destroy the protein activity or do not impart toxicity to the pharmaceutical compositions containing them. Such derivatives may include, for example, esters or aliphatic amides of the carboxyl-groups and N-acyl derivatives of free amino groups or O-acyl derivatives of free hydroxyl-groups and are formed with acyl-groups as for example alcanoyl- or aroyl-groups.

The "precursors" are compounds which are converted into the peptides disclosed herein in the human or animal body.

The peptides of the present disclosure may be prepared by any well known procedure in the art, such as solid phase synthesis or liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their α-amino groups and side chain functional groups protected with appropriate protective groups are condensed one by one in order from the C-terminus to the N-terminus, and one where the amino acids bound to the resin or the protective group of the α-amino groups of the peptides are released, the peptide chain is thus extended in this manner. Solid phase synthesis methods are largely classified by the tBoc method and the Fmoc method, depending on the type of protective group used.

Typically used protective groups include tBoc (t-butoxycarbonyl), Cl—Z (2-chlorobenzyloxycarbonyl), Br—Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and C12-Bzl (2,6dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups).

After synthesis of the desired peptide, it is subjected to the de-protection reaction and cut out from the solid support. Such peptide cutting reaction may be carried with hydrogen fluoride or trifluoromethane sulfonic acid for the Boc method, and with TFA for the Fmoc method.

The crude peptide thus obtained is then subjected to purification. Purification is carried out by any one of the methods known for this purpose, i.e. any conventional procedure involving extraction, precipitation, chromatography, electrophoresis, or the like. For example, HPLC (high performance liquid chromatography) can be used. The elution can be carried using a water-acetonitrile-based solvent commonly employed for protein purification.

The peptide described herein can be provided in substantially purified form, in order to be suitable for use in pharmaceutical compositions, as active ingredient, in pathologies that require MNTF activity and/or modulation thereby.

As used herein, the terms "biologically active peptide" and "biologically active fragment" refer to a peptide or polypeptide in accordance with the above description of motoneuron differentiation factors (MNDF) and/or motoneuronotrophic factors (MNTF) wherein the MNDF differentiates stem cells into motor neurons and the MNTF wherein MNTF exhibits neural protection, repair and therapeutic functions.

The term "complementary" generally refers to the natural binding of polynucleotides by base pairing, for example under permissive salt and temperature conditions. For example, the sequence "A-G-T" binds to the complementary sequence "T-C-A". Complementarity between two single-stranded molecules may be "partial", such that only some of the nucleic acids bind, or it may be "complete", such that total complementarity exists between the single stranded molecules. The degree of complementarity between nucleic acid molecules has significant effects on the efficiency and strength of the hybridization between them. "Hybridizable" and "complementary" are terms that are used to indicate a sufficient degree of complementarity such that binding, such as stable binding sufficient to carry out an intended action, for example, occurs between nucleic acids. It is understood that an oligonucleotide need not be 100% complementary to its target nucleic acid sequence to be hybridizable.

The term "composition" is intended to encompass a product comprising one or more ingredients.

The term "differentiated" is a relative term in which a "differentiated cell" is a cell that has progressed further down the developmental pathway than the cell it is being compared against. As further used herein, a "differentiated neural cell" generally refers to a partially-differentiated or fully-differentiated cell of the central nervous system (CNS) or peripheral nervous system (PNS). Progenitor cells are parent cells which, during development and differentiation, give rise to a distinct cell lineage by a series of cell divisions. Neural progenitor cells, for example, are committed to a cell lineage that will develop, eventually, into fully-differentiated neural cells of the CNS or PNS; however, such neural progenitor cells may not yet be dedicated to a particular type, or subclass, of neural cell. Neural progenitor cells may become committed to a cell line that will differentiate into a specific type of neural cell, and, thereafter, give rise to fully-differentiated neural cells. Accordingly, the partially-differentiated neural cell described herein may be a cell, with a neural identity, that has acquired a directional or positional character, or that has committed to developing into a particular class of neural cell, but is not a fully-differentiated neural cell. For example, treatment of ES cells with an MNTF peptide, alone or in combination with a morphogen, such as RA, can give rise to a partially differentiated neural cell or neural progenitor cell as described herein.

A "disorder" is any condition that would benefit from treatment with a molecule or composition described herein. This includes chronic and acute disorders or diseases including those pathological conditions that predispose the mammal to the disorder in question.

"Feeder cells" or "feeders" include cells of one type that are co-cultured with cells of another type, generally to provide an environment in which the cells of the second type can grow. For example, certain types of pPS cells can be supported by primary mouse embryonic fibroblasts, immortalized mouse embryonic fibroblasts, or human fibroblast-like cells differentiated from hES cell.

By "functional equivalent" is meant a peptide possessing a biological activity substantially similar to that of, for example, the MLSAFSRYAR domain(s), as well as conserved, homologous 6-mer (e.g., SEQ ID NO: 2), 7-mer, 8-mer, 9-mer, or 10-mer, and derivatives thereof. It includes "fragments", "variants", "analogs", "homologs", or "chemical derivatives" possessing such activity or characteristic. Functional equivalents of the MLSAFSRYAR domain(s) and others described above, then, may or may not share an identical amino acid sequences, and conservative or non-conservative amino acid substitutions of conventional or unconventional amino acids are possible.

As used herein, the term "MLSAFSRYAR, WMLSAFS, and FSRYAR domains" refers to a polypeptide domain demonstrated herein to be sufficient for the differentiation of stem cells into motor neurons, and to peptides and/or molecules capable of mimicking their structure and/or function. Additional domains are as illustrated in SEQ ID NOs: 1-142.

In certain aspects, a peptide comprising the amino acid of any of sequence ID NOs: 1-142, as well as functional equivalents thereof, is provided.

The term "gene product" refers to an RNA molecule transcribed from a gene, or a polypeptide encoded by the gene or translated from the RNA.

A "growth environment" is an environment in which cells of interest can proliferate, differentiate, or mature in vitro under appropriate conditions. Such conditions may include, for example, the medium in which the cells are cultured, any growth factors or differentiation-inducing factors that may be present, and a solid surface or supporting structure.

The terms "modulator" and "modulation" as used herein in its various forms is intended to encompass up-regulation or inhibition in whole or in part of the expression or action or activity of a particular target.

For the purposes of this disclosure, the terms "neural progenitor cell" or "neural precursor cell" include a cell that can generate progeny that are either neuronal cells (e.g. neuronal precursors or mature neurons) or glial cells (e.g. glial precursors, mature astrocytes, or mature oligodendrocytes). The cells typically express some of the phenotypic markers that are characteristic of the neural lineage, and they do not generally produce progeny of other embryonic germ layers when cultured alone in vitro.

A "neuronal progenitor cell" or "neuronal precursor cell" include a cell that can generate progeny that are mature neurons and sometimes also have the capability to generate glial cells.

A "multipotent neural progenitor cell population" includes a cell population that has the capability to generate both progeny that are neuronal cells, progeny that are glial cells, and sometimes other types of cells. This term does not require that individual cells within the population have the capability of forming both types of progeny, although individual cells that are multipotent neural progenitors may be present.

The terms "peptidomimetic" and "mimetic" include naturally occurring and synthetic chemical compounds that may have substantially the same structural and functional characteristics of protein regions which they mimic.

Peptide analogs with properties analogous to those of the template peptide may be non-peptide drugs. "Peptide mimetics" or "peptidomimetics," which include peptide-based compounds, also include such non-peptide based compounds (Fauchere, *J. Adv. Drug Res.* 15: 29 (1986); Veber and Freidinger; *TINS;* 392 (1985); and Evans et al., *J. Med. Chem.* 30: 1229 (1987); Beeley N., *Trends Biotechnol. June;* 12(6): 213-6 (1994); Kieber-Emmons T, et al.; *Curr Opin Biotechnol. August;* 8(4): 435-41 (1997). Peptide mimetics that are structurally similar to therapeutically useful peptides may be used to produce an equivalent or enhanced therapeutic or prophylactic effect. Generally, peptidomimetics are structurally identical or similar to a paradigm polypeptide (i.e., a polypeptide that has a biological or pharmacological function or activity), but can also have one or more peptide linkages optionally replaced by a linkage selected from the group consisting of, for example, —CH$_2$NH—, —CH$_2$S—, —CH$_2$—CH$_2$—, —CH=CH— (cis and trans), —COCH$_2$—, —CH(OH)CH$_2$—, and —CH$_2$SO—. The mimetic can be either entirely composed of natural amino acids, or non-natural analogs of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity.

As used herein, "preventing" means preventing in whole or in part, or ameliorating or controlling.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented.

As used herein, an "effective amount" in reference to the compounds or compositions described herein refers to the amount sufficient to induce a desired biological, pharmaceutical, or therapeutic result. That result can be alleviation of the signs, symptoms, or causes of a disease or disorder or condition, or any other desired alteration of a biological system.

As used herein, "simultaneously" is used to mean that the MNTF composition is administered concurrently with one or more other therapeutic agents, whereas the term "in combination" is used to mean they are administered, if not simultaneously or in physical combination, then "sequentially" within a timeframe that they both are available to act therapeutically. Thus, administration "sequentially" may permit one agent to be administered within minutes (for example, 1, 2, 3, 4, 5, 10, 15, 20, 25, 30) minutes or a matter of hours, days, weeks or months after the other provided that both the MNTF and the one or more other therapeutic agent are concurrently present in effective amounts. The time delay between administration of the components will vary depending on the exact nature of the components, the interaction there between, and their respective half-lives.

As used herein, the term "peptide analogs" refer to the compounds with properties analogous to those of the template peptide and can be non-peptide drugs. "Peptide mimetics" or "peptidomimetics," which include peptide-based compounds, also include such non-peptide based compounds such as peptide analogs. Peptide mimetics that are structurally similar to therapeutically useful peptides can be used to produce an equivalent or enhanced therapeutic or prophylactic effect. Generally, peptidomimetics are structural or functional mimics (e.g. identical or similar) to a paradigm polypeptide (i.e., a polypeptide that has a biological or pharmacological function or activity), but can also have one or more peptide linkages optionally replaced by a linkage selected from the group consisting of, for example, —CH₂NH—, —CH₂S—, —CH₂—CH₂—, —CH=CH— (cis and trans), —COCH₂—, —CH(OH)CH₂—, and —CH₂SO—. The mimetic can be either entirely composed of natural amino acids, synthetic chemical compounds, non-natural analogs of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity.

As used herein, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. A "domain" of a protein is also a fragment, and comprises the amino acid residues of the protein often required to confer activity or function.

The phrase "percent (%) identity" refers to the percentage of sequence similarity found in a comparison of two or more sequences. Percent identity can be determined electronically using any suitable software, for example. Likewise, "similarity" between two sequences (or one or more portions of either or both of them) is determined by comparing the sequence of one sequence to a second sequence.

"Pharmaceutically acceptable" compounds and other ingredients of a composition or formulation, for example, a carrier, diluent or excipient, are those that are suitable for administration to a recipient thereof.

The term "stringent conditions" refers to conditions that permit hybridization between polynucleotides encoding the MNTF peptides of interest. Stringent conditions can be defined by salt concentration, the concentration of organic solvent (for example, formamide), temperature, and other conditions well known in the art. Stringency can be increased by reducing the concentration of salt, increasing the concentration of organic solvents, (for example, formamide), or raising the hybridization temperature. For example, stringent salt concentration will ordinarily be less than about 750 mM NaCl and 75 mM trisodium citrate, such as less than about 500 mM NaCl and 50 mM trisodium citrate, and can be less than about 250 mM NaCl and 25 mM trisodium citrate. Low stringency hybridization can be obtained in the absence of organic solvent, for example, formamide, while high stringency hybridization can be obtained in the presence of an organic solvent (for example, at least about 35% formamide, such as at least about 50% formamide). Stringent temperature conditions will ordinarily include temperatures of at least about 30° C., of at least about 37° C., or of at least about 42° C. Varying additional parameters, for example, hybridization time, the concentration of detergent, for example, sodium dodecyl sulfate (SDS), and the inclusion or exclusion of carrier DNA, are well known to those skilled in the art. Various levels of stringency are accomplished by combining these various conditions as needed, and are within the skill in the art. Stringent hybridization conditions may also be defined by conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, for example, Berger and Kimmel, Methods In Enzymology, Vol. 152: *Guide To Molecular Cloning Techniques*, San Diego (1987): Academic Press, Inc and Sambrook et al., Molecular Cloning (1989): A Laboratory Manual, 2nd Ed., Vols. 1-3, Cold Spring Harbor Laboratory). As indicated by standard references, a simple estimate of the Tm value may be calculated by the equation: $Tm=81.5+0.41(\% \text{ G+C})$, when a nucleic acid is in aqueous solution at 1 M NaCl (see for example, Anderson and Young, "Quantitative Filter Hybridization" in Nucleic Acid Hybridization (1985)). The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (for example for example, the presence or absence of formamide, dextran sulfate, polyethylene glycol). The effects of these factors are well known and are discussed in standard references in the art, see for example, Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (for example, 10 to 50 nucleotides) and at least about 60° C. for long probes (for example, greater than 50 nucleotides). As noted, stringent conditions may also be achieved with the addition of destabilizing agents such as formamide, in which case lower temperatures may be employed. As described herein, the polynucleotide may be a polynucleotide which hybridizes to a target mRNA under conditions of medium to high stringency such as 0.03M sodium chloride and 0.03M sodium citrate at from about 50 to about 60 degrees centigrade.

As used herein, "subject" refers to any animal classified as a mammal, including humans, domestic and farm animals, and zoo, sports, or pet animals, such as dogs, horses, cats, sheep, pigs, cows, etc. The subject can be a human.

The term "therapeutically effective amount" means the amount of the subject compound that will elicit a desired response, for example, a biological or medical response of a tissue, system, animal or human that is sought, for example, by a researcher, veterinarian, medical doctor, or other clinician.

"Treatment" refers to both therapeutic treatment and prophylactic or preventive measures. Those in need of treatment include those already with the disorder as well as those in which the disorder is to be prevented.

The term "vector" refers to a nucleic acid molecule amplification, replication, and/or expression vehicle in the form of a plasmid, phage, viral, or other system (be it naturally occurring or synthetic) for the delivery of nucleic acids to cells where the plasmid, phage, or virus may be functional with bacterial, yeast, invertebrate, and/or mammalian host cells. The vector may remain independent of host cell genomic DNA or may integrate in whole or in part with the genomic DNA. The vector will generally but need not contain all necessary elements so as to be functional in any host cell it is compatible with. An "expression vector" is a vector capable of directing the expression of an exogenous polynucleotide, for example, a polynucleotide encoding a binding domain fusion protein, under appropriate conditions.

As described herein, the terms "homology and homologues" may peptides containing amino acid sequence homologies to the protein sequence of interest. Such peptide typically has at least about 70% homology, and can be at least about 80%, 90%, 95%, 97% or 99% homology with the relevant sequence, for example over a region of at least about 15, 20, 30, 40, 50, 100 more contiguous amino acid/polypeptide of the homologous sequence.

Homology may be calculated based on any method in the art. For example the UWGCG Package provides the BEST-FIT program which can be used to calculate homology (for example used on its default settings) (Devereux et al., Nucleic Acids Research 12, p 387-395 (1984)). The PILEUP and BLAST algorithms can be used to calculate homology or line up sequences (typically on their default settings), for example as described in Altschul S. F.; *J Mol Evol* 36: 290-300 (1993); Altschul, S. F. et al.; *J Mol Biol* 215: 403-10 (1990). Software for performing BLAST analyses is publicly available through the National Center for Biotechnology Information. This algorithm involves first identifying high scoring sequence pair by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff *Proc. Natl. Acad. Sci. USA* 89: 10915-10919 (1992)) alignments (B) of 50, expectation (E) of 10, M=5, N=4, and a comparison of both strands.

The BLAST algorithm performs a statistical analysis of the similarity between two sequences; see e.g., Karlin and Altschul *Proc. Natl. Acad. Sci. USA* 90: 5873-5787 (1993). One measure of similarity provided by the BLAST algorithm is the smallest sum probability (P (N)), which provides an indication of the probability by which a match between two nucleotide or amino acid sequences would occur by chance. For example, a sequence is considered similar to another sequence if the smallest sum probability in comparison of the first sequence is less than about 1, and can be less than about 0.1, 0.01, or 0.001.

The homologous sequence typically differs from the relevant sequence by at least (or by no more than) about 1, 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background. Selective hybridization is typically achieved using conditions of medium to high stringency (for example 0.03M sodium chloride and 0.03M sodium citrate at from about 50 degrees C. to about 60 degrees C.). However, such hybridization may be carried out under any suitable conditions known in the art (see Sambrook et al., Molecular Cloning: A Laboratory Manual (1989)). For example, if high stringency is required, suitable conditions include 0.2×SSC at 60 degrees C. If lower stringency is required, suitable conditions include 2×SSC at 60 degrees C.

The term "recombinant" refers to a polynucleotide synthesized or otherwise manipulated in vitro (for example, "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process refers to use of recombinant nucleic acid techniques, for example, involving human intervention in the nucleotide sequence, typically selection or production. Alternatively, it can be a polynucleotide made by generating a sequence comprising a fusion of two or more fragments that are not naturally contiguous to each other. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

A "recombinant host cell" is a cell that contains a vector, for example, a cloning vector or an expression vector, or a cell that has otherwise been manipulated by recombinant techniques to express a protein of interest.

General Aspects of Treatment

Methods of treating a subject with a neuronal disorder comprising administering to the subject a motoneuronotropic factor (MNTF) peptide analog is provided.

As used herein, neuronal disorder may include disease, disorder or conditions associated with or characterized in whole or in part by acute, progressive or gradual loss of functional neural tissue. Exemplary neuronal disorder may include spinal cord injury, neurodegenerative disease, stroke or transient or prolonged ischemic condition (e.g. cerebral ischemia), Huntington's Disease (HD), Parkinson's Disease (PD), Multiple Sclerosis (MS), ALS, Alzheimer's Disease, diabetic neuropathy, spinal muscular Atrophy (SMA), and transverse myelitis.

In addition, exemplary neurodegenerative disease may also include Alexander disease, Alper's disease, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, HIV-associated dementia, Kennedy's disease, Krabbe disease, Lewy body dementia, Machado-Joseph disease (Spinocerebellar ataxia type 3), Multiple System Atrophy, Narcolepsy, Neuroborreliosis, Pelizaeus-Merzbacher Disease, Pick's disease, Primary lateral sclerosis, Prion diseases, Refsum's disease, Sandhoff disease, and Schilder's disease.

A "neurodegenerative disease" refers to a condition associated with central or peripheral nervous system characterized by progressive, gradual, loss of functional neural tissue.

"Amyotrophic lateral sclerosis" or "ALS" are terms understood in the art and as used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

Exemplary clinical symptoms of ALS include muscle weakness, muscle wasting, muscle cramping, muscle twitching, slurred or slow speech, difficulty swallowing, and slow, uncoordinated movements. Further exemplary clinical symptoms of ALS include those detectable in a biological sample obtained from a subject having or suspected of having ALS, e.g., increased CD4:CD8 cell ratio compared to normal, decreased number of CD14+ cells compared to normal, increased expression of HLA-DR on CD 14+ cells compared to normal CD14+ cells, increased levels of activated monocytes or macrophages compared to normal, the presence of proliferating macrophages, and decreased serum IgG and/or IgM compared to normal, where "normal" as used herein means a subject unaffected by ALS or cells from such an unaffected subject. "Treating" thus encompasses achieving a decrease in one or more clinical symptoms, which decrease may have desirable concomitant effects, such as to palliate, ameliorate, stabilize, reverse, slow or delay progression of disease, delay and/or even prevent onset of disease.

"Multiple sclerosis" or "MS" are terms understood in the art and as used herein to denote a progressive neurodegenerative disease resulting in destruction of the myelin covering of nerve cells, particularly of the brain and spinal cord. As used herein, "MS" includes all of the classifications of MS known in the art, including, but not limited Relapsing-remitting (RRMS) (typically characterized by partial or total recovery after attacks (also called exacerbations, relapses, or flares)), Secondary progressive MS (SPMS) (generally characterized by fewer relapses, with an increase in disability and symptoms), and Primary progressive MS (PPMS) (generally characterized by progression of symptoms and disability without remission).

Exemplary clinical symptoms of MS include fatigue (also referred to as MS lassitude), muscle fatigue, paresthesias, difficulty in walking and/or balance problems, abnormal sensations such as numbness, prickling, or "pins and needles", pain, bladder dysfunction, bowel dysfunction, changes in cognitive function (including problems with memory, attention, concentration, judgment, and problem-solving), dizziness and vertigo, emotional problems (e.g., depression), sexual dysfunction, and vision problems. Severe cases can involve partial or complete paralysis (such as blurred or double vision, red-green color distortion, or blindness in one eye). Other symptoms include headache, hearing loss, itching, seizures, spasticity, speech and swallowing disorders, and tremors. Further exemplary clinical symptoms of MS include those detectable in a biological sample obtained from a subject having or suspected of having MS, e.g., increased CD4:CD8 cell ratio compared to normal, decreased number of CD14+ cells compared to normal, increased expression of HLA-DR on CD14+ cells compared to normal CD14+ cells, increased levels of activated monocytes or macrophages compared to normal, the presence of proliferating macrophages, and decreased serum IgG and/or IgM compared to normal, where "normal" as used herein means a subject unaffected by MS or cells from such an unaffected subject. "Treating" thus encompasses achieving a decrease in one or more clinical symptoms, which decrease may have desirable concomitant effects, such as to palliate, ameliorate, stabilize, reverse, slow or delay progression of disease, delay and/or even prevent onset of disease.

"Alzheimer's disease" or "AD" are terms understood in the art and used herein to denote a progressive neurodegenerative disease characterized by dementia and defined by the American Psychiatric Association (in DSM IV) as the development of multiple cognitive deficits that includes memory impairment.

Exemplary clinical symptoms of AD include mild forgetfulness, including trouble remembering recent events, activities, or the names of familiar people or things; difficulty in solving simple math problems; trouble remembering how to do simple tasks (e.g., brushing teeth or combing hair); inability to think clearly; difficulty speaking, understanding, reading, or writing; and anxiety or aggression, or tendency to wander away from home.

As used herein, a "subject" can be a vertebrate, such as a mammal, e.g., a human. Mammals include, but are not limited to, farm animals, sport animals, rodents, primates, and pets.

As used herein, Parkinson's disease (also known as Parkinson disease or PD) is characterized in whole or in part by degenerative condition of the central nervous system that often impairs the sufferer's motor skills and speech. Parkinson's disease belongs to a group of conditions called movement disorders. It can be characterized in part by muscle rigidity, tremor, a slowing of physical movement (bradykinesia) and, in extreme cases, a loss of physical movement (akinesia). The primary symptoms are the results of decreased stimulation of the motor cortex by the basal ganglia, normally caused by the insufficient formation and action of dopamine, which is produced in the dopaminergic neurons of the brain. Secondary symptoms may include high level cognitive dysfunction and subtle language problems. PD is both chronic and progressive. PD is the most common cause of parkinsonism, a group of similar symptoms. PD is also called "primary parkinsonism" or "idiopathic PD" (having no known cause). While most forms of parkinsonism are idiopathic, there are some cases where the symptoms may result from toxicity, drugs, genetic mutation, head trauma, or other medical disorders.

Huntington's disease (HD) may be characterized by an autosomal dominant neurodegenerative disorder caused by a CAGE trinucleotide expansion in exon 1 of the Huntington (Htt) gene (E.g. Perutz et al., Trends Biochem. Sci. 1999; 24:58-63; and Rubinsztein et al., J. Med. Genet. 1999; 36:265-270). HD patients may be characterized by the presence of abnormal body movement, dementia, and psychiatric problems.

Overview

The isolation and characterization of two motoneuronotrophic factors (MNTF1 and MNTF2) from rat muscle tissues as well as the subsequent cloning of a recombinant MNTF1-F6 gene derived from a human retinoblastoma cDNA library, is described in U.S. Pat. Nos. 6,309,877, 6,759, 389 and 6,841,531 (as well as co-pending U.S. patent application Ser. Nos. 10/858,144, 10/858,286, 10/858,543 and 10/858,545); all of which are hereby incorporated by reference in their entirety. The MNTF1-F6 gene sequence encodes a 33 amino acid sequence referred to therein as SEQ ID NO:1. Nucleotide sequences encoding MNTF1 polypeptides were found to map within human chromosome 16q22, as described in International Application No. PCT/US2004/038651, which is hereby incorporated by reference in its entirety.

Two overlapping domains within the MNTF1-F6 molecule that appear to be sufficient for the known biological activities of MNTF1 were identified. See, International Application No. PCT/US04/01468 or U.S. patent application Ser. No. 10/541,343, issued as U.S. Pat. No. 7,183,373, which are hereby incorporated by reference in their entirety. Each of these domains, designated herein as the "WMLSAFS" and "FSRYAR" domains, were sufficient to stimulate the proliferation of motor neuron derived cell lines in a manner similar to the MNTF1-F6 33-mer. Similarly, the "FSRYAR" domain is sufficient to direct selective re-enervation of muscle targets by motor neurons in vivo in a manner similar to the MNTF1-F6 33-mer. In addition, the "FSRYAR" domain provides an antigenic epitope sufficient to raise antibody that recognizes any MNTF peptide containing the "FSRYAR" sequence, including the MNTF1-F6 33-mer.

Motoneuron Trophic Factor (MNTF) peaks in expression during week 9 in human fetus gestation period (Di, X. et al., Acta Anatomica Sinica 29:86-89, 1998). Based on the expression of MNTF in the developing human, we reasoned that MNTF may promote the differentiation and/or survival of motoneurons. To examine this, we defined whether MNTF modulates the differentiation of pluripotent embryonic stem cells into motoneurons and enhances the survival of ES cell-derived motoneurons.

As disclosed herein, the inventors have determined that the exposure of ES cells to RA and MNTF analogs directs these cells to generate motor neurons.

Methods of Use

MNTF and truncated MNTF molecules, include but not limited to those comprising the MLSAFSRYAR domain, referred to herein as a motor neuron differentiation factors (MDNF), are demonstrated herein to induce differentiation of stem cells or partially differentiated neuronal cells into motor neurons. Such agents provide a novel method for generating and/or isolating a population of motor neurons from stem cell cultures.

The method described herein comprises contacting an embryonic stem cell with retinoic acid (RA) and a motor neuron differentiation factor (MNDF). In an embodiment described herein, the embryonic stem cell is contacted with RA concomitantly with the motor neuron differentiation factor. Alternatively, the method comprises contacting a partially differentiated neuronal, cell with a motor neuron differentiation factor. The factors are provided in amounts effective to produce a differentiated neural cell. These amounts may be readily determined by the skilled artisan, based upon known procedures and methods disclosed herein.

MNTF1 and/or its peptide analogs also promote the survival of mammalian motor neurons in vitro. Accordingly, the technology described herein provides for the use of an MNTF peptide analog as a growth factor/supplement for neuronal cell cultures, including a method for promoting the survival of stem cell derived neuronal cell lines, by cultivating stem cell derived neuronal cells in vitro with an effective amount of a MNTF peptide analog.

The inventors have also discovered that neurons cultured in the presence of neurotrophic factors survive and elaborate processes. Accordingly, in another embodiment, the method described herein comprises the step of contacting the stem cell derived motor neurons with at least one MNTF peptide analog, e.g., following contact with RA and a motor neuron differentiation factor, such as a MNTF peptide analog as described herein or, alternatively Sonic Hedgehog (Shh), which includes a Shh agonist.

The differentiated motor neurons be isolated or enriched, e.g. by FACS sorting. For example the use of a GFP-based motor neuron marking method permits the characterization of pure populations of ES-cell-derived motor neurons. We have employed this protocol for isolating pure motoneuron population of cells from a mixed population of cells from embryoid bodies. Embryoid bodies are disaggregated to single cells using collagenase and dispase. These single cells are then FACS sorted for GFP, since cells expressing GFP controlled by an HB9 promoter are the true motoneurons in the population.

Accordingly, another aspect of the technology described herein is directed to a method for isolating and/or purifying a population of differentiated neural cells by: (a) obtaining or generating a culture of embryonic stem cells that express enhanced green fluorescent protein (eGFP) under the control of a motor neuron specific promoter; (b) contacting the culture of embryonic stem cells with an amount of a RA and MNTF effective to produce differentiated neural cells that express eGFP; (d) detecting expression of eGFP in the differentiated neural cells; and (f) isolating the differentiated neural cells that express eGFP.

The inventors have discovered that MNTF and certain MNTF analogs are useful for treating neuronal disorder by virtue of their ability to promote the survival, growth, proliferation, and/or maintenance of mammalian neurons. The inventors have further discovered that, according to certain embodiments, a MNTF peptide or a MNTF analog modulates a signal transduction pathway that is independent of the sonic hedgehog pathway (e.g. partially or completely independent, depending on the embodiment). Likewise, the inventors have discovered that MNTF peptides and MNTF analogs modulate certain protein kinase pathways, including the expression or activity of certain tyrosine kinases and growth factor receptors. The signal transduction or protein kinase pathways that are regulated include, for example, sonic hedgehog independent pathways.

Sonic Hedgehog (Shh) is a key component responsible for the ventralization of caudalized neurons, acting via its transmembrane receptor components patched-smoothened. The data presented herein shows that MNTF peptides effectively substitute for sonic hedgehog in the differentiation of murine ES cells in vitro into motor neurons in the presence of retinoic acid (Example 5). Addition of MNTF to these ES cultures result in the expression of mature motor neuron transcription factors (HB9 and Islet ½), expression of the mature motor neuron marker choline acetyl transferase (ChAT), and the generation of neurons capable of conducting action potentials. The data also show that MNTF peptides are capable of generating post-mitotic mature motor neurons in the presence of a specific inhibitor of smoothened receptor signaling (cyclopamine-KAAD). While not wishing to be bound to any particular theory or mechanism, the inventors believe that the data show that MNTF signals through a different pathway than Shh or downstream of smoothened. Based upon data presented herein, the inventors have further determined that MNTF peptides act through the signal transduction pathways described herein to promote the survival, growth, proliferation, and/or maintenance of mammalian neurons. Thus, in another aspect of the technology described herein, a MNTF factor or MNTF analog is administered to modulate the expression or activity of certain signal transduction components. Our data further demonstrates that MNTF treatment of ES cells resulted in the auto-phosphorylation of Tyr972 and Tyr 1162/1163 of the Insulin Receptor (IR) (Example 5). These residues are markers of IR activation. Further, co-immunoprecipitation studies showed the association of specific SH2 domains with IR (p85 subunit for PI3 kinase) as a result of MNTF treatment on the ES cells. Example 5 also shows that blocking the IGF-1R had no effect on the ability of MNTF to generate motor neurons, but blocking IR abolished this ability.

In certain embodiments, an Insulin Receptor substrate protein expression or activity is modulated in response to the administration of a motoneuronotropic factor (MNTF) analog to a patient or to a target organ, tissue, or cell. Insulin Receptor substrate proteins (IRS-proteins) are the effectors of both Insulin and IGF-initiated signaling. They share PH and PTB domains near their N-termini, and multiple Tyr phosphorylation motifs in their C-terminal regions. Proteins which bind to tyrosine-phosphorylated IRS-proteins include PI3 Kinase p85, GRB2, SHP2, Nck, Crk, and Fyn. IRS-1 appears to be principally involved in IGF-signaling and cytoskeletal growth. IRS-2 appears to be an important mediator of Insulin signaling, as genetic ablation results in type II diabetes. IRS-3 is expressed primarily in adipocytes and is a potent activator of PI3 kinase. IRS-4 lacks the tyrosine residues which is used by the other IRS-proteins to bind to SHP2.

In certain embodiments, the protein expression or activity of an IGF-1, IGF-II, or receptor of either is modulated in response to the administration of a motoneuronotropic factor (MNTF) analog to a patient or to a target organ, tissue, or cell. IGF-I and -II signal through the IGF-I Receptor, which is homologous to the Insulin Receptor. The high-affinity IGF-II Receptor does not play a direct role in signaling, but regulates the concentration of free IGF-II. The IGFs are involved in skeletal growth, and are essential for prevention of apoptosis. Serum levels of free IGFs are kept low by the action of IGF binding proteins (IGFBPs), which sequester the IGFs. Overexpression of IGFBPs may induce apoptosis, presumably by reduction of free IGF; IGFBP levels are also altered in some cancers. The IGF-I Receptor is not as mitogenic as some other growth factor receptors, but its ability to activate the PI3 kinase pathway, through the Insulin Receptor Substrate (IRS) proteins, is very important for mediating cell survival.

In certain embodiments, a phosphatidylinositol 3-kinase protein expression or activity is modulated in response to the administration of a motoneuronotropic factor (MNTF) analog to a patient or to a target organ, tissue, or cell. PI3 kinase (phosphatidylinositol 3-kinase) is responsible for phosphorylation of the 3 position of the inositol ring of PI(4,5)P2, to generate PI(3,4,5)P3, a potent second messenger required for survival signaling, and insulin action. PI3 Kinase is a heterodimeric complex composed of an 85 kDa regulatory subunit and a 110 kDa catalytic subunit. Tyrosine phosphorylation of growth factor receptors creates docking sites for binding of p85 (through its SH2 domains) on the receptors; p85 brings with it p110, which is then proximal to its phospho-lipid substrate on the membrane. PI3 Kinase is also activated by Ras, and by the β:γ subunits of heterotrimeric G-proteins. PI3 Kinase is inhibitable by Wortmannin, a useful tool for the study of the PI3 Kinase signaling pathway.

In certain embodiments, an Akt kinase protein expression or activity is modulated in response to the administration of a motoneuronotropic factor (MNTF) analog to a patient or to a target organ, tissue, or cell. Akt is the major known effector of the PI3 kinase pathway. Generation of PIP3 results in the activation of PDK1, which phosphorylates Akt on Thr308, and another kinase (anticipated PDK2) which phosphorylates Akt on Ser473. These phosphorylations additively activate Akt Ser/Thr kinase activity, and the use of phosphorylation state-specific antibodies directed against either of these sites can imply Akt activation. Activation of Akt can be measured directly by immunoprecipitation followed by phosphorylation of a known substrate with radiolabeled ATP. Akt phosphorylates Bad on Ser136, resulting in protection from apoptosis. Other substrates of Akt include GLUT4, cardiac PFK2, and GSK3, which is inactivated by this phosphorylation.

In certain embodiments, a Bad kinase protein expression or activity is modulated in response to the administration of a motoneuronotropic factor (MNTF) analog to a patient or to a target organ, tissue, or cell. Bad, or "Bcl-2 antagonist of cell death" is member of the Bcl-2 family and an important regulator of life versus death. Unphosphorylated Bad dimerizes with Bcl-2 and Bcl-XL, neutralizing their anti-apoptotic activity. Activation of the PI 3-Kinase pathway leads to activation of Akt which phosphorylates Bad on ser-136. MAP Kinase pathways phosphorylate BAD on ser-112 and recently, PKA has been shown to phosphorylate BAD on ser-155. Phosphorylated Bad binds 14-3-3 proteins and perhaps other factors, which sequester Bad from its proapoptotic role. Assays with phosphorylation state-specific antibodies specific to these sites serve as readouts for the activation of the cell survival pathway.

In certain embodiments, a PI(3,4,5)P3-dependent kinase protein expression or activity is modulated in response to the administration of a motoneuronotropic factor (MNTF) analog to a patient or to a target organ, tissue, or cell. PI(3,4,5)P3-dependent kinase 1 (PDK1) is a Ser/Thr kinase which has a PH domain and is strongly stimulated by PIP3. The best-characterized substrate of PDK1 is Akt, which is phosphorylated by PDK1 on Thr308, contributing to Akt activation. Two isoforms of PDK1 have been identified. PDK1 is also thought to play a role in the activation of p70 S6 Kinase, and is important for signaling from the T-cell Receptor to NFκB during T-cell activation.

In certain embodiments, a Bax protein expression or activity is modulated in response to the administration of a motoneuronotropic factor (MNTF) analog to a patient or to a target organ, tissue, or cell. The Bax protein, which shares highly conserved domains with Bcl-2, can form ion-conducting channels in the lipid bilayers of mitochondria, which play an essential role in the apoptotic pathway of many cells by releasing apoptogenic proteins into the cytosol. Bax presents an interesting therapeutic target for many diseases involving apoptosis such as cancer or neurodegenerative disorders.

In certain embodiments, a p53 gene product expression or activity is modulated in response to the administration of a motoneuronotropic factor (MNTF) analog to a patient or to a target organ, tissue, or cell. The p53 gene is mutated in approximately half of all human cancers. Its gene product is involved in the cellular response to cytotoxic stresses, and together with p19ARF, induces expression of p21Cip1, to cause cell cycle arrest. In addition, p53 is able to induce apoptosis, both by transcriptional and non-transcriptional mechanisms. The amino-terminal 83 amino acids of p53 contain the transactivation domain, as well as the region involved in transcription-independent growth suppression. The carboxy-terminal region contains the DNA-binding domain, which is regulated by three phosphorylation events, and potentially by acetylation also.

In certain embodiments, a Nitric Oxide Synthases protein expression or activity is modulated in response to the administration of a motoneuronotropic factor (MNTF) analog to a patient or to a target organ, tissue, or cell. Nitric Oxide Synthases (NOS) are dimeric, heme-containing enzymes which produce nitric oxide, and contain a c-terminal reductase and an n-terminal oxygenase domain. Three categories of NOS include nNOS/NOS I/NOS1, expressed primarily in neuronal tissue, iNOS/NOS II/NOS2, inducible in macrophages and certain other cells by inflammatory stimuli, and eNOS/NOS III/NOS3, an epithelial form of constitutively expressed NOS. nNOS and eNOS, which are constitutively expressed, require Ca2+ for activity, and are regulated by Ca2+ influx. iNOS is not dependent on Ca2+. Phosphorylation of the different isoforms at a number of sites has varied effects on protein activity; some are inhibitory and some are activating.

In certain embodiments, a Glycogen Synthase Kinase 3 protein expression or activity is modulated in response to the administration of a motoneuronotropic factor (MNTF) analog to a patient or to a target organ, tissue, or cell. Glycogen Synthase Kinase 3 (GSK) differs from most serine/threonine kinases in that it is active in the absence of the action of signaling pathways. Two isoforms exist, GSK3α and GSK3β. The function of GSK3 is to phosphorylate Glycogen Synthase and thereby inactivate it. Insulin action stimulates the PI3 Kinase pathway, resulting in Akt activation, which phosphorylates and inactivates GSK3. Glycogen Synthase is then rapidly dephosphorylated, and activated. Other GSK3 substrates include Jun (on inhibitory sites), and eIF2B. Phosphorylation of Tau by GSK3 may relate to development of Alzheimer's disease. Phosphorylation state-specific antibodies directed against the Akt site (Ser21) on GSK3 are suitable for surrogate assays of the activation state of the pathway.

In certain embodiments, a Caspase protein expression or activity is modulated in response to the administration of a motoneuronotropic factor (MNTF) analog to a patient or to a target organ, tissue, or cell. Cysteine aspartyl proteases related to the *C. elegans* CED-3 death protein comprise the caspase family. All are expressed as proenzymes which are activated by proteolysis. With respect to their roles in apoptosis, Caspases can be subdivided into initiator (Caspases 8, 9, 10) and effector (Caspases 3, 6, 7) caspases, depending on whether they are activated by receptor clustering (initiator) or by mitochondrial permeability transition (effector). Effector caspases, most notably Caspase 3, cleave numerous substrates to effect the morphological changes associated with apoptosis. Among Caspase 3 substrates are DFF45/ICAD, which frees up the DNAse subunit of DFF to cause chromatin degradation, as well as gelsolin, PAK2, D4GDI, all of which are involved in cytoskeletal organization, nuclear lamins and PARP. The significance of PARP cleavage is not clear, but it is an excellent marker for caspase activation and the presumption of ongoing apoptosis.

In certain embodiments, a RAS gene product expression or activity is modulated in response to the administration of a motoneuronotropic factor (MNTF) analog to a patient or to a target organ, tissue, or cell. Ras proteins are small GTP-binding proteins which unlike the heterotrimeric G-proteins contain all GTPase and effector functions within a single polypeptide. At least three isoforms of Ras exist, Ki-Ras, Ha-Ras, and N-Ras, with distinct expression patterns but similar signaling activity. Ras is palmitoylated and farnesylated at the carboxy terminus, anchoring it in the membrane. In resting cells, Ras is loaded with GDP, and is activated subsequent to growth factor stimulation of receptors, which recruit Ras Guanine nucleotide Exchange Factors to the plane of the membrane. Proximity of exchange factors to the Ras proteins causes release of GDP, and its replacement by GTP. In its GTP-bound form, Ras binds several proteins, including Raf, RalGDS, and PI3 Kinase. Inactivation of Ras occurs by GTP hydrolysis, which is greatly accelerated by RasGAP or NF-1, two known Ras GTPase Activating Proteins. It is possible to assay for Ras activation by incubation of lysates with the Ras-binding domain of Raf-1, which selectively binds to Ras:GTP.

Stem Cell Cultures

Embryonic stem (ES) cells are cultured cells, derived from the pluripotent inner cell mass of blastocyst stage embryos that are capable of replicating indefinitely. In general, ES cells have the potential to differentiate into other cells (i.e., they are pluripotent); thus, they may serve as a continuous source of new cells. Embryonic stem cells may be obtained from any animal, such as from a mammal (e.g., human, domestic animal, or commercial animal). In one embodiment, the embryonic stem cell is a murine embryonic stem cell. In another embodiment, the embryonic stem cell is obtained from a human.

Suitable methods for culturing mammalian stem cells are known in the art, e.g., as set forth in U.S. patent application Ser. Nos. 10/362,437, 10/789,266, 10/789,308, 10/928,805 and U.S. Pat. No. 6,833,269, which are all incorporated herein in their entirety. Unless explicitly specified otherwise, the technology described herein can be practiced using stem cells of any vertebrate species (e.g., stem cells from humans; as well as non-human primates, domestic animals, livestock, and other non-human mammals). Included amongst the stem cells suitable for use as described herein are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells.

In certain embodiments, prototype "primate Pluripotent Stem cells" (pPS cells) are used. pPS cells include pluripotent cells derived from pre-embryonic, embryonic, or fetal tissue at any time after fertilization. Under appropriate conditions, they are capable of producing progeny of several different cell types that are derivatives of the three germinal layers (endoderm, mesoderm, and ectoderm). pPS cells encompass embryonic cells of various types, including human embryonic stem (hES) cells as described by Thomson et al., Science 282:1145 (1998); embryonic stem cells from other primates, such as Rhesus stem cells (Thomson et al., *Proc. Natl. Acad. Sci. USA* 92:7844, (1995)), marmoset stem cells (Thomson et al., *Biol. Reprod.* 55:254 (1996) and human embryonic germ (hEG) cells (Shamblott et al., *Proc. Natl. Acad. Sci. USA* 95:13726 (1998), as well as other types of pluripotent cells known in the art. Any cells of primate origin that are capable of producing progeny that are derivatives of all three germinal layers are included, regardless of whether they were derived from embryonic tissue, fetal tissue, or other sources. The pPS cells are generally not derived from a malignant source, and can be karyotypically normal.

pPS cell cultures are described as "undifferentiated" when a substantial proportion of stem cells and their derivatives in the population display morphological characteristics of undifferentiated cells which are readily apparent when compared to differentiated cells of embryo or adult origin. The undifferentiated pPS cells are easily recognized by those skilled in the art, and typically appear in the two dimensions of a microscopic view in colonies of cells with high nuclear/cytoplasmic ratios and prominent nucleoli. It is common for colonies of undifferentiated cells within the population to often be surrounded by neighboring cells that are differentiated.

Differentiated Neural Cells

Suitable methods for culturing progenitor, partially differentiated and fully differentiated neural cells are known in the art, e.g., as set forth in U.S. patent application Ser. Nos. 10/362,437, 10/789,266, 10/789,308, 10/928,805 and U.S. Pat. No. 6,833,269, which are all incorporated herein in their entirety.

Additionally, as used herein, a "neuronal cell", or "neuron", is a conducting or nerve cell of the nervous system that typically consists of a cell body (perikaryon) that contains the nucleus and surrounding cytoplasm; several short, radiating processes (dendrites); and one long process (the axon), which terminates in twig-like branches (telodendrons), and which may have branches (collaterals) projecting along its course. Examples of neurons include motor neurons.

Characterization of Differentiated Neural Cells

Differentiation of ES cells into partially- or fully-differentiated neural cells may be detected by known cellular or molecular procedures, and assays and methods disclosed herein. For example, the cell cultures may be probed for a neuronal marker, such as NeuN (neuronal marker) and/or specific motor neuron markers like HB9 or CHAT.

In another embodiment, the differentiated neural cell is genetically marked, in that it expresses enhanced green fluorescent protein (eGFP), as described herein. The eGFP genetic marker may be particularly useful in a method for isolating and/or purifying a population of differentiated neural cells, or in a method for monitoring repopulation of a spinal cord.

Retinoic Acid

RA, or vitamin A, is an aldehyde molecule that is believed to be a morphogen. RA is readily available; it may be obtained, for example, from Sigma Chemical Co. (St. Louis, Mo.). Treatment with RA at final concentration of about 0.0.001-1 µM results in efficient differentiation of stem cells to neural progenitors.

MNTF Peptides

As those of skill familiar with the art and the disclosure will appreciate, sequences comprising the MNTF active domain and peptide analogs thereof can impart neural protection, repair and therapeutic functions on motorneurons in vitro and in vivo. The MNTF factors described herein may be produced synthetically or recombinantly, or isolated from native cells.

The sequence of amino acid residues in a protein or peptide comprising the MNTF peptide analogs of the present disclosure are designated herein either through the use of their commonly employed three-letter designations or by their single-letter designations. A listing of these three-letter and one-letter designations may be found in textbooks such as Biochemistry, Second Edition, Lehninger, A., Worth Publishers, New York, N.Y. (1975). When the amino acid sequence is listed horizontally, the amino terminus is intended to be on the left end whereas the carboxy terminus is intended to be at the right end.

It will be appreciated by those of skill that the precise chemical structure of peptides comprising the various MNTF peptide analogs will vary depending upon a number of factors. For example, a given polypeptide may be obtained as an acidic or basic salt, or in neutral form, since ionizable carboxyl and amino groups are found in the molecule. For the purposes of the disclosure, then, any form of the peptides comprising the WMLSAFS, FSRYAR, MLSAFSRYAR, domain(s), as well as other sequences/domains listed in SEQ ID NOs: 1-142, which retains a biological activity of the MNTF1 33mer peptide, is intended to be within the scope of the technology described herein.

Figure 25A:
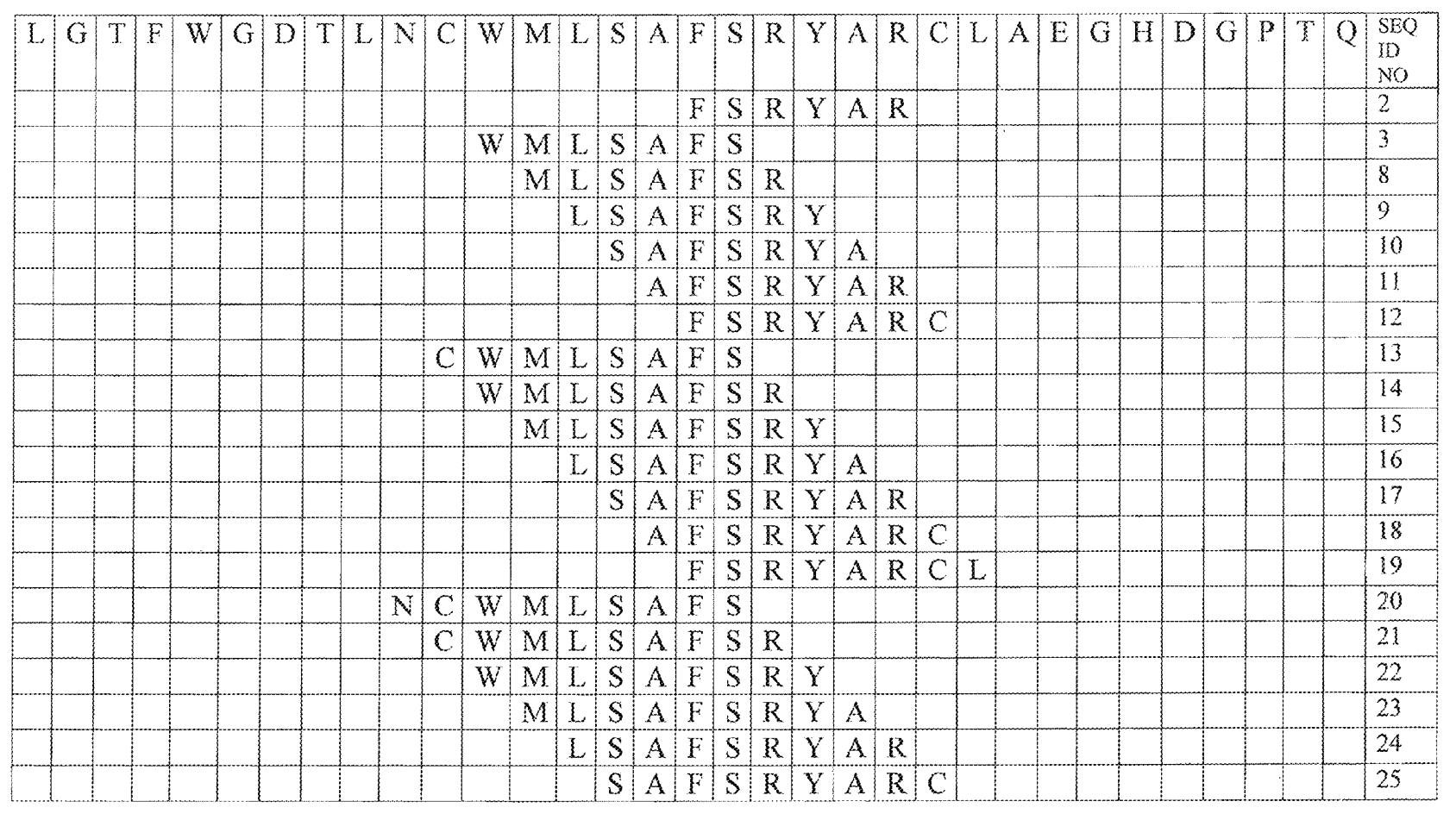
Figure 25C:
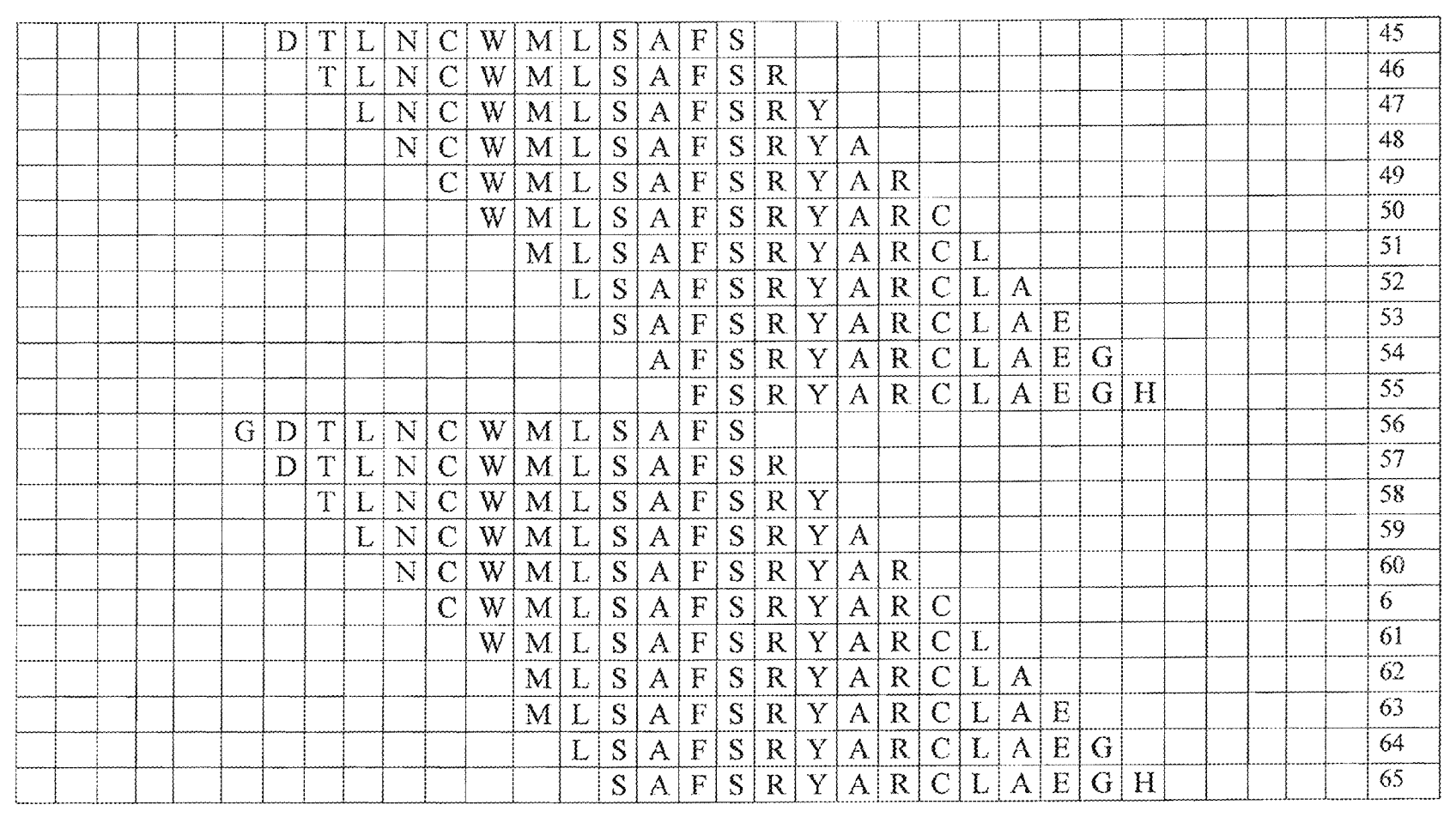
Figure 25D:
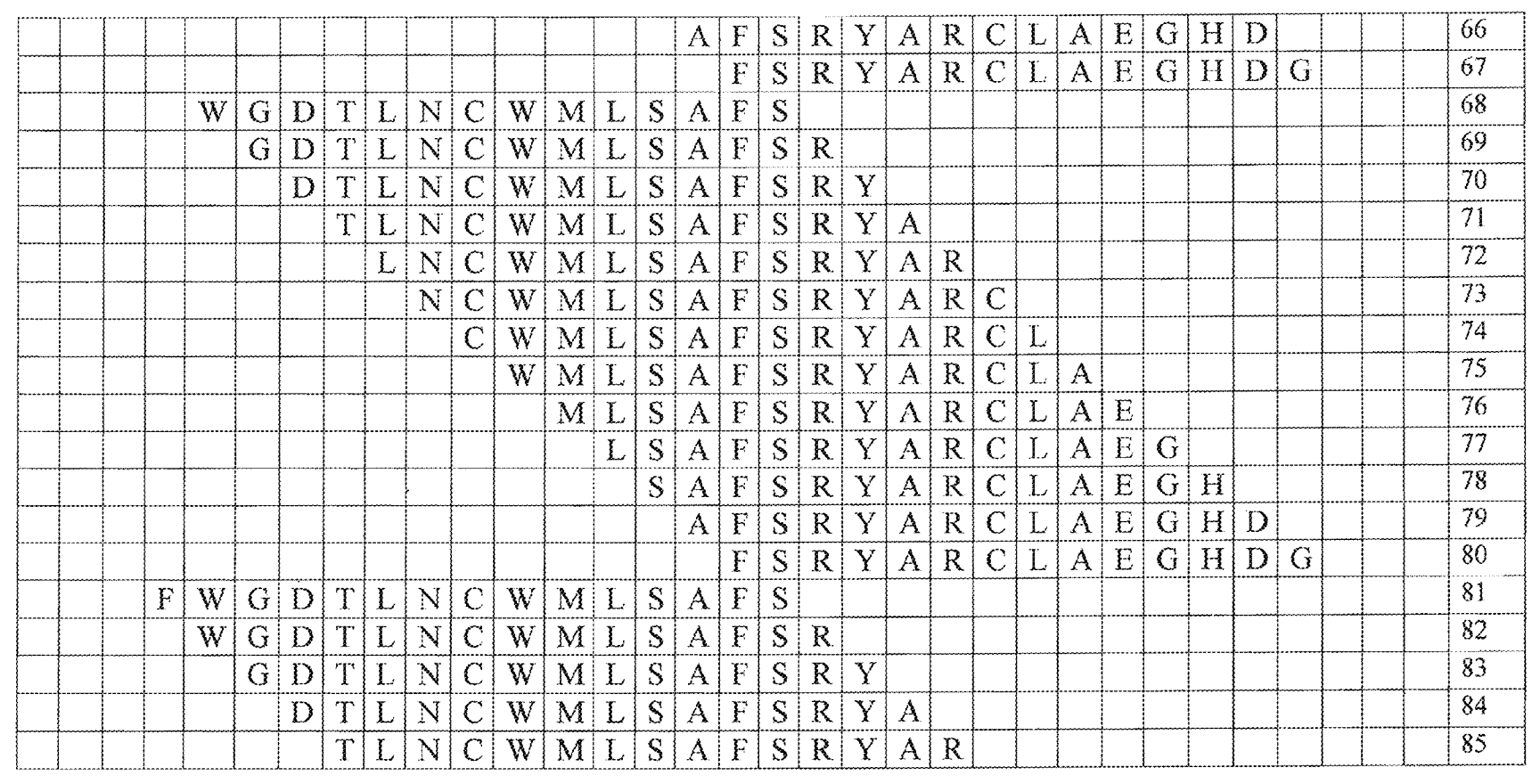

FIG. 25 illustrates certain exemplary embodiments of MNTF peptides in accordance with the present disclosure.

MNTF1-F6 33-mer

In U.S. Pat. No. 6,309,877, there is provided a polypeptide having the following amino acid sequence: LGTFWGDTLN CWMLSAFSRY ARCLAEGHDG PTQ (SEQ ID NO: 1). The polypeptide having this sequence is referred to herein as the MNTF1 33-mer.

Recombinant protein containing this sequence reacted with monoclonal antibody to MNTF-1, maintained motoneuron viability, increased neurite outgrowth, reduced motoneuron cell death/apoptosis and supported the growth and "spreading" of motoneurons into giant, active neurons with extended growth cone-containing axons.

The MNTF1 33-mer was synthesized by solid phase synthesis for use in the examples below. This MNTF-1 molecule will be referred to hereinafter as the "33mer." When used in conjunction with a low concentration of RA, the linear 33-mer induced differentiation of ES cells into motor neurons. Moreover, MNTF1 induced differentiation of ES cells was not blocked by an inhibitor of the Sonic Hedgehog signal transduction pathway. Treatment of the embryoid bodies with MNTF1 33-mer was associated with autophosphorylation of the insulin receptor (IR) and/or insulin-like growth factor receptor (IGF-R), thus indicating MNTF operates through an IR/IGF-R mediated signal transduction pathway.

The present disclosure includes the use of peptide analogs of MNTF1 that retain the ability of MNTF1 to exert neuroprotection, promote survival, maintenance and/or repair of motorneurons; or in certain instances, to differentiate stem cells into motor neurons. An MNTF peptide analog for use as described herein is typically 6 to 33 amino acids in length and may contain WMLSAFS domain (SEQ ID NO: 3) corresponding to amino acid residues 12 to 18 of SEQ ID NO:1, or the FSRYAR domain (SEQ ID NO: 2) corresponding to amino acid residues 17 to 22 of SEQ ID NO: 1. Additionally, certain embodiments of the MNTF peptide analog include a fragment of 6 to 33 consecutive amino acid residues of SEQ ID NO: 1 containing the active domain (SEQ ID NOs: 2 or 3).

In alternative embodiments the amino acid sequence of the motoneuronotrophic factor peptide analog is at least 60% identical to 10 consecutive amino acid residues of SEQ ID NO: 4, at least 70% identical to 10 consecutive amino acid residues of SEQ ID NO: 4, at least 80% identical to 10 consecutive amino acid residues of SEQ ID NO: 4 and a least 90% identical to 10 consecutive amino acid residues of SEQ ID NO: 4 as determined by BLAST analysis.

To compare a polypeptide sequence with the corresponding SEQ ID NO: 1 fragment, a global alignment of the sequences can be performed using the BLAST programs publicly available through the National Center for Biotechnology Information (on the World Wide Web at ncbi.nlm.nih.gov). Prior to performing a global alignment, SEQ ID NO: 1 can be submitted to GenBank. Default parameters provided by the National Center for Biotechnology Information can be used for a global alignment.

10-mer

In one embodiment, there is provided a peptide having the following amino acid sequence: MLSAFSRYAR (SEQ ID NO: 4) corresponding to amino acid residues 13-22 of the SEQ ID NO: 1. The exemplary MNTF fragment may include most of the WMLSAFS domain as well as the entire FSRYAR domain. This fragment and variants thereof retain the ability of MNTF1 to exert neuro-protection, promote survival, maintenance and/or repair of motorneurons; or in certain instances, to differentiate stem cells into motor neurons.

The MNTF 10mer was at least as effective the full-length MNTF 33mer at stimulating differentiation of embryonic stems cells into motor neurons in vitro at concentrations as low as 0.01 µg/ml. In addition, the MNTF 10mer was nearly as effective as the MNTF 33mer at enhancing the survival of stem cell derived motor neurons. This portion of the MNTF-1 molecule will be referred to hereinafter as the "10mer."

6-mer and Analogs

In another embodiment, there is provided a peptide having the following amino acid sequence: FSRYAR (SEQ ID NO: 2) corresponding to amino acid residues 17-22 of SEQ ID NO: 1. This fragment and variants thereof retains the ability of MNTF1 to exert neuro-protection, promote survival, maintenance and/or repair of motorneurons (including stem cell derived motorneurons). This portion of the MNTF-1 molecule will be referred to hereinafter as the "6mer".

In certain embodiments, MNTF peptide analogs may include sequence or functional analogs of the 6-mer peptide.

7-mer

In another embodiment, there is provided a peptide having the following amino acid sequence: WMLSAFS (SEQ ID NO: 3) corresponding to amino acid residues 12-18 of SEQ ID NO: 1. This 7 amino acid fragment of MNTF1 overlaps the FS residues of the FSRYAR domain. This fragment and variants thereof retains the ability of MNTF1 to exert neuro-protection, promote survival, maintenance and/or repair of motorneurons (including stem cell derived motorneurons). This portion of the MNTF-1 molecule will be referred to hereinafter as the "7mer."

11-mer

In another embodiment, there is provided a peptide having the following amino acid sequence: FSRYARCLAE G (SEQ ID NO: 5) corresponding to amino acid residues 17-27 of SEQ ID NO: 1. The MNTF1 11-mer contains the FSRYAR domain. This fragment and variants thereof retains the ability of MNTF1 to exert neuro-protection, promote survival, maintenance and/or repair of motorneurons (including stem cell derived motorneurons). This portion of the MNTF-1 molecule will be referred to hereinafter as the "11mer."

21-mer

In another embodiment, there is provided a peptide having the following amino acid sequence: MLSAFSRYAR CLAEGHDGPT Q (SEQ ID NO: 6) corresponding to amino acid residues 13 to 33 of SEQ ID NO: 1. This MNTF121-mer contains most of the "WMLSAFS" domain as well as the entire FSRYAR domain. This fragment and variants thereof retains the ability of MNTF1 to exert neuro-protection, promote survival, maintenance and/or repair of motorneurons (including stem cell derived motorneurons). This portion of the MNTF-1 molecule will be referred to hereinafter as the "21mer."

MNTF Peptide Analogs

It is to be understood that the technology described herein includes use of peptide analogs in which one or more amino acids are substituted with other amino acids. In one alternative, the motoneuronotrophic factor peptide analog contains one or more conservative amino acid substitutions to a fragment of 6 to 32 consecutive amino acid residues of SEQ ID NO: 1.

An MNTF peptide analog can be an altered form of an MNTF1 peptide providing generally of course that the essential activity of the peptide remains substantially unchanged. As used herein, the term "altered form" refers to a peptide that has been treated to change its naturally occurring structure. An altered form can be prepared, for example, by covalent modification of an MNTF1 peptide fragment, by crosslinking MNTF1 peptide fragment to an insoluble support matrix, or by crosslinking MNTF1 peptide fragment to a carrier protein.

An MNTF1 peptide analog can be a peptide fragment that is antigenically related to an MNTF1 peptide fragment. Two peptides, which are antigenically related display immunological cross-reactivity. For example, antibodies to the first peptide also recognize the second peptide.

An MNTF1 peptide analog can be a fusion protein containing a MNTF1 peptide fragment attached to a heterologous protein. A heterologous protein has an amino acid sequence not substantially similar to the MNTF1 peptide fragment. The heterologous protein can be fused to the N-terminus or C-terminus of the MNTF1 peptide fragment. Fusion proteins can include, but are not limited to, poly-His fusions, MYC-tagged fusions, Ig fusions and enzymatic fusion proteins, for example beta-galactosidase fusions. Such fusion proteins, particularly poly-His fusions, can facilitate the purification of recombinant MNTF1 peptide fragments.

Peptidomimetics of MNTF peptide(s) are also within the scope of the technology described herein, and can act as drugs for the modulation of neuronal cell viability and growth by, for example, blocking the function of proteins comprising the WMLSAFS, FSRYAR, or any other sequence or functional domain(s) as described in SEQ ID NOs: 1-142. Peptidomimetics are commonly understood in the pharmaceutical industry to include non-peptide drugs having properties analogous to those of the mimicked peptide. The principles and practices of peptidomimetic design are known in the art and are described, for example, in Fauchere J., $Adv.$ $Drug$ $Res.$ 15: 29 (1986); and Evans et al., $J.$ $Med.$ $Chem.$ 30: 1229 (1987).

Peptidomimetics which bear structural similarity to therapeutically useful peptides may be used to produce an equivalent therapeutic or prophylactic effect. Typically, such peptidomimetics have one or more peptide linkages optionally replaced by a linkage, which may convert desirable properties such as resistance to chemical breakdown in vivo. Such linkages may include —$CH_2NH$—, —$CH_2S$—, —$CH_2$—$CH_2$—, —$CH$=$CH$—, —$COCH_2$—, —$CH(OH)CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

The rational design of WMLSAFS, FSRYAR, or other analogous domain mimetics or binding molecules, based on modeled (or experimentally determined) peptide structure, may be carried out by those of skill, using known methods of rational drug design. The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

Methods of Making

It is understood that an MNTF peptide composition of the present disclosure may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an MNTF peptide described herein in an in vitro translation system or in a living cell. The MNTF peptide of the composition can be isolated and extensively dialyzed to remove one or more undesired small molecular weight molecules and/or lyophilized for more ready formulation into a desired vehicle. It is further understood that additional amino acids, mutations, chemical modification and such like, if any, that are made in a MNTF peptide component should not substantially interfere with receptor recognition of the MNTF docking sequence.

A peptide or polypeptide corresponding to one or more fragments of MNTF1 should generally be at least six amino acid residues in length, and may contain up to about 7, about 8, about 9, about 10, about 11, about 12, about 13, about 15, about 20 or about 30 residues or so. A peptide sequence may be synthesized by methods known to those of ordinary skill in the art, such as, for example, peptide synthesis using automated peptide synthesis machines, such as those available from Applied Biosystems (Foster City, Calif.). The technology described herein includes synthesis and use of cyclic peptides derived from SEQ ID NOs: 1-142.

Covalent modifications can be introduced into a peptide by reacting targeted amino acid residues with an organic derivatizing agent that is capable of reacting with selected side chains or terminal residues. Covalent modification of polypeptides using organic derivatizing agents is well known to those of skill in the art. For example, cysteinyl residues can be reacted with α-haloacetates (and corresponding amines), such as chloroacetic acid or chloroacetamide, to give carboxymethyl or carboxyamidomethyl derivatives. Histidyl residues can be derivatized by reaction with diethylpyrocarbonate at pH 5.5-7.0, or with para-bromophenacyl bromide at pH 6 in 1 M sodium cacodylate. Lysinyl and amino terminal residues can be reacted with succinic or other carboxylic acid anhydrides. Arginyl residues can be modified by reaction with one or several conventional reagents, among them phenylglyoxal, 2,3-butanedione, 1,2-cyclohexanedione, and ninhydrin. Spectral labels can be introduced into tyrosyl residues by reaction with aromatic diazonium compounds or tetranitromethane; most commonly, N-acetylimidizol and tetranitromethane are used to form O-acetyl tyrosyl species and 3-nitro derivatives, respectively. Carboxyl side groups (aspartyl or glutamyl) can be selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues can be deamidated to the corresponding glutamyl and aspartyl residues. Other modifications include hydroxylation of proline and lysine, phosphorylation of hydroxy groups of seryl or threonyl residues, methylation of the α-amino groups of lysine, arginine, and histidine side chains (T. E. Creighton, 1983, Proteins: Structure and Molecule Properties, W.H. Freeman & Co., San Francisco, pp. 79-86), acetylation of the N-terminal amine, and, in some instances, amidation of the C-terminal carboxyl groups.

The MNTF peptide analogs described herein can be used in assays and kits for assays, either in the free form or linked to a carrier molecule such as a protein or a solid particle, as well as modified peptides linked to a label or tracer e.g. biotin or fluorescein isothiocyanate.

Crosslinking of MNTF1 peptide fragment to a water-insoluble support matrix can be performed with bifunctional agents well known in the art including 1,1 bis(diazoacetyl) 2 phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Bifunctional agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates can be employed for protein immobilization.

Crosslinking of an MNTF1 peptide fragment to a second protein, including a second MNTF1 peptide fragment, can be performed using the bifunctional reagents described herein. In another alternative, there is inserted a spacer, for example a dithiol group or a diamino group or multiples of amino acid residues, e.g. glycine. The spacer may also be a homo- or hetero-bifunctional crosslinker, for example the heterobifunctional crosslinker N-(4-carboxy-cyclohexyl-methyl)-maleimide.

Longer peptides or polypeptides, e.g a fusion protein, can be produced by standard recombinant DNA techniques. For example, a DNA fragment encoding a MNTF1 peptide fragment can be cloned in a commercially available expression vector that already contains a heterologous protein, with the result being MNTF1 peptide fragment fused in-frame to the heterologous protein.

In certain embodiments, a nucleic acid encoding an MNTF1 peptide and/or a component described herein may be used, for example, to produce a peptide in vitro or in vivo for the various compositions and methods described herein. For example, in certain embodiments, a nucleic acid encoding an MNTF1 peptide is a component of, for example, a vector in a recombinant cell. The nucleic acid may be expressed to produce a peptide or polypeptide comprising an MNTF1 peptide sequence. The peptide or polypeptide may be secreted from the cell, or as part of or within the cell.

Compound Screening

In another embodiment, compounds which alter the level of expression of a MNTF peptide or a protein involved in the intracellular signal transduction pathway of a MNTF peptide are identified. In certain embodiments, these compounds are targeted for the treatment of various neural disorders described herein.

Agonist and antagonists of neuroprotection can be distinguished, and the efficacy of the compound can be assessed, by subsequent testing with neuronal cells described herein and known in the art.

Compounds identified by the screening procedures described herein can further be distinguished, and the efficacy of the compound can be assessed, based upon their ability to treat neuronal disorders in art accepted animal cell culture disease and disorder model systems.

In many drug screening assays which test libraries of compounds and natural extracts, high throughput assays are desirable in order to maximize the number of compounds surveyed in a given period of time. Assays which are performed in cell-free systems, such as may be derived with purified or partially purified proteins, are often used as "primary" screens in that they can be generated to permit rapid development and relatively easy detection of an alteration in a molecular target which is mediated by a test compound. Further, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Thus in another aspect, a method of identifying a compound useful for promoting the growth or survival of motorneurons is provided. In one embodiment, the method comprises the steps of i) preparing a sample comprising a candidate compound, ii) contacting a cell with said sample, iii) determining whether the expression or activity of a compound involved in signal transduction pathway is modulated, and iv) determining whether the sample is capable of promoting the growth or survival of motorneurons. In certain embodiments, the method further comprises determining whether a sample containing a candidate compound stimulates the autophosphorylation of Tyr972 and Tyr1162/1163 of the insulin receptor in vitro or in vivo. In other embodiments, the method further comprises determining whether a sample containing a candidate compound regulates a MNTF signal transduction pathway. In other embodiments, the method further comprises determining whether a sample containing a candidate compound modulates the expression or activity of one or more proteins selected from a insulin receptor, IGF-1 receptor, IGF-2 receptor, Shh, Akt, Bad (bcl-2 antagonist of cell death), PI(3,4,5)P3-dependent kinase 1 (PDK1), Bax, p53 gene product, pp60-Src, JAK2, nitric oxide synthases (NOS), glycogen synthase kinase 3 (GSK), caspase, PI3 kinase (phosphatidylinositol 3-kinase), and Ras. In other embodiments, the method further comprises determining whether a sample containing a candidate compound is regulated by a MNTF analog, or alternatively regulated a MNTF analog (e.g. activity, expression, etc.). In another aspect, the technology described herein includes methods of promoting the growth or survival of a motoneuron or for the treatment of a neuronal disorder by administering a compound identified by the screening procedures described herein.

In an exemplary screening assay, the compound of interest is contacted with a mixture including a MNTF binding protein (e.g., a cell expressing a MNTF peptide receptor) and a MNTF peptide under conditions in which it is ordinarily capable of binding a MNTF peptide. To the mixture is then added a composition containing a test compound. Detection and quantification of receptor/MNTF peptide complexes provides a means for determining the test compound's efficacy at inhibiting (or potentiating) complex formation between the receptor protein and the MNTF peptide. A control assay can also be performed to provide a baseline for comparison, in which isolated and purified MNTF peptide is added to the receptor protein and the formation of receptor/MNTF peptide complex is quantitated in the absence of the test compound.

Complex formation between the MNTF peptide and a MNTF peptide may be detected by a variety of techniques. For instance, modulation of the formation of complexes can be quantitated using, for example, detectably labeled proteins such as radiolabeled, fluorescently labeled, or enzymatically labeled MNTF peptides, by immunoassay, or by chromatographic detection. For cell-free assays, it will typically be desirable to immobilize either the MNTF peptide or the MNTF peptide binding protein to facilitate separation of receptor/MNTF peptide complexes from uncomplexed forms of one of the proteins, as well as to accommodate automation of the assay. For example, a fusion protein can be provided which adds a domain that allows the protein to be bound to a matrix. For example, glutathione-S-transferase/receptor (GST/receptor) fusion proteins can be adsorbed onto glutathione Sepharose beads (Sigma Chemical, St. Louis, Mo.) or glutathione derivatized microtiter plates, which are then combined with the MNTF peptide, e.g., an $^{35}$S-labeled MNTF peptide, and the test compound and incubated under conditions conducive to complex formation, e.g., at physiological conditions for salt and pH, though slightly more stringent conditions may be desired. Following incubation, the beads are washed to remove any unbound MNTF peptide, and the matrix bead-bound radiolabel determined directly (e.g., beads placed in scintillant), or in the supernatant after the receptor/hedgehog complexes are dissociated. Alternatively, the complexes can be dissociated from the bead, separated by SDS-PAGE gel, and the level of MNTF peptide found in the bead fraction quantitated from the gel using standard electrophoretic techniques.

Other techniques for immobilizing proteins on matrices are also available for use in the subject assay. For instance, soluble portions of the MNTF peptide protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the MNTF peptide but which do not interfere with hedgehog binding can be derivatized to the wells of the plate, and the receptor trapped in the wells by antibody conjugation. As above, preparations of a MNTF peptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the MNTF peptide, or which are reactive with the receptor protein and compete for binding with the MNTF peptide; as well as enzyme-linked assays which rely on detecting an enzymatic activity associated with the MNTF peptide. In the instance of the latter, the enzyme can be chemically conjugated or provided as a fusion protein with the MNTF peptide. To illustrate, the MNTF peptide can be chemically cross-linked or genetically fused with alkaline phosphatase, and the amount of MNTF peptide trapped in the complex can be assessed with a chromogenic substrate of the enzyme, e.g., paranitrophenylphosphate. Likewise, a fusion protein comprising the MNTF peptide and glutathione-S-transferase can be provided, and complex formation quantitated by detecting the GST activity using 1-chloro-2,4-dinitrobenzene (Habig et al., *J Biol Chem,* 249:7130 (1974)). For immunodetection for quantitating one of the proteins trapped in the complex, antibodies against the protein, such as the anti-MNTF peptide antibodies can be used. Alternatively, the protein to be detected in the complex can be "epitope tagged" in the form of a fusion protein which includes, in addition to the MNTF peptide or MNTF peptide sequence, a second polypeptide for which antibodies are readily available (e.g., from commercial sources). For instance, the GST fusion proteins described above can also be used for quantification of binding using antibodies against the GST moiety. Other useful epitope tags include myc-epitopes (e.g., see Ellison et al., *J Biol Chem* 266:21150-21157 (1991)) which includes a 10-residue sequence from c-myc, as well as the pFLAG system (International Biotechnologies, Inc.) or the pEZZ-protein A system (Pharamacia, N.J.).

Compositions

Pharmaceutical compositions can include one or more of the MNTF peptide analogs disclosed herein together with a pharmaceutically acceptable diluent and/or carrier. Suitable carriers/diluents are well known in the art and include saline or other sterile aqueous media, optionally including additional components such as buffer salts and preservatives, or sugars, starches, salts or mixtures thereof.

Compositions containing MNTF peptides may be provided for use in any suitable form appropriate to the protocol of administration and/or the needs of a patient.

The technology described herein includes culture media that are useful for establishing and propagating stem cells, neural progenitor cells, differentiated neural cells and stem-cell derived motor neurons. The media are particularly suitable for the differentiation of stem cells and long-term culture of stem cell derived motor neurons.

The cell culture media are desirably supplemented with morphogens and/or growth factors, and optimized according to the individual cell type desired to be cultured. Such supplementation and optimization are within the ordinary skill in the art. In some embodiments, the cell culture medium may be supplemented with any or all of the following morphogens and/or growth factors at the following approximate levels (or within one significant digit): RA at 0.001-1 µM, Shh or Shh agonist, at 0.001-1 µM, and/or one or more MNTF peptide analogs at 0.01-250 µg/ml.

The pharmaceutical formulations described herein may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations include water and physiologically acceptable buffered saline solutions such as phosphate buffered saline solutions pH 7.0-8.0. Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation.

Compounds provided herein may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the peptide.

Pharmaceutical compositions are generally formulated for administered for a therapeutic purpose. Pharmaceutical compositions may also include one or more active ingredients such as interferons, antimicrobial agents, anti-inflammatory agents, anesthetics, and the like. Formulations for parenteral administration may include sterile aqueous solutions which may also contain buffers, liposomes, diluents and other suitable additives. Pharmaceutical compositions comprising the peptides provided herein may include penetration enhancers in order to enhance the alimentary delivery of the peptides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 8, 91-192 (1991); Muranishi, Critical Reviews in Therapeutic Drug Carrier Systems 7, 1-33 (1990)). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Lee et al., Critical Reviews in Therapeutic Drug Carrier Systems page 92 (1991); Muranishi, Critical Reviews in Therapeutic Drug Carrier Systems 7, 1 (1990); El-Hariri et al., J. Pharm. Pharmacol. 44, 651-654 (1992)).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al. McGraw-Hill, New York, N.Y., pages 934-935 (1996)). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems page 92 (1991); Muranishi, Critical Reviews in Therapeutic Drug Carrier Systems 7, 1-33 (1990); Buur et al., J. Control Rel. 14, 43-51 (1990)). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems page 92 (1991)); and perfluorochemical emulsions, such as FC-43 (Takahashi et al., J. Pharm. Pharmacol. 40, 252-257 (1988)). Non-surfactants include, for example, unsaturated cyclic ureas, 1-alkyl- and 1-alkenylazacyclo-alkanone derivatives (Lee et al., Critical Reviews in Therapeutic Drug Carrier Systems page 92 (1991)); and non-steroidal anti-inflammatory agents such as diclofenac sodium, indomethacin and phenylbutazone (Yamashita et al., J. Pharm. Pharmacol. 39, 621-626 (1987)).

Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition described herein, such as dyes, flavoring agents, preservatives, antioxidants, opacifiers, thickening agents and stabilizers. However, such materials, when added, should not unduly interfere with the biological activities of the components of the compositions provided herein.

Regardless of the method by which compounds are introduced into a patient, colloidal dispersion systems may be used as delivery vehicles to enhance the in vivo stability of the peptides and/or to target the peptides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:peptide complexes of uncharacterized structure. An example of a colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 6, 698-708 (1995)).

In certain embodiments, MNTF peptides and MNTF analogs can be incorporated into or used in conjunction with a biodistribution directing moiety, including one or more polymer, to direct the biodistribution of the MNTF peptide or MNTF analog or other compound provided herein to the proximity of the a desired target or to allow for continuous release of thereof. Active agents include, for example, compounds useful for increasing therapeutic efficacy, for optimizing biodistribution and bioavailability, for reducing tissue damage, for promoting healing, or for increasing patient comfort; exemplary active agents include vasoactive agents, anesthetics, therapeutic agents for ischemia, growth factors and cytokines. Alternatively, microparticulate or nanoparticulate polymeric bead dosage forms may be used in composition provided herein. Compounds provided herein may be used in combination with an active agent and encapsulated in a particulate dosage form with a number of ligand or anti-ligand molecules attached thereto.

In this manner, MNTF peptides and MNTF analogs, and other compounds provided here, alone or in combination with other active agents, are released at that site over time to provide a sustained therapeutic benefit. Sustained release dosage forms are also useful with regard to other active agents useful in the methods described herein, such as growth factors, cytokines, and the like. Release of the active agent from the particulate dosage forms can occur as a result of both diffusion and particulate matrix erosion. Biodegradation rate directly impacts active agent release kinetics.

In certain embodiments, controlled release parenteral formulations of MNTF peptides, MNTF analogs, and compounds described herein can be made as implants, oily injections, or as particulate systems. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Liposomes can be used for controlled release as well as drug targeting of entrapped drug.

In certain embodiments, the pharmaceutical composition described herein, including MNTF peptides and MNTF analogs, can be administered locally, topically, nasally, orally, gastrointestinally, intrabronchially, intravesically, intravaginally, into the uterus, subcutaneously, intramuscularly, periarticularly, intraarticularly, into the cerebrospinal fluid (ICSF), into the brain tissue (e.g. intracranial administration), into the spinal medulla, into wounds, intraperitoneally or intrapleurally, or systemically, e.g. intravenously, intraarterially, intraportally or into the organ directly.

A variety of catheters and delivery routes can be used to achieve intracoronary delivery, as is known in the art. For example, a variety of general-purpose catheters, as well as modified catheters, suitable for use as described herein are available from commercial suppliers such as Advanced Cardiovascular Systems (ACS), Target Therapeutics and Cordis. Also, where delivery to the myocardium is achieved by injection directly into a coronary artery, a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., Topol, E J (ed.), The Textbook of Interventional Cardiology, 2nd Ed. (W.B. Saunders Co. 1994); Rutherford, R B, Vascular Surgery, 3rd Ed. (W.B. Saunders Co. 1989); Wyngaarden J B et al. (eds.), The Cecil Textbook of Medicine, 19th Ed. (W. B. Saunders, 1992); and Sabiston, D, The Textbook of Surgery, 14th Ed. (W.B. Saunders Co. 1991)).

The compounds provided herein may be administered parentally. Certain compounds are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intracerebral, intravenous, subcutaneous, or transdermal administration. The formulation which is administered may contain such agents. Examples of these agents include cationic agents (for example calcium phosphate and DEAE-dextran) and lipofectants (for example Lipofectam™ and Transfectam™).

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated gloves, condoms, and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral administration may include sterile aqueous solutions which may also contain buffers, diluents and other suitable additives. In some cases it may be more effective to treat a patient with a peptide in conjunction with other traditional therapeutic modalities in order to increase the efficacy of a treatment regimen. As used herein, the term "treatment regimen" is meant to encompass therapeutic, palliative and prophylactic modalities.

Dosing can be dependent on a number of factors, including severity and responsiveness of the disease state to be treated, and with the course of treatment lasting from several days to several months, or until a cure is effected or a diminution of the disease state is achieved. Toxicity and therapeutic efficacy of compounds provided herein can be determined by standard pharmaceutical procedures in cell cultures or experimental animals. For example, for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are useful. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds should be within a range of circulating concentrations that include the $ED_{50}$ with little or no toxicity. The dosage may vary within this range depending upon the dosage form employed and the route of administration utilized. For any compound used as described herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Dosing schedules can be calculated from measurements of drug accumulation in the body of the patient. Dosages may vary depending on the relative potency of individual compounds, including MNTF peptides and MNTF analogs, and can generally be estimated based on EC50 s found to be effective in vitro and in in vivo animal models. One of skill in the art will recognize that dosages will vary depending on how and where an MNTF peptide is administered (e.g. in vitro, in vivo, topically, systemically, etc.).

For example, in one aspect, MNTF peptides and MNTF analogs may be administered to achieve from about 0.01 micrograms per ml (1 µg/mL) to about 1 mg per ml, from about 0.1 µg/mL to about 50 µg/mL, from about 0.1 µg/mL to about 150 µg/mL, from about 1 µg/mL to about 200 µg/mL, and from about 0.1 µg/mL to about 500 µg/mL, including any range within these ranges, final concentrations at a target site (e.g. in a cell culture of ES stem cells).

Alternative suitable dosage amounts may, for example, vary from about 0.1 ug up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides, polypeptides, and compounds provided herein will be specific to particular cells, conditions, and locations. In general, dosage generally ranges from 0.01 mg/kg to 1000 mg per kg of body weight, and more typically, for example, from 0.1 mg/kg to 300 mg per kg of body weight, and may be given once or more daily, weekly, monthly or yearly, or even once or more during a time span of 2 to 20 years. In certain embodiments, the dosage may be given from immediately post surgery to 24 hours, in another embodiment; the dosage is given from 2 hours and up to 24 hours. Long-acting compositions may be administered every 3 to 4 days, every week, or biweekly depending on the half-life and clearance rate of the particular formulation. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein a selected compound is administered in maintenance doses, ranging from 0.01 mg/kg to 100 mg per kg of body weight, once or more daily, to once every 20 years. In the treatment or prevention of certain conditions, an appropriate dosage level will generally be about 0.001 to 100 mg per kg patient body weight per day which can be administered in single or multiple doses. A suitable dosage level can be about 1 to about 40 mg/kg per day. In certain embodiments, compounds provided herein, including MNTF peptides and MNTF peptide analogs, are administered in an amount to achieve in vivo concentrations from about 1 micromolar to about 1 millimolar, from about 10 micromolar to about 500 micromolar, or from about 30 micromolar to about 300 micromolar, and from about 25 micromolar to about 300 micromolar final concentration over the damaged site, and including, about 25 micromolar, or about 160 micromolar, or about 300 micromolar final concentration over the damaged site, and still more typically between about 1 micromolar to about 100 micromolar.

In certain embodiments, dosage of 1, 5, 10, 20, 50, 100, 150, or 200 mg/kg, may be administered.

Compounds described herein can be used in diagnostics, therapeutics, prophylaxis, and as research reagents and in kits. Provision of means for detecting compounds of interest (e.g. MNTF peptides and MNTF analogs) can routinely be accomplished. Such provision may include enzyme conjugation, radiolabelling or any other suitable detection systems. Kits for detecting the presence or absence of compounds of interest may also be prepared.

As used herein, spinal cord injuries may include injuries resulting from a tumor, mechanical trauma, and chemical trauma. The same or similar methods are contemplated to restore motor function in a subject having amyotrophic lateral sclerosis, multiple sclerosis, or a spinal cord injury.

In certain embodiments, administering one of the MNTF analogs also provide a prophylactic function. Such administration has the effect of preserving motor function in a subject, or at risk of having, amyotrophic lateral sclerosis, multiple sclerosis, or a spinal cord injury.

In certain embodiments, MNTF analog administration preserves the integrity of the MNTF pathway.

Specifically, methods for treating (pre- or post-symptomatically) a spinal cord injury, a neurodegenerative disease, a stroke or cerebral ischemia, Huntington's disease, Parkinson's disease, Multiple Sclerosis, ALS, Alzheimer's, and a Diabetic Neuropathy comprise administering a MNTF peptide analog selected from the group consisting of SEQ ID NOs: 1-142.

In certain aspects, compositions and therapeutic treatment methods comprising administering to a subject a therapeutically effective amount of a MNTF analog protein as defined herein, upon injury to a neural pathway, or in anticipation of such injury, for a time and at a concentration sufficient to maintain the neural pathway, including repairing damaged pathways, or inhibiting additional damage thereto, are provided.

In another aspect, the technology described herein includes compositions and therapeutic treatment methods for maintaining neural pathways. Such treatment methods include administering to the subject, upon injury to a neural pathway or in anticipation of such injury, a compound that stimulates a therapeutically effective concentration of an endogenous MNTF.

Aspects and embodiments described herein provide methods for protecting neurons from the tissue destructive effects associated with the body's immune and inflammatory response to nerve injury.

In certain embodiments, methods, compositions and devices for stimulating cellular repair of damaged neurons and neural pathways, including regenerating damaged dendrites or axons, are provided.

In one aspect, the MNTF analogs described herein are useful in repairing damaged neural pathways of the peripheral nervous system. In particular, MNTFs are useful for repairing damaged neural pathways, including transected or otherwise damaged nerve fibers. Specifically, the MNTFs described herein are capable of stimulating complete axonal nerve regeneration, including vascularization and reformation of the myelin sheath. The MNTF can be provided to the site of injury in a biocompatible, bioresorbable carrier capable of maintaining the MNTF at the site and, where necessary, means for directing axonal growth from the proximal to the distal ends of a severed neuron. For example, means for directing axonal growth may be required where nerve regeneration is to be induced over an extended distance, such as greater than 10 mm. Many carriers capable of providing these functions are envisioned. For example, useful carriers include substantially insoluble materials or viscous solutions prepared as disclosed herein comprising laminin, hyaluronic acid or collagen, or other suitable synthetic, biocompatible polymeric materials such as polylactic, polyglycolic or polybutyric acids and/or copolymers thereof.

In certain embodiments, a MNTF analog is disposed in a nerve guidance channel which spans the distance of the damaged pathway. The channel acts both as a protective covering and a physical means for guiding growth of a neurite. Useful channels comprise a biocompatible membrane, which may be tubular in structure, having a dimension sufficient to span the gap in the nerve to be repaired, and having openings adapted to receive severed nerve ends. The membrane may be made of any biocompatible, nonirritating material, such as silicone or a biocompatible polymer, such as polyethylene or polyethylene vinyl acetate. The casing also may be composed of biocompatible, bioresorbable polymers, including, for example, collagen, hyaluronic acid, polylactic, polybutyric, and polyglycolic acids. In one embodiment, the outer surface of the channel is substantially impermeable.

In another aspect, MNTFs described herein are useful to protect against damage associated with the body's immune/inflammatory response to an initial injury to nerve tissue. Such a response may follow trauma to nerve tissue, caused, for example, by an autoimmune dysfunction, neoplastic lesion, infection, chemical or mechanical trauma, disease, by interruption of blood flow to the neurons or glial cells, or by other trauma to the nerve or surrounding material. For example, the primary damage resulting from hypoxia or ischemia-reperfusion following occlusion of a neural blood supply, as in an embolic stroke, is believed to be immunologically associated. In addition, at least part of the damage associated with a number of primary brain tumors also appears to be immunologically related. Application of a MNTF analog, either directly or systemically alleviate and/or inhibit the immunologically related response to a neural injury.

In another embodiment, the technology described herein encompasses use of biologically active species (phylogenetic) variants of any of the MNTF proteins recited herein, including conservative amino acid sequence variants, proteins encoded by degenerate nucleotide sequence variants, and MNTF proteins sharing the conserved MNTF domains and encoded by a DNA competent to hybridize under standard stringency conditions to a DNA encoding a MNTF protein disclosed herein, including, without limitation.

The compounds described herein may also be used for research purposes. Thus, the specific hybridization exhibited by the peptides may be used for assays, purifications, cellular product preparations and in other methodologies which may be appreciated by persons of ordinary skill in the art.

Technical and scientific terms used herein have meanings commonly understood by one of ordinary skill in the art to which the present disclosure pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., Molecular Cloning: A Laboratory Manual, 2d Ed., Cold Spring Harbor Laboratory Press, Plainview, N.Y. (1989) and Molecular Cloning: A Laboratory Manual, third edition (Sambrook and Russel, 2001), jointly and individually referred to herein as "Sambrook"; McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993); Teratocarcinomas and embryonic stem cells: A practical approach (E. J. Robertson, ed., IRL Press Ltd. (1987); Guide to Techniques in Mouse Development (P. M. Wasserman et al. eds., Academic Press (1993); Embryonic Stem Cell Differentiation in vitro (M. V. Wiles, *Meth. Enzymol.* 225:900 (1993); Properties and uses of Embryonic Stem Cells: Prospects for Application to Human Biology and Gene Therapy (P. D. Rathjen et al., *Reprod. Fertil. Dev.,* 10:31 (1998)); CNS Regeneration: Basic Science and Clinical Advances, M. H. Tuszynski & J. H. Kordower, eds., Academic Press, (1999).

Certain techniques that may be useful in the practice of the technology disclosed herein are described in various patents and patent applications, including U.S. Pat. No. 5,851,832, which reports multipotent neural stem cells obtained from brain tissue, U.S. Pat. No. 5,766,948 which reports producing neuroblasts from newborn cerebral hemispheres, U.S. Pat. Nos. 5,654,183 and 5,849,553 which report the use of mammalian neural crest stem cells, U.S. Pat. No. 6,040,180 which reports in vitro generation of differentiated neurons from cultures of mammalian multipotential CNS stem cells, WO 98/50526 and WO 99/01159 which report generation and isolation of neuroepithelial stem cells, oligodendrocyte-astrocyte precursors, and lineage-restricted neuronal precursors, and U.S. Pat. No. 5,968,829 which reports neural stem cells obtained from embryonic forebrain and cultured with a medium comprising glucose, transferrin, insulin, selenium, progesterone, and several other growth factors.

Any suitable materials and/or methods known to those of skill can be utilized in carrying out the technology described herein; however, non-limiting examples of materials and/or methods are described herein.

The technology disclosed herein may be appreciated in certain aspects with reference to the following examples, offered by way of illustration, not by way of limitation. Materials, reagents and the like to which reference is made in the following examples are obtainable from commercial sources, unless otherwise noted.

Certain examples described below contained citation references which are provided herein:

Chau R M W, Ren F, Huang W, Jen L S. Muscle neurotrophic factors specific for anterior horn motoneurons of rat spinal cord. Recent Advances in Cell. And Mol. Biol. 1992, 5:89-94.

Copeland R L Jr, Leggett Y A, Kanaan Y M, Taylor R E, Tizabi Y. Neuroprotective effects of nicotine against salsolinol-induced cytotoxicity: implications for Parkinson's disease. Neurotox Res. 2005 November; 8(3-4):289-93.

KM Biotech. Published PCT Patent Application: WO 98/13492, 1998.

Maruyama W, Yi H, Takahashi T, Shimazu S, Ohde H, Yoneda F, Iwasa K, Naoi M. Neuroprotective function of R-(−)-1-(benzofuran-2-yl)-2-propylaminopentane, [R-(−)-BPAP], against apoptosis induced by N-methyl(R)salsolinol, an endogenous dopaminergic neurotoxin, in human dopaminergic neuroblastoma SH-SY5Y cells. Life Sci. 2004 May 21; 75(1):107-17.

Nussbaum D, Ash D, Jabs E, Brushart T. Mononeuron trophic factor (MNTF) From Gene to Function. Soc. For Neuroscience, New Orleans, La., 2003.

Shavali S, Ren J, Ebadi M. Insulin-like growth factor-1 protects human dopaminergic SH-SY5Y cells from salsolinol-induced toxicity. Neurosci Lett. 2003 Apr. 10; 340(2):79-82.

Wang A M, Chau R M W, Chow S P, Zhang Z Y, Li Z M. Effects of myogenic 22 and 35 kD neurotrophic factors on axonal regeneration in free peripheral autografts into rat spinal cord. 1995, 5(6):248-252.

Dubal D B, Zhu H, Yu J, Rau S W, Shughrue P J, Merchenthaler I, Kindy M S, Wise P M. Estrogen receptor alpha, not beta, is a critical link in estradiol-mediated protection against brain injury. Proc Natl Acad Sci USA. 2001, 98:1952-1957.

Ellsworth J L, Garcia R, Yu J, Kindy M S. Time window of fibroblast growth factor-18-mediated neuroprotection after occlusion of the middle cerebral artery in rats. J Cereb Blood Flow Metab. 2004, 24:114-123.

Ellsworth J L, Garcia R, Yu J, Kindy M S. Fibroblast growth factor-18 reduced infarct volumes and behavioral deficits after transient occlusion of the middle cerebral artery in rats. Stroke. 2003, 34:1507-1512.

Gary D S, Bruce-Keller A J, Kindy M S, Mattson M P. Ischemic and excitotoxic brain injury is enhanced in mice lacking the p55 tumor necrosis factor receptor. J Cereb Blood Flow Metab. 1998, 18:1283-1287.

KM Biotech. International Patent WO 98/13492, 1998.

Mattson M P, Zhu H, Yu J, Kindy M S. Presenilin-1 mutation increases neuronal vulnerability to focal ischemia in vivo and to hypoxia and glucose deprivation in cell culture: involvement of perturbed calcium homeostasis. J Neurosci. 2000, 20:1358-1364.

Di X, Huang W. Localization and morphometric study on motoneuronotrophic factor 1 and its receptor in developing chorionic villi of human placenta. Acta Anatomica Sinica, 1998, 29:86-89.

Xinyu D, Weiquan H. Localization and morphometric study on motoneuronotrophic factor 1 and its receptor in developing chorionic villi of human placenta. Acta Anatomica Sinica, 1998, 29:86-89.

As used herein, it is contemplated that the efficacy of the MNTF peptides and sequence and/or functional analogs thereof may be determined by substantially similar and/or identical protocols as described in the following examples. In addition, it is contemplated that the efficacy of any of the MNTF peptide analogs as set forth in SEQ ID NOs: 1-142, and variants thereof, may be determined according to the experimental conditions as set forth herein.

As used herein, exemplary MNTF peptide analogs GM6, GM602, GM603, GM604, MNTF 6mer all refer to the MNTF 6-mer containing the sequence FSRYAR (SEQ ID NO: 2).

Example 1

Testing of MNTF Blood Brain Barrier Penetration

Abbreviations/Terminology for this Example.

"MNTF" means Motorneuron trophic factor; or peptide analogs thereof.

"GM6" and "6mer" mean exemplary 6 amino acid peptide analog of MNTF; i.e., FSRYAR (SEQ ID NO: 2).

"BBB" means blood-brain barrier.

"Genervon" and "GB" mean Genervon Biopharmaceuticals, LLC.

"I.V." means intravenous.

"Anti-6mer antibody" means anti-GM6 antibody.

"NTS" means Neurological Testing Service, which is a contract research organization.

Test the ability of the synthetic 6 amino acid analog (GM6; FSRYAR) of Motoneurontrophic factor (MNTF) to cross the blood brain barrier and gain access to the brain.

GM6 is a synthesized 6 amino acid peptide MNTF analog. GM6 was provided as a solid and formulation was prepared by NTS (solution stored at 4° C.).

MNTF has been tested in various rat nerve systems, including the peripheral sciatic nerve, the peripheral musculocutaneous nerve, the cranial facial nerve, the cranial hypoglossal nerve, and the portion of the spinal cord that controls muscles in the neck, chest and upper limbs. In the spinal cord model, MNTF was applied on the nerve graft in a hemi-section spinal cord in rat. MNTF reduced inflammation, limited degeneration and enhanced regeneration of the grafted nerves. A number of studies have demonstrated the efficacy of the synthesized MNTF or GM6 in well-established rat peripheral nerve model systems for trophic and tropic effects when MNTF or GM6 is applied directly on the nerve. In addition, MNTF has been shown to promote the regeneration and survival of motoneurons.

Additionally, the wobbler mouse model with double recessive genes was chosen as a proxy to investigate the capacity of MNTF to rescue motoneurons from the genetic defect that leads to motoneuron degenerative disease in this strain. In preliminary experiments, one dose of MNTF given intramuscular at the age of six weeks slowed the development of motoneuron disease. It significantly increased the survival of the untreated wobbler mice from 9 to 12 weeks to 28 to 63 weeks in the treated wobbler mice.

The effect of MNTF and GM6 on various animal systems was assessed. No safety problems were identified in studies with over 1000 Sprague Dawley rats and 15 of both wobbler mice and its normal littermates. Because of the potential role MNTF plays in the neuronal protection, inflammation and neuroregeneration, pharmaceutical compositions comprising MNTF and peptide analog thereof was evaluated for the treatment of neurological diseases. A major obstacle to treat Central Nervous System diseases and disorders is the difficulty of delivering the drug to the Central Nervous System. Determining the bioavailability of the drug and the effect on various neurological disorders was conducted to assess the drug's therapeutic potential.

Assessment of the availability of gm6 to the brain via intravenous injection.

Methods and Materials

Study Design

C57BL6 mice were injected with GM6 at the indicated doses and examined for GM6 in the brain. Half of the brain was taken for immunocytochemical analysis for GM6, the other half (brain) was frozen for ELISA analysis.

In Vivo Methods

Male C57BL/6 (Jackson Laboratory) mice weighing approximately 25 grams each were given free access to food and water before and during the experiment. Animals were acclimated for 1 week prior to experimentation. The animals were bolus i.v. dosed via tail vein with vehicle or GM6 at 0.2 or 2 mg/kg. Formulation of GM6 was performed as a stock solution by reconstituting GM6 with 100% saline solution that was stored at 4° C. Vehicle control received saline solution.

Immunohistochemical Analysis

Tissue sections were deparaffinized and washed in Tris buffered saline (TBS) pH 7.4 and blocked in the appropriate serum (goat). Sections were blocked overnight at 4° C. and then subjected to primary antibody (anti-6-mer antibody) overnight at 4° C. Sections were washed in TBS and secondary antibody was added and incubated for 1 hour at room temperature. After washing the sections were incubated as instructed in the Vector ABC Elite kit and stained with diaminobenzoic acid (DAB). The reactions were stopped in water and cover slipped after treatment to xylene. The immunocytochemical stained area in each section was determined with a computer-assisted image analysis system, consisting of a Power Macintosh computer equipped with a Quick Capture frame grabber card, Hitachi CCD camera mounted on an Olympus microscope and camera stand. NIH Image Analysis Software, v. 1.55 was used. The images were captured and the total area of GM6 peptide was determined over the ten sections. A single operator blinded to treatment status performed all measurements.

ELISA Analysis

To measure GM6 levels in samples using the competitive ELISA kit. Affinity purified rabbit anti-6Mer was coated on ELISA plate at 10 ug/ml in coating buffer. 6Mer-biotin was used at 1 uM (final dilution) in the assay. The known concentrations of GM6 (competitor) were used as reference standards starting from 80 uM and titrating 2-fold down 0.625 uM in the test for establishing standard curve. Concentration of tested samples was estimated from their OD450 observation based on the standard curve.

The brain tissue was prepared in cell lysis buffer containing 100 mM Tris HCl, pH 7.0, containing 2% BSA, 1 M NaCl, 4 mM EDTA, 2% Triton X-100, 0.1% sodium azide and protease inhibitors (Complete™, Mini, Boehringer Mannheim). Homogenates were prepared in 10 volumes of buffer to tissue wet weight. The homogenates were centrifuged for 30 minutes at 14,000×g. The resulting supernatant was used for ELISA with the appropriate volume adjustment.

For the assay, the anti-6Mer pAb was diluted to 10 ug/ml in ELISA coating buffer. The 96-well micro-titer plates were coated with 100 ul/well of the diluted pAb. The plates were covered and kept refrigerated overnight. Next day, the plates were blocked with 200 ul/well TBS with 3% BSA, and kept at RT for 60 min. The plates were washed 3× with TBST (TBS+ 0.05% Tween 20). For each plate, 10 ml 1 uM 6Mer-biotin and make 1 ml standard mix was prepared: 1 uM 6Mer-biotin with 80 uM 6Mer. For each plate, lanes 1 and 2 were used for the standard curve. 1 uM 6Mer-biotin (100 µl) was added to all wells except A1 and A2 and 200 ul/well of standard mix was added to A1 and A2. A serial 2-fold dilution from wells A1 and A2 down to wells H1 and H2 was performed by taking out 100 ul sample from each well and mix it with next well—pipetting up and down at least 8 times. The extra 100 ul at the final wells (H1 and H2) was discarded. Test samples (brain homogenate) was diluted in Ab dilution buffer and mixed at a 1:50 with the 1 uM 6Mer-biotin. The plate was mixed on a shaker at 400 rpm for 2 hours at RT. The samples were washed 6× with TBST. Streptavidin-HRP (10 ml per plate) solution was prepared by diluting Streptavidin-HRP to 1:2000 in Ab dilution buffer. The plate was mixed on the shaker for another 1 hour at RT. The samples were wash 8× with TBST. 50 ul/well substrate (TMBS, Genetel) was added and developed for 5 minutes. The reaction was stopped with 50 ul 1M HCl. and read OD450 immediately.

Statistical Analysis

The results are expressed as the mean±standard deviation (SD). The significance of difference in the ELISA and immunohistological data was analyzed using a t-test.

Exclusion of Animals from the Study

Animals will be excluded from the study based upon several criteria:

Animals that died prior to completion of study (at any point).

Animals developed severe complications following administration of test articles.

Treatment Groups

All groups were subjected to GM6 or were controls. Animals (30 animals) were subjected to bolus i.v. dosing by tail vein of vehicle or MNTF at the indicated doses.

TABLE

| Mouse BBB model: | | | |
|---|---|---|---|
| Group C57BL/6 mice | Compound | Dose (mg/kg) | Route |
| 1 (n = 10 mice) | Vehicle | 0 | IV |
| 2 (n = 10 mice) | GM6 | 0.2 mg/kg | IV |
| 3 (n = 10 mice) | GM6 | 2 mg/kg | IV |

Endpoints

GM6 in the brain.

All test groups have been provided to NTS; GM6 was provided as a solid material to NTS. All animals in the test groups were dosed as indicated above.

At the end of the study, ½ of the brain was taken for immunocytochemical analysis for GM6. The other ½ was taken for ELISA analysis for GM6.

Results

MNTF in mice. Blood Brain Barrier Study

The relative availability of GM6 in the brain was assessed. Data from mice (wild type) that were i.v. administered with vehicle or GM6.

Immunocytochemical Analysis:

GM6: After administration of MNTF, brains were taken and examined for immunocytochemical analysis for GM6 using an anti-6mer antibody. No immunoreactivity was detected in the tissue of any of the animals compared to control animals.

ELISA Analysis:

To measure GM6 levels in brain samples using the competitive ELISA kit samples were prepared as described above and subjected to ELISA. As shown in FIG. 1 and Table 4, MNTF GM6 was detected in the brain using the ELISA assay. The ELISA detected basal level of endogenous GM6 in the brain (0.4 µM). In the animals injected with 0.2 mg/kg of GM6 a 400% increase in GM6 was detected (1.760 µM) whereas injection of 2 mg/kg of GM6 gave rise to a 3000% increase in GM6 in the brain after 4 hours (12.92 µM). These data suggest that intravenous injection of GM6 will allow for distribution of the peptide in the brain.

TABLE 4

MNTF in the brain (I.V injections). (shown in FIG. 1)

| Compound | Mouse strain | ELISA MNTF (µM) | P value (increase) |
|---|---|---|---|
| Vehicle | WT | 0.4050 ± 0.3027 | 0 |
| MNTF 0.2 mg/kg | WT | 1.760 ± 0.9834 | 0.0001 (434%) |
| MNTF 2 mg/kg | WT | 12.92 ± 4.635 | 0.0001 (3190%) |

Mortality: There were no deaths in this study.

Based on these data, MNTF is a trophic factor that can provide protection from neurological diseases and allow for regeneration of neuronal tissue following injury or grafting. The studies performed here demonstrate the ability of the 6 amino acid analog of MNTF (GM6) to cross the blood brain barrier in an effective and efficient way. Intravenous administration of GM6 at 0.2 and 2 mg/kg single bolus dose demonstrated and dose dependent increase in GM6 levels in the brain. This indicated that GM6 has access to the brain via intravenous administration and can be used in various models of disease to determine the beneficial effects.

When administered intravenously, GM6 was found to be present in the brain after 4 hours. The level of GM6 in the brain was dose dependent and indicates that GM6 has access to the brain via intravenous administration.

Example 2

Stroke

MNTF Treatment of Stroke in MCAO Model

MNTF peptide analog GM602 (SEQ ID NO: 2, FSRYAR) was tested for efficacy in the middle cerebral artery occlusion (MCAO) mouse model. In order to determine the efficacy of GM602 in the MCAO mouse model, mice were subjected to 1 hour of ischemia and 24 hours of reperfusion. Mice were injected intravenously bolus via tail vein with GM602 at several doses immediately after the start of reperfusion and examined for changes in cerebral blood flow (CBF), heart rate (HR), blood pressure (BP), pO2, pCO2, pH, neurological deficits (ND) and infarct volume (IFV). Intravenous (IV) administration of GM602 (1 or 5 mg/kg) single dose was examined. Administration of GM602 demonstrated no changes in HR, BP, pO2, pCO2, or pH. A significant increase over the control group in CBF after reperfusion was observed with GM602 administration, which helps to mitigate the ischemic effect caused by the blockage of blood flow. Dose dependent changes were detected in ND and IFV after GM602 injection. GM602 at both 1 and 5 mg/kg showed a significant protection from infarct damage, which translated to preservation of neurological deficits. These data suggest that GM602 is neuroprotective to the brain following IV injection in the mouse model of MCAO.

Abbreviations/Terminology for this Example.

"MNTF" means Motoneuronotrophic factor.

"MNTF6mer" means 6-amino acid peptide analog of MNTF, e.g., FSRYAR.

"GM602" means 6-amino acid peptide analog of MNTF for Stroke.

"GM602 (1)" means GM602 dose of 1 mg/kg.

"GM602 (5)" means GM602 dose of 5 mg/kg.

"MCAO" means middle cerebral artery occlusion.

"GB" means Genervon Biopharmaceuticals LLC.

"IV" means intravenous.

"CBF" means cerebral blood flow.

"HR" means heart rate.

"BP" means blood pressure.

"ND" means neurological deficits.

"IFV" means infarct volume.

MNTF is an endogenous neurotrophin with a specific human chromosome location discovered by function. MNTF is highly specific for the human nervous system and it is expressed rapidly during the first trimester of human fetus development of the complete nervous system, pealing at week nine (Di and Huang, 1998). MNTF is a neuro-signaling molecule that binds perfectly on very specific receptors. The specific functions of MNTF, as demonstrated in animal and in vitro studies, are embryonic stem cell differentiation into motoneurons, motoneuron maintenance and survival, motor axon regeneration with guidance, and re-enervation of target muscles and organs (Chau et al., 1992; Nussbaum et al., 2003). When the Central Nervous System (CNS) and Peripheral Nervous System (PNS) are under attack caused by diseases, disorders or injuries, MNTF creates a protective and permissive environment for nerve regeneration and repair that are neuroprotective, anti-apoptosis, anti-oxidation, anti-inflammation, and anti-scar.

A number of studies have demonstrated the efficacy of the MNTF in various rat nerve systems, including the peripheral sciatic nerve, the peripheral musculocutaneous nerve, the cranial facial nerve, the cranial hypoglossal nerve, and the portion of the spinal cord that controls muscles in the neck, chest and upper limbs (Wang et al., 1995). In the hemisectioned rat spinal cord model, MNTF reduced inflammation, limited degeneration and enhanced regeneration of the grafted nerves (KM Biotech PCT, 1998). A number of studies have demonstrated the trophic and tropic efficacy of the synthesized MNTF or MNTF 6mer (FSRYAR; SEQ ID NO: 2) in a well-established rat peripheral nerve model system (Nussbaum et al, 2003). In addition, MNTF has been shown to promote the regeneration and survival of motoneurons (KM Biotech PCT, 1998). Furthermore, the wobbler mice (NIH) with double recessive genes given one dose of 35 ng MNTF at the age of six weeks slowed the neurodegenerative genetic disease in this strain. (KM Biotech PCT, 1998).

A sequence analog of 6 amino acids (FSRYAR) to one of the active sites of MNTF was investigated as a drug candidate with MNTF activity. Independent research groups using their own established assays and protocols conducted the following CNS and PNS experiments: 1. The MNTF6mer analog has been shown to be able to penetrate the Blood Brain Barrier and enter the brain by IV injection. 2. L-2-hydroxyglutaric acid (LGA) induces oxidative stress and apoptosis in the nervous system. In a zebrafish bioassay MNTF6mer protected LGA-induced apoptosis in the CNS and reduced apoptosis by 85% in the midbrain. 3. In a rat sciatic nerve transection with a 8 mm gap study, MNTF treated animals have significant improvement of motoneuron regeneration in a dose response manner ($p<0.0002$ at the optimal dose) and promoted DRG neurons regeneration. 4. In a transected femoral nerve rat model, the number of motoneurons projected correctly to muscle in the MNTF6mer treated animals in a dose response manner. At the optimal dose, the number of motoneurons projected correctly to muscle is three times the number of motoneurons projected incorrectly to the skin ($p<0.0001$). 5. In a zebrafish bioassay MNTF6mer protected LGA-induced apoptosis in the PNS and reduced apoptosis by 49% in the peripheral neuromuscular junctions.

The ability of the exemplary MNTF peptide GM602 (FSR-YAR; SEQ ID NO: 2), a 6-amino acid peptide analog of Motoneurontrophic factor (MNTF6mer) to protect the brain from acute ischemia and reperfusion injury is assessed. GM602 is chemically synthesized under GMP compliance (CS Bio Co., Menlo Park, Calif., GMP013, lot C811). This study was performed under contract with Neurological Testing Service, Inc. (NTS, Charleston, S.C.). The GM602 was provided to NTS as a solid and formulation prepared by NTS (solution stored at 4° C.).

Methods and Materials

Animals C57BL/6 mice (Jackson Laboratory, Bar Harbor, Me.), weighing 22-25 grams each were given free access to food and water before the experiment. The animals were anesthetized with halothane (1% in 70%/30% NO2/O2 by mask). Monitoring of mean arterial blood pressure (MABP) via tail cuff apparatus, and blood samples were collected to determine arterial pH levels and PaCO2 and PaO2. The MABP and heart rate was recorded using a Visitech System blood pressure monitor.

Brain temperature was monitored using a rectal thermometer and thermistor probe inserted into the temporalis muscle. The animals' body temperature was maintained at 37° C. by using a water-jacketed heating pad. Brain temperature was monitored for 1 hour prior to ischemia to 6 hours following ischemia and was recorded at 30-minute intervals.

Experimental Groups

All animals were subjected to 1.0 h ischemia followed by 24 h reperfusion. Animals were randomly assigned to a vehicle group (n=10) or groups (n=10) treated with an intravenous injection of GM602 at a dose of 1 or 5 mg/kg. Formulation of GM602 (CS Bio Co., Menlo Park, Calif., GMP013, lot C811) was performed by NTS as a stock solution by reconstituting GM602 with normal saline solution that was stored at 4° C. Vehicle control received saline solution. The bolus IV injections via tail vein were given immediately after the onset of reperfusion. The investigators were blinded to the treatment groups.

Induction of Ischemia

This study involved a transient model of ischemia. Each mouse was anesthetized and the external carotid artery (ECA) and common carotid artery (CCA) was isolated. Thermistor probes were inserted into the rectum and temporalis muscle to monitor body and brain temperature, which was maintained at 36-37 degree C. by external warming. The left common carotid artery (CCA) was exposed through a midline incision in the neck. The superior thyroid and occipital arteries were electrocoagulated and divided. A microsurgical clip was placed around the origin of the external carotid artery (ECA). The distal end of the ECA was ligated with 6-0 silk and transected. A 6-0 silk was tied loosely around the ECA stump. The clip was removed and the fire-polished tip of a 5-0 nylon suture (silicone coated) was gently inserted into the ECA stump. The loop of the 6-0 silk was tightened around the stump and the nylon suture was advanced approximately 13 mm (adjusted for body weight) into and through the internal carotid artery (ICA) until it rests in the anterior cerebral artery (ACA), thereby occluding the anterior communicating and middle cerebral arteries. After the nylon suture was in place for 1 hour, it was pulled back into the ECA and the incision closed.

Histological Examination

For histological examination, the animals were anesthetized with an intraperitoneal injection of sodium pentobarbital (50 mg/kg) 24 hours after ischemia was induced. The brains were transcardially perfused with 4 degree C., 10% phosphate-buffered saline (PBS). The brains were removed and chilled for 15 minutes at −20 degree C. before being placed in a Rodent Brain Matrix. Coronal sections (1-mm thickness) were prepared and subjected to 2% triphenyltetrazolium chloride (TTC) staining at 37 degree C. Seven serial one-mm thick coronal sections through the rostral to caudal extent of the infarction were obtained from each brain, beginning two-mm from the frontal pole. The TTC stained sections were placed in 10% neutral buffered formalin and kept in darkness at 4° C. for at least 24 hours. The infarct area in each section was determined with a computer-assisted image analysis system, consisting of a Power Macintosh computer equipped with a Quick Capture frame grabber card, Hitachi CCD camera mounted on an Olympus microscope and camera stand. NIH Image Analysis Software, v. 1.55 was used. The images were captured and the total area of damage determined over the seven sections. A single operator blinded to treatment status performed all measurements. The infarct volume was calculated by summing the infarct volumes of the sections. Infarct size (%) was calculated by using the following formula: (contralateral volume−ipsilateral undamaged volume)×100/contralateral volume to eliminate effects of oedema.

Measurement of Cerebral Blood Flow

Cerebral blood flow (CBF) was monitored by using a laser Doppler flow meter. The CBF values were determined as a percentage, because the values displayed by the laser Doppler flow meter were not absolute. As described above, the animals were anesthetized with halothane (1% in 70%/30% NO2/O2 by mask). In the hemisphere ipsilateral to the MCA occlusion, coordinates were as follows: point A, 0.5 mm posterior to the bregma and 2 mm lateral to the midline; point B, 1 mm posterior to the bregma and 1.2 mm lateral to the midline; point D, 1 mm anterior to the bregma and 1.7 mm lateral to the midline; and point C in the contralateral hemisphere, 1 mm posterior to the bregma and 2 mm from the midline. CBF was compared at 15 minutes prior to the onset of ischemia, during ischemia (15 minutes after the start of ischemia) before injection of test articles and at 30 minutes post injection (continuous measurements were taken from 15 minutes prior to ischemia to 30 minutes after the end of injection of the compound and recorded every 30 minutes). The mean values before MCA occlusion were taken as baseline and the data thereafter were expressed as percentages of the baseline value.

Behavioral Assessment

Behavioral analysis (neurological deficit) was determined in the mice before and after ischemic injury. Neurological scores were as follows: 0, normal motor function; 1, flexion of torso and contralateral forelimb when animal was lifted by the tail; 2, circling to the contralateral side when held by tail on flat surface, but normal posture at rest; 3, leaning to the contralateral side at rest; 4, no spontaneous motor activity.

Exclusion of Animals from the Study

Animals were excluded from the study based upon several criteria:

Animals die prior to completion of study (at any point). Data collected to the time of death was provided to GB.

Cerebral blood flow did not decrease to 20±5% of baseline value after occlusion (i.e., considered non-ischemic) or blood flow does not return to 90±15% of baseline value upon reperfusion.

Animals developed seizure-like activity following ischemic injury.

Excessive bleeding was detected during or immediately following ischemia.

Statistical Analysis

The results were expressed as the mean±standard deviation (SD). The significance of difference in the physiological and histological data was analyzed using a one-way analysis of variance (ANOVA) followed by Fisher's post hoc test. Repeated-measures ANOVA were computed on the monitoring data and the significance of the difference among groups were evaluated by Fisher's post hoc test.

Treatment groups. All groups were subjected to GM602 or were controls. Animals (30 animals) were subjected to IV dosing of vehicle or GM602 at the indicated doses.

Mouse Stroke Model:

| Group C57BL/6 mice | Compound | Dose (mg/kg) | Route |
|---|---|---|---|
| 1 (n = 10 mice) | Vehicle | 0 | IV |
| 2 (n = 10 mice) | GM602 | 1 mg/kg | IV |
| 3 (n = 10 mice) | GM602 | 5 mg/kg | IV |

Endpoints:

Effects of GM602 on neuroprotection from ischemia and reperfusion injury. Animals will be evaluated for cerebral blood flow (CBF), heart rate (HR), blood pressure (BP), pO2, pCO2, pH, neurological deficits (ND) and infarct volume (IFV).

All test groups have been provided to NTS; GM602 was provided as a solid material to NTS. All animals in the test groups were dosed as indicated above.

Results

Ischemia in mice (Ischemia study). The relative severity of ischemia in these studies was assessed. Data were from mice with ischemic injury that were intravenously injected with vehicle or GM602.

Figure 2A:
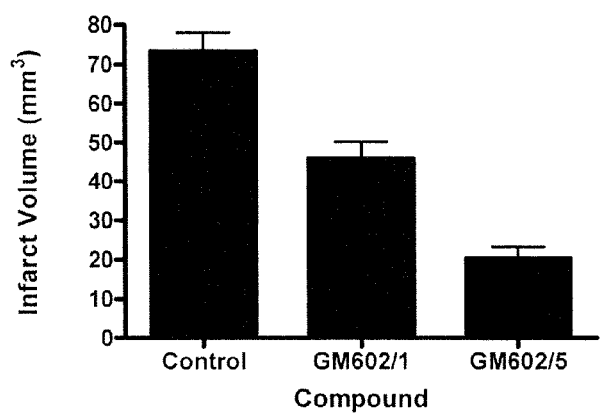
FIG. 2A. Illustrates the effects of an exemplary MNTF peptide 6-mer (FSRYAR, GM602 or SEQ ID NO: 2) on infarct volumes in the mouse following transient ischemia. All mice were subjected to 1 hour of cerebral ischemia followed by 24 hours of reperfusion. Animals were injected with vehicle (control) or GM602 at 1 mg/kg or 5 mg/kg intravenously at the end of ischemia. Animals were sacrificed on day 2 and processed to determine the infarct volume.

Infarct Volume: Compared with the vehicle-injected group, the Infarct Volume in the brains was significantly decreased in the GM602 treated groups (at both 1 and 5 mg/kg). GM602 showed a dose dependent reduction in infarct volume (Table 5). Infarct volumes vs GM6 dosage are plotted in FIG. 2A. The percent decrease in infarct volume in the brains is presented in Table 5. As shown in the table, post ischemia IV administration of GM602 at 0, 1, or 5 mg/kg showed 57, 39 and 12% infarct size. The infarct volume is 73.37 mm3 for vehicle group, 45.93 mm3 and 20.29 mm3 for GM602 treated groups at 1 or 5 mg/kg respectively. Thus, post ischemia IV administration of GM602 at 1 or 5 mg/kg resulted in 38% and 73% decrease in infarct volume respectively compared to vehicle.

pH) between the vehicle and treated mice at baseline, during ischemia, or after reperfusion (FIGS. 3-7), except a significant increase over vehicle group in cerebral blood flow after reperfusion was observed in the group treated with 5 mg/kg of GM602, which helps to mitigate the ischemic effect caused by the blockage of blood flow.

| Compound | CBF after reperfusion | P value compare to vehicle |
|---|---|---|
| Vehicle | 84.9 | |
| GM602 (1) | 89.6 | P < 0.07 |
| GM602 (5) | 91.2 | P < 0.003 |

Behavioral Measurements

Figure 8:
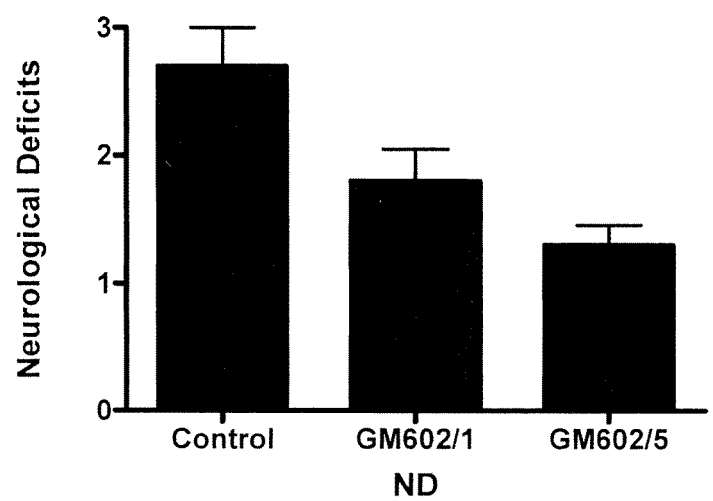
FIG. 8. Neurological deficit measurements in mice subject to ischemia/reperfusion injury. All mice were subjected to 1 hour of cerebral ischemia followed by 24 hours of reperfusion. Animals were injected with vehicle (control) or GM602 at 1 mg/kg or 5 mg/g intravenously at the end of ischemia. Neurological deficits were measured at the end of reperfusion.

Animals were assessed for neurological deficits based on a scale of 0 to 4. Animals treated with GM602 showed a dose dependent decrease in neurological deficits (data also shown in FIG. 8).

| Compound | Neurological Deficits | P value compare to vehicle |
|---|---|---|
| Vehicle | 2.7 ± 0.30 | |
| GM602 (1) | 1.8 ± 0.249 | P < 0.04 |
| GM602 (5) | 1.3 ± 0.153 | P < 0.0006 |

Stroke is the third most common cause of death and the main cause of disability in the United States. The outcome and infarction size after focal cerebral ischemia is determined by both "necrotic" (paraptosis) cell death and by delayed neuronal cell loss in the borderzone of ischemia (programmed cell death or apoptosis). Recent therapies have emerged to treat ischemic stroke. However, these treatments mostly dealt with dissolving the blood clot but did not address neuroprotection, reduction of behavioral deficit or brain infarct volume once the neuronal cell death cycle has been triggered. Understanding the basic mechanisms that influence cell loss will help in the design of drugs and applications to reduce cell death associated with ischemic injury.

MNTF is a trophic factor that can provide protection from neurological diseases and allow for regeneration of neuronal tissue following injury or ischemic stroke. The studies performed here demonstrate the ability of GM602, the 6-amino acid (FSRYAR) analog of MNTF to protect the brain from the detrimental effects of cerebral ischemia and reperfusion injury in an effective and efficient way. Intravenous adminis-

TABLE 5

Percent decrease in infarct in the brain.

| Group | Dose | GB ID Compound | Infarct Size (%) | Percent reduction in Infarct size | Compound Infarct Volume (mm³) | Percent reduction in Infarct volume | P-value |
|---|---|---|---|---|---|---|---|
| 1 | 0 | Vehicle | 57% | 0 | 73.37 + 4.43 | 0 | |
| 2 | 1 mg | GM602 | 39% | 31.6% | 45.93 + 3.99 | 38% | 0.0004* |
| 3 | 5 mg | GM602 | 12% | 79% | 20.29 + 2.87 | 73% | 0.0001* |

Percent decreases are compared to the respective vehicle control animals.
p < 0.0001 for all groups compared to control
Mortality: There were no deaths in this study.

Physiological Parameters

There were no significant differences in physiological parameters (mean arterial pressure, blood pO2, pCO2, and tration of GM602 at 1 and 5 mg/kg single bolus dose demonstrated a dose dependent protective effect in the brain against ischemia/reperfusion injury by a decrease in infarct volume, improved behavioral attributes, and an increase in cerebral blood flow. These studies suggest that GM602 may have a beneficial effect in stroke.

When administered intravenously, GM602 was found to be neuroprotective against ischemia/reperfusion injury in the mouse. These studies lay the groundwork for future studies to determine the beneficial effects of GM602 in stroke and other neurodegenerative disorders.

Example 3

Spinal Cord Injury

Testing of GM603 (Exemplary MNTF 6mer FSRYAR) in the Mouse Model of Spinal Cord Injury MNTF analog GM603 (SEQ ID NO: 2; FSRYAR) was tested for efficacy in the spinal cord injury (SCI) mouse model. In order to determine the efficacy of GM603 in the SCI mouse model, mice were subjected to spinal cord impact and 14 days of recovery. Mice were injected intravenously with GM603 at several doses immediately after the injury and every day for 14 days. The animals were examined for changes in lesion volume (LV) and behavioral recovery (BR). Intravenous (i.v.) administration of GM603 (1 or 5 mg/kg) with multiple doses was examined. Administration of GM603 demonstrated changes in both LV and BR, which showed a dose dependent effect. GM603 at both 1 and 5 mg/kg showed a significant reduction in lesion volume, which translated to preservation of neurological deficits. These data demonstrated that GM603 is neuroprotective in the spinal cord following i.v. injection in the mouse model of SCI.

Abbreviations/Terminology for this Example.

"MNTF" means motoneuronotrophic factor.

"MNTF6mer" means 6-amino acid peptide analog of MNTF.

"GM603" means 6-amino acid peptide analog (FSRYAR) of MNTF for SCI.

"GM603-1" means GM603 1 mg/kg; SEQ ID NO: 2, FSRYAR.

"GM603-5" means GM603 5 mg/kg.

"SCI" means Spinal Cord Injury.

"GB" means Genervon Biopharmaceuticals, LLC.

"I.V." means intravenous.

"BR" means behavioral recovery.

MNTF 6mer is relatively small that it does not have the disadvantages of large peptides in terms of stability, solubility, mutagenicity, immunogenicity or the high cost of manufacturing through transgenic or recombinant methods. The cost of solid phase synthesizing 6aa is relatively low.

In a middle cerebral artery occlusion (MOAC) mouse stroke model, post treatment of MNTF6mer by IV injection reduced infarct volume in the brain and reduced neurological deficit in a dose response manner. High dose of MNTF 6mer reduced brain infarct volume by 74% compared with vehicle and reduced neurological deficits significantly, $p<0.0001$, suggesting that MNTF6mer may have a beneficial effect in stroke.

L-2-hydroxyglutaric acid (LGA) induces oxidative stress and apoptosis in the nervous system. In a zebrafish bioassay MNTF6mer protected LGA-induced apoptosis in the CNS and reduced apoptosis by 85% in the midbrain. (Parng et al, 2004).

In a rat sciatic nerve transection with a 8 mm gap study, MNTF6mer treated animals have significant improvement of motoneuron regeneration in a dose response manner ($p<0.0002$ at the optimal dose) and promoted DRG neurons regeneration. (Nussbaum et al, 2003).

In a transected femoral nerve rat model, the number of motoneurons projected correctly to muscle in the MNTF6mer treated animals in a dose response manner. At the optimal dose, the number of motoneurons projected correctly to muscle is three times the number of motoneurons projected incorrectly to the skin ($p<0.0001$). (Nussbaum et al, 2003).

In a zebrafish bioassay MNTF6mer protected LGA-induced apoptosis in the PNS and reduced apoptosis by 49% in the peripheral neuromuscular junctions. (Parng et al, 2004).

The ability of GB GM603, a 6-amino acid peptide analog (FSRYAR; SEQ ID NO: 2) of Motoneurontrophic factor (MNTF 6mer) to protect the spinal cord from damage or injury via bolus intravenous injection (Tyor et al., 2002; Engesser-Cesar et al., 2005) was determined. GM603 was chemically synthesized under GMP compliance (CS Bio Co., Menlo Park, Calif., GMP013, lot C811). This study was performed under contract with Neurological Testing Service, Inc. (NTS, Charleston, S.C.). The GM603 was provided to NTS as a solid and formulation prepared by NTS (solution stored at 4° C.).

Methods and Materials

Animals

C57BL/6 mice (Jackson Laboratory, Bar Harbor, Me.), weighing 22-25 grams each were given free access to food and water before the experiment. Young adult female mice (25 gm) received a spinal cord contusion using the well-characterized pneumatic impactor device.

Experimental Groups

Prior to surgical manipulation, mice were assigned to different treatment groups based on a randomized block design so that on any given surgery day all treatments were included. The investigators were blinded to the treatment groups. Formulation of GM603 (CS Bio Co., Menlo Park, Calif., GMP013, lot C811) was performed by NTS as a stock solution by reconstituting GM603 with % saline solution that was stored at 4° C. Vehicle control received saline solution. The bolus IV injections via tail vein were given immediately after the onset of reperfusion.

Induction of Spinal Cord Injury

The mice were anesthetized with ketamine (80 mg/kg) and xylazine (10 mg/kg) before the laminectomy was performed at the 10th thoracic vertebra (T10). The vertebral column was stabilized with angled clamps on the upper thoracic (T8) and lumbar (T11) levels and a brass tip diameter of 2 mm was pneumatically driven onto the exposed, intact dura overlying the dorsal spinal cord. The impactor was immediately removed, the wound irrigated with saline, and the muscle and skin openings sutured together.

Treatment

For application of compounds, GM603 was injected i.v. daily for two weeks. Immediately following the injury, GM603 at 2 different doses (1 mg/kg and 5 mg/kg) was applied. Female animals were used due to the paralysis associated with the injury and ease of voiding the bladder.

Behavior Analysis Rota-Rod and Open Field Test

For behavioral analysis, animals were tested prior to surgery and at 1, 3, 5, 7 and 14 days after surgery. Animals were placed in an open field chamber (120 cm diameter, 25 cm wall height) for 4 minutes to assure that all subjects obtained a maximum score of 21 using the Basso, Beattie, and Bresnahan (BBB) locomotor rating scale. Mice were placed in the open field for 4 minutes and videotaped for scoring. In addition, mice were tested for their ability to remain on the rotarod. For the rotarod test, mice were subjected to a 1-week learning period after which they were able to perform on an accelerating rotarod. The test was performed on days 1, 3, 5, 7, and 14 and the mice were tested until they were unable to remain on the rotating bar for more than 10 seconds on three consecutive attempts, which will be defined as rotarod failure. Maximum time was set at 90 seconds. Treatment group tallies the scores and the median values plotted as a function of time post-injury.

Histology

At the end of the study, the animals were killed and the spinal cord fixed in 4% paraformaldehyde. For analysis, 20 µm cryosections were stained for eriochrome cyanine (EC) to differentiate between white matter and cell bodies to calculate the amount of spared tissue through the lesion site. Immunocytochemical analysis was performed on the tissue. Tissue sparing was determined by computed image analysis from 10 evenly spaced sections through the injured T10 segment. The volume of necrotic tissue divided by the total cross-sectional volume is converted to a percentage and subtracted from 100%.

Exclusion of Animals from the Study

Animals were excluded from the study based upon several criteria:

Animals die prior to completion of study (at any point). Data collected to the time of death was provided to GB.

Animals developed seizure-like activity following injury.

Excessive bleeding was detected during or immediately following injury.

Statistical Analysis

The results are expressed as the mean±standard error of the mean (SEM). The significance of difference in the lesion volume and behavioral recovery were analyzed using a t-test.

Spinal Cord injury Mouse Model

| Group | No. of mice | Compound | Dose | Application | Dose/Volume |
|-------|-------------|----------|------|-------------|-------------|
| 1 | 10 | Vehicle | 0 | IV | 0 |
| 2 | 10 | GM603 | 1 mg/kg | IV | 0.100 ml |
| 3 | 10 | GM603 | 5 mg/kg | IV | 0.100 ml |

Endpoints

Behavioral Deficits

Histological Analysis

Effects of GM603 of the protection from spinal cord injury. Animals were evaluated for spinal cord injury.

All test groups have been provided to NTS; GM603 was provided as a solid material to NTS. All animals in the test groups were dosed as indicated above.

Results

Spinal cord injury in mice. SCI study. The relative severity of SCI in these studies was assessed. Data were from mice with SCI that were intravenously injected with vehicle or GM603.

Figure 9:
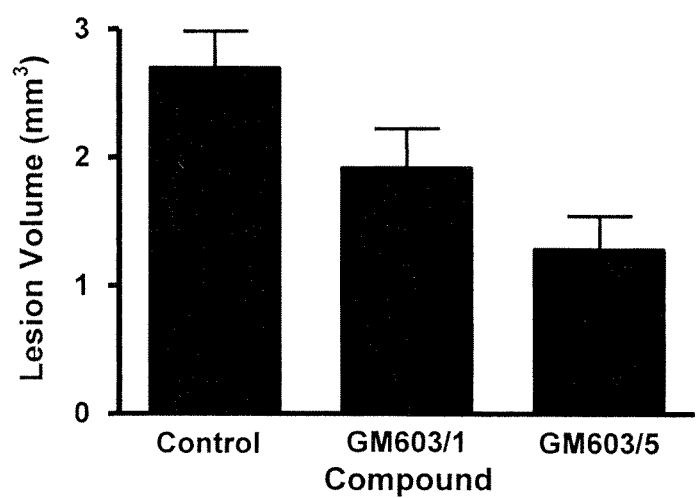
FIG. 9. Illustrates the effects of an exemplary MNTF peptide analog GM603 (FSRYAR, SEQ ID NO: 2) on lesion volumes in the mouse following spinal cord injury. All mice were subjected to spinal cord injury followed by 14 days of recovery. Animals were injected with vehicle (control), GM603 intravenously at the after the injury and every day until sacrifice. Animals were sacrificed on day 14 and processed to determine the lesion volume.
Figure 10:
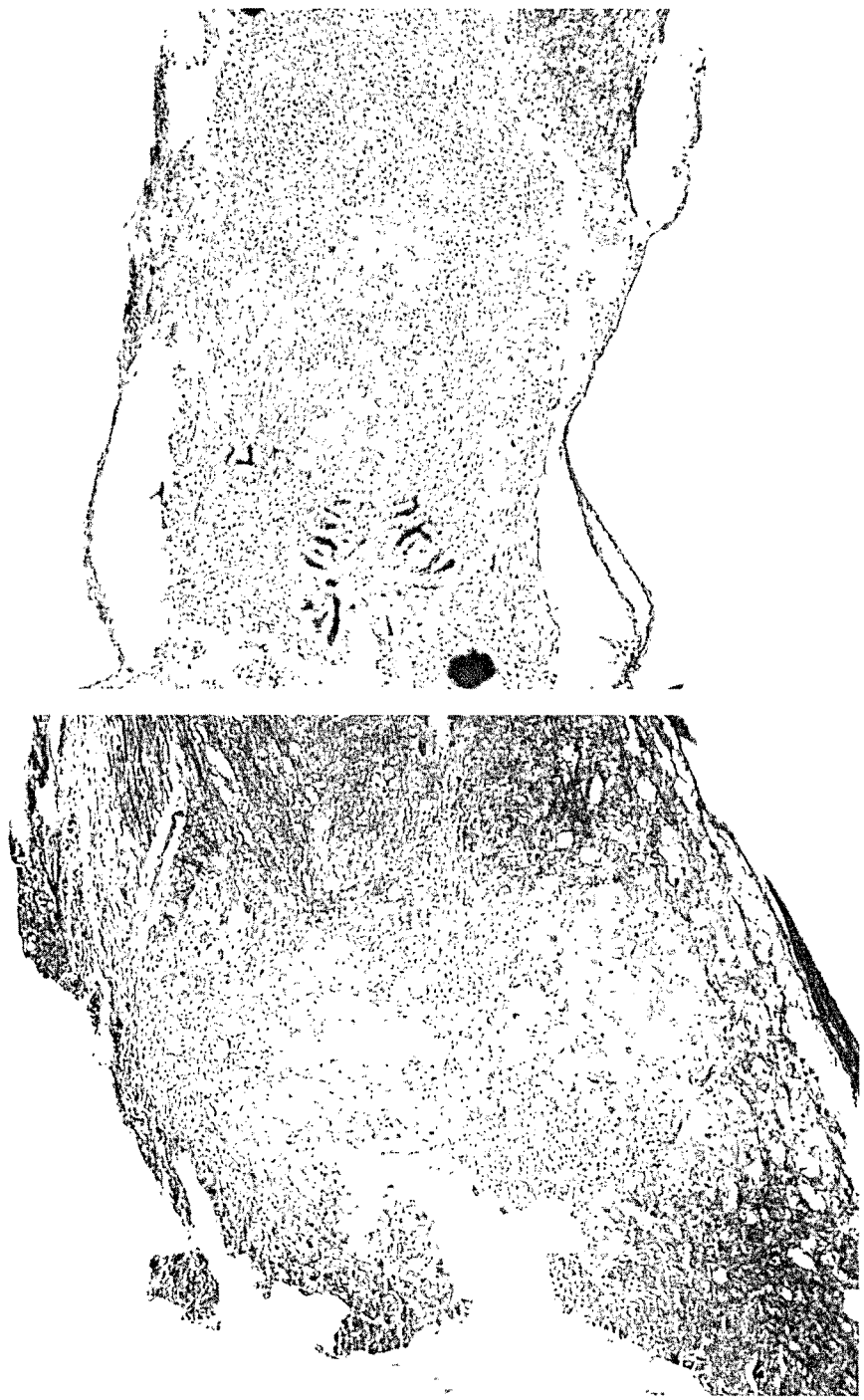
FIG. 10. Damaged area of spinal cord following spinal cord injury (SCI). All mice were subjected to spinal cord injury followed by 14 days of recovery. Tissue sections were cut and processed for evaluation of area of damage. A. Vehicle treated mouse with SCI. B. Mouse treated with 5 mg/kg GM603. The damaged area stains in red and the undamaged area stains blue. As can be seen in the figure, the damaged area in B is significantly smaller in the GM603 treated animals.

Lesion volume: Compared with the vehicle-injected group, the lesion volume in the spinal cord was significantly decreased with the GM603 groups (both 1 and 5 mg/kg). GM603 showed a dose dependent reduction in lesion volume from 1 to 5 mg/kg (Table 6). Lesion volumes are plotted in FIG. 9. The percent decrease in lesion volume present in the spinal cords is presented in Table 6. As shown in the table, GM603 at 1 or 5 mg/kg showed a 28 or 53% decrease in lesion volume compared to vehicle, respectively. FIG. 10 shows representative pictures of the spinal cords form the injured animals. FIG. 10 shows that in vehicle treated animals the lesion volume (stained red) is very large, whereas in the GM603 treated animals (5 mg/kg) the lesion volume (stained red) is considerable smaller.

TABLE 6

| Group | Dose | Compound | Lesion volume (mm$^3$) | Percent reduction in Lesion volume | P-value |
|-------|------|----------|------------------------|-----------------------------------|---------|
| 1 | 0 | Vehicle | 2.696 ± 0.2902 | 0 | |
| 2 | 1 mg | GM603 | 1.912 ± 0.3139 | 28% | 0.05* |
| 3 | 5 mg | GM603 | 1.274 ± 0.2680 | 53% | 0.002* |

Percent decreases are compared to the respective vehicle control animals.
*Compared to Group 1 (Vehicle)

Mortality: There were no deaths in this study.

Behavioral Measurements

Figure 11:
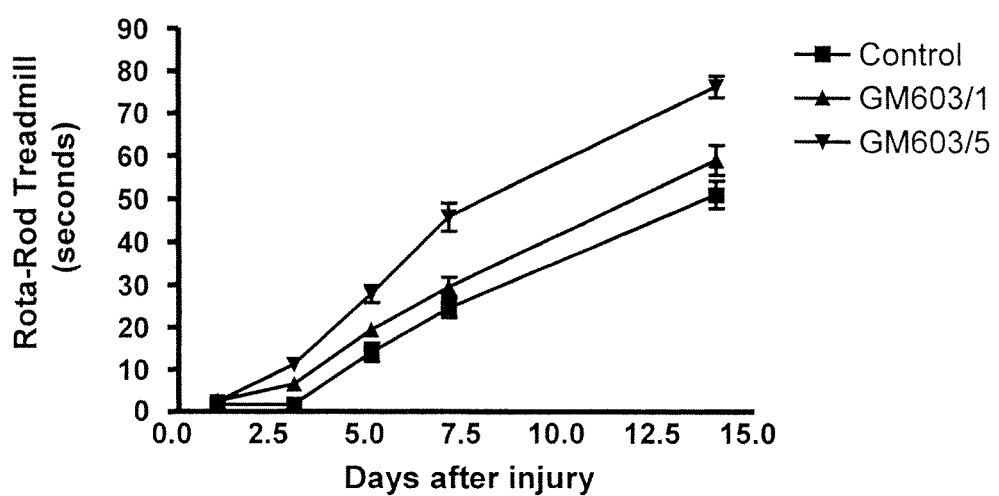
FIG. 11. Illustrates the results of the Rota-Rod Treadmill test on animals subject to spinal cord injury. All mice were subjected to spinal cord injury followed by the number of days indicated in the figure. Behavioral analysis was measured after injury.

Mice were subjected to a rota-rod test. Animals were tested for their ability to maintain a presence on the rota-rod for a maximum time of 90 seconds. The mice were tested in the rota-rod test, which was used to measure motor performance. The apparatus (model-DS 37) consisted of a bar with a diameter of 2.5 cm, subdivided into six compartments by disks, 25 cm in diameter. The bar rotated at a constant speed of 22 rpm. The animals were tested on days 1, 3, 5, 7, and 14. The time they remained on the rotating bar (maximum of 90 s) was recorded. As seen in FIG. 11, all animals demonstrated an initial inability to remain on the rota-rod. However, after 3 days there was a clear delineation between the groups. At days 3 and 5 the difference was significant ($P<0.05$) and by day 7 the significance was even greater ($P<0.01$).

Figure 12:
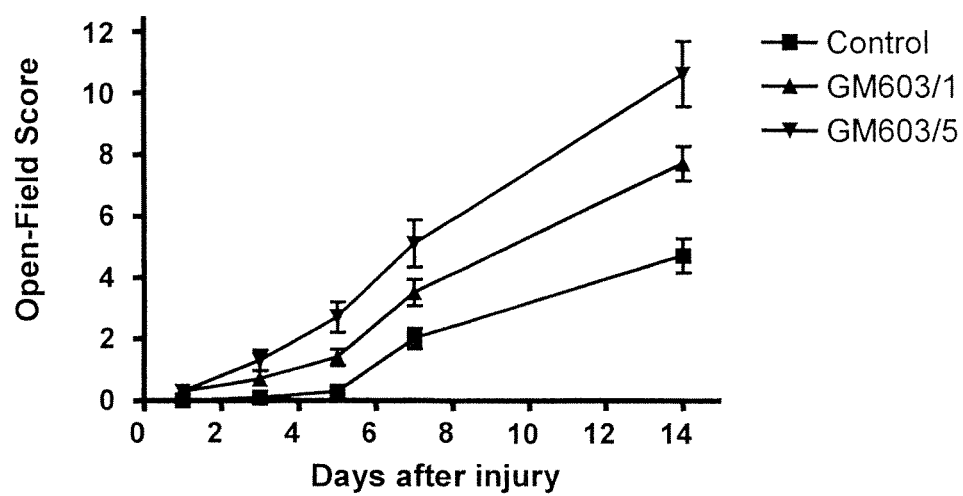
FIG. 12. Open-field behavioral measurements in mice subject to spinal cord injury. All mice were subjected to spinal cord injury followed by the number of days indicated in the figure. Behavioral analysis was measured after injury.

Animals were assessed in an open field chamber (120 cm diameter, 25 cm wall height) for 4 minutes to assure that all subjects could obtained a maximum score of 21 using the Basso, Beattie, and Bresnahan (BBB) locomotor rating scale. Mice were placed in the open field for 4 minutes and videotaped for scoring. As seen in FIG. 12, on day 1 all animals showed the same deficit in movement due to the injury. However, by days 3 the GM603 treated animals showed a significant improvement compared to the vehicle treated animals. By day 5 the significance was $P<0.01$.

Discussion

MNTF is a trophic factor that can provide protection from neurological diseases and allow for regeneration of neuronal tissue following injury or grafting. The studies performed here demonstrate the ability of MNTF6mer analog GM603 to protect the spinal cord from the detrimental effects of SCI in an effective and efficient way. Intravenous administration of GM603 at 1 and 5 mg/kg daily injections for 14 days demonstrated a dose dependent protective effect in the spinal cord against SCI by a decrease in lesion volume and behavioral attributes. These studies suggest that GM603 may have a beneficial effect in SCI.

When administered intravenously, GM603 was found to be protective against spinal cord injury in the mouse.

Example 4

ALS

Testing if Gm604 in the Mouse Model of Amyotrophic Lateral Sclerosis

MNTF peptide analog GM604 (FSRYAR; SEQ ID NO: 2) was tested for efficacy in the amyotrophic lateral sclerosis (ALS) mouse model. In order to determine the efficacy of GM604 in the ALS mouse model, mice were injected intravenously with GM604 at two doses at 80 days of age and continued until the died. The animals were examined for changes in age of disease onset, age of death, and behavioral expression of the disease. Intravenous (i.v.) administration of GM604 (1 or 5 mg/kg) with multiple doses was examined. Administration of GM604 demonstrated changes in age of onset of the disease, age of death and behavioral manifestations of the disease, which showed a dose dependent effect. GM604 at both 1 and 5 mg/kg showed a significant extension of life expectancy in the animals, which translated to preservation of neurological deficits. These data demonstrated that GM604 can be neuroprotective in the mouse model of ALS.

Abbreviations/Terminology for this Example.

"MNTF" means motoneuronotrophic factor.

"MNTF6mer" means 6-amino acid peptide analog of MNTF.

"GM604" means 6-amino acid peptide analog (FSRYAR) of MNTF for ALS.

"GM604-1" means GM604 1 mg/kg.

"GM604-5" means GM604 5 mg/kg.

"ALS" means amyotrophic lateral sclerosis.

"GB" means Genervon Biopharmaceuticals, LLC.

"I.V." means intravenous.

Assessment of the ability of GB test article GM604, a 6-amino acid peptide analog (FSRYAR; SEQ ID NO: 2) of Motoneurontrophic factor (MNTF6mer) to delay or modulate the onset of clinical signs of the ALS disease, improvement of the clinical signs, and end stage of disease in the ALS mice model. Animals are subjected to intravenous in injection of GM604, which is chemically synthesized under GMP compliance (CS Bio Co., Menlo Park, Calif., GMP013, lot C811). The GM604 was provided as a solid and formulation (solution stored at 4:C).

Methods and Materials

Animals

ALS mice (Jackson Laboratory, Bar Harbor, Me.), were bred and maintained under Specific Pathogen Free (SPF) conditions. Animals weighing 22-25 grams each were given free access to food and water before the experiment. Young adult mice (25 gm) were subjected to intravenous injections of GM604.

Experimental Groups

Prior to surgical manipulation, mice were assigned to different treatment groups based on a randomized block design so that on any given surgery day all treatments were included. The investigators were blinded to the treatment groups. Formulation of GM604 was performed as a stock solution by reconstituting GM604 with saline solution that was stored at 4° C. Vehicle control received saline solution. The bolus IV injections via tail vein.

Treatment

For application of compounds, GM604 was injected i.v. daily until the animal died. GM604 at 2 different doses (1 mg/kg and 5 mg/kg was applied. Both male and female mice were used because of the number of animals required for the study.

Behavior Analysis:

Rota-Rod

For behavioral analysis, animals were tested prior to disease onset (day 80) and every third day until the animal died. Mice were tested for their ability to remain on the rotarod. For the rotarod test, mice were subjected to a 1-week learning period after which they were able to perform on an accelerating rotarod. The test was performed every third day and the mice were tested until they were unable to remain on the rotating bar for more than 10 seconds on three consecutive attempts, which will be defined as rotarod failure. Maximum time was set at 180 seconds. Treatment group tallies the scores and the median values plotted as a function of age.

Grip Strength

A grip strength meter (San Diego Instruments) was used to measure the forelimb strength of the mice in Newtons twice a week. This measured the peak amount of force a mouse applied to a bar with its forelimbs when pulled away from the sensor in a straight line by its tail. After four attempts, the highest result was used for analysis.

Tail Test

The mouse was lifted in the air by its tail and examined for hindlimb extension. The lack of hindlimb extension was defined as tail test failure.

Clinical Evaluation

The mice were given a clinical score from 0 to 4 on based on the following criteria. No sign of weakness (0); tremor and loss of splay reflex (1); paresis in one hindlimb 2); paresis in both hind-limbs (3); paralysis of one or both hind-limbs (4). Mice were sacrificed at the level 4 for humane reasons.

Histology

At the end of the study, the animals were killed and the spinal cord fixed in 4% paraformaldehyde for analysis.

Exclusion of Animals from the Study

Animals were excluded from the study based upon several criteria:

No animals were excluded from the study.

Statistical Analysis.

The results are expressed as the mean±standard error of the mean (SEM). The significance of difference in the age of onset, age of death, and behavioral manifestations were analyzed using a t-test.

ALS Mouse Model

| Group | No. of mice | Compound | Dose | Application | Dose/Volume |
|---|---|---|---|---|---|
| 1 | 10 | Vehicle | 0 | IV | 0 |
| 2 | 10 | GM604 | 1 mg/kg | IV | 0.100 ml |
| 3 | 10 | GM604 | 5 mg/kg | IV | 0.100 ml |

Endpoints

Age of Disease Onset

Age of Death

Behavioral Deficits

Histological Analysis

All test groups have been provided to NTS; GM604 was provided as a solid material to NTS. All animals in the test groups were dosed as indicated above.

Results

ALS study. The relative severity of ALS in these studies was assessed. Data were from mice with ALS that were intravenously injected with vehicle or GM604.

Figure 13:
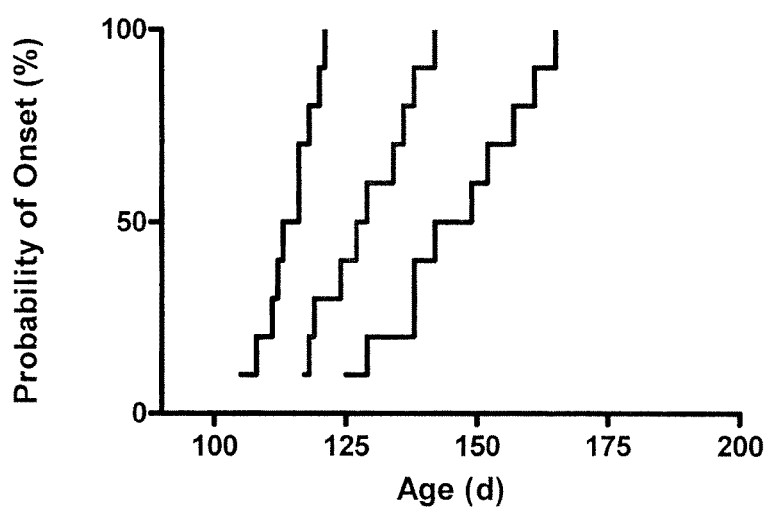
FIG. 13. Effects of an exemplary MNTF peptide analog GM604 (FSRYAR, SEQ ID NO: 2) on the age of disease onset in the ALS mouse. All mice were injected with vehicle (control) or GM604 intravenously at day 80 and every day until sacrifice. Animals were recorded as to the time of onset of the disease.

Age at disease onset: Compared with the vehicle-injected group, the age of onset of the disease was significantly extended in the ALS mice treated with GM604 (both 1 and 5 mg/kg). GM604 showed a dose dependent delay in the age of disease onset from 1 to 5 mg/kg (Table 7). Onset of disease profiles are plotted in FIG. 13. The percent increase in age of disease onset is presented in Table 7. As shown in the table, GM604 at 1 or 5 mg/kg showed a 12 or 27% increase in age of disease onset compared to vehicle, respectively.

TABLE 7

Age of disease onset in the ALS mice.

| Group | Dose | Compound | Age of disease onset (median) | Percent increase in age of onset | P-value |
|---|---|---|---|---|---|
| 1 | 0 | Vehicle | 114.5 | 0 | |
| 2 | 1 mg | GM604 | 128 | 12% | 0.001* |
| 3 | 5 mg | GM604 | 145.5 | 27% | 0.001* |

Percent increases are compared to the respective vehicle control animals.
*Compared to Group 1 (Vehicle)

Age at Death

Figure 14:
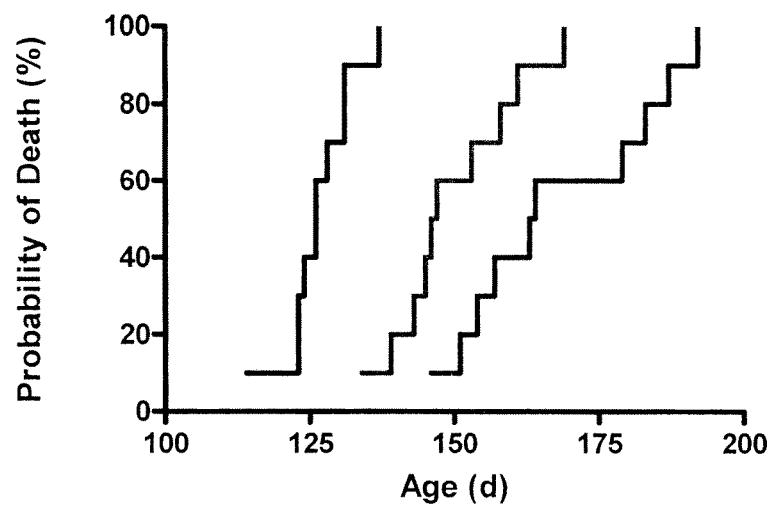
FIG. 14. Effects of an exemplary MNTF peptide analog GM604 on age of death in the ALS mouse. All mice were injected with vehicle (control) or GM604 intravenously at day 80 and every day until sacrifice. Animals were recorded as to the time of death based on the hindlimb paralysis.

Compared with the vehicle-injected group, the age at death was significantly extended in the ALS mice treated with GM604 (both 1 and 5 mg/kg). GM604 showed a dose dependent delay in the age at death from 1 to 5 mg/kg (Table 8). Age at death is plotted in FIG. 14. The percent increase in age at death is presented in Table 8. As shown in the table, GM604 at 1 or 5 mg/kg showed a 16 or 30% increase in age at death compared to vehicle, respectively.

TABLE 8

Age at death in the ALS mice.

| Group | Dose | Compound | Age at death (median) | Percent increase in age at death | P-value |
|---|---|---|---|---|---|
| 1 | 0 | Vehicle | 126 | 0 | |
| 2 | 1 mg | GM604 | 146.5 | 16% | 0.001* |
| 3 | 5 mg | GM604 | 163.5 | 30% | 0.001* |

Percent increases are compared to the respective vehicle control animals.
*Compared to Group 1 (Vehicle)

Mortality

There were no deaths not related to the disease in this study.

Behavioral Measurements.

Figure 15:
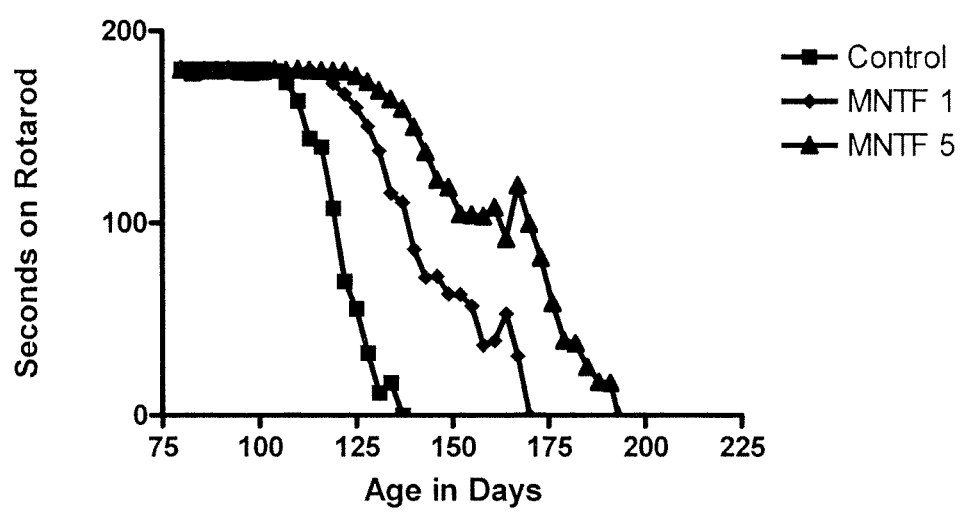
FIG. 15. Rota-Rod Treadmill test on ALS animals. All mice were transgenic for the G93A SOD mutation and were treated with saline or exemplary MNTF peptide analog GM604 as indicated. Behavioral analysis was measured at the indicated times.

Rota-Rod:

Mice were subjected to a rota-rod test. Animals were tested for their ability to maintain a presence on the rota-rod for a maximum time of 180 seconds. The mice were tested in the rota-rod test, which was used to measure motor performance. The apparatus (model-DS 37) consisted of a bar with a diameter of 2.5 cm, subdivided into six compartments by disks, 25 cm in diameter. The bar rotated at a constant speed of 22 rpm. The animals were tested twice a week starting on day 80. The time they remained on the rotating bar (maximum of 180 s) was recorded. As seen in FIG. 15, all animals were able to navigate the rota-rod efficiently until the onset of disease (see FIG. 15).

TABLE 9

Rota-rod analysis in the ALS mice.

| Group | Dose | Compound | Age (median) | Percent increase in rota-rod performance | P-value |
|---|---|---|---|---|---|
| 1 | 0 | Vehicle | 124 | 0 | |
| 2 | 1 mg | GM604 | 141 | 14% | 0.001* |
| 3 | 5 mg | GM604 | 174.5 | 41% | 0.001* |

Percent increases are compared to the respective vehicle control animals.
*Compared to Group 1 (Vehicle)

Grip Strength

Figure 16A:
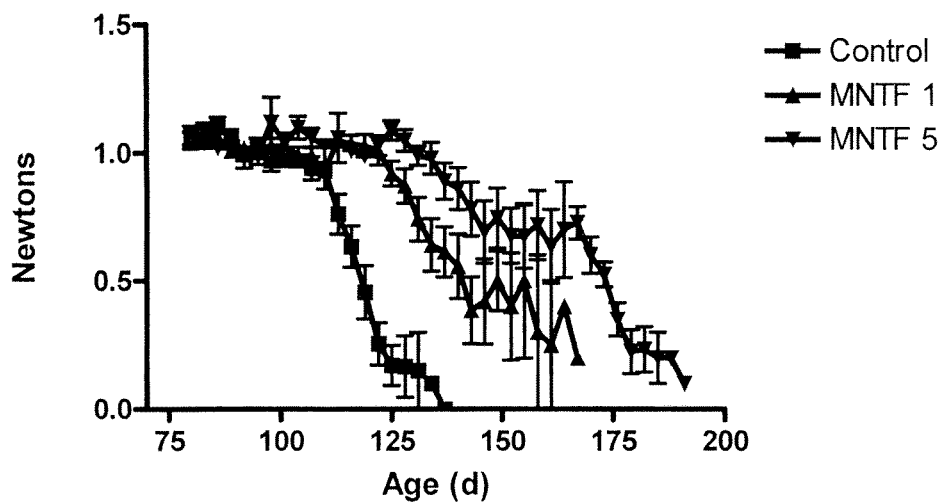
FIG. 16. Grip strength test on ALS animals. All mice were transgenic for the G93A SOD mutation and were treated with saline or GM604 as indicated. Clinical score on ALS animals. All mice were transgenic for the G93A SOD mutation and were treated with saline or GM604 as indicated. The clinical score was measured at the indicated times as outlined in the methods section. No sign of weakness (0); tremor and loss of splay reflex (1); paresis in one hindlimb (2); paresis in both hindlimbs (3); paralysis of one or both hindlimbs (4) (FIG. 16B).

Mice were examined for their grip strength during the progression of the disease and in the presence of GM604. The ALS mice treated with GM604 showed a significant delay in the decrease in grip strength when compared to the control mice (FIG. 16A and Table 10). Overall, the mice treated with 1 or 5 mg/kg of GM604 performed better in than the control animals.

TABLE 10

Grip strength in the ALS mice.

| Group | Dose | Compound | Age (median) | Percent increase in grip strength | P-value |
|---|---|---|---|---|---|
| 1 | 0 | Vehicle | 120 | 0 | |
| 2 | 1 mg | GM604 | 137 | 14% | 0.001* |
| 3 | 5 mg | GM604 | 169 | 41% | 0.001* |

Percent increases are compared to the respective vehicle control animals.
*Compared to Group 1 (Vehicle)

Clinical Evaluation

Figure 16B:
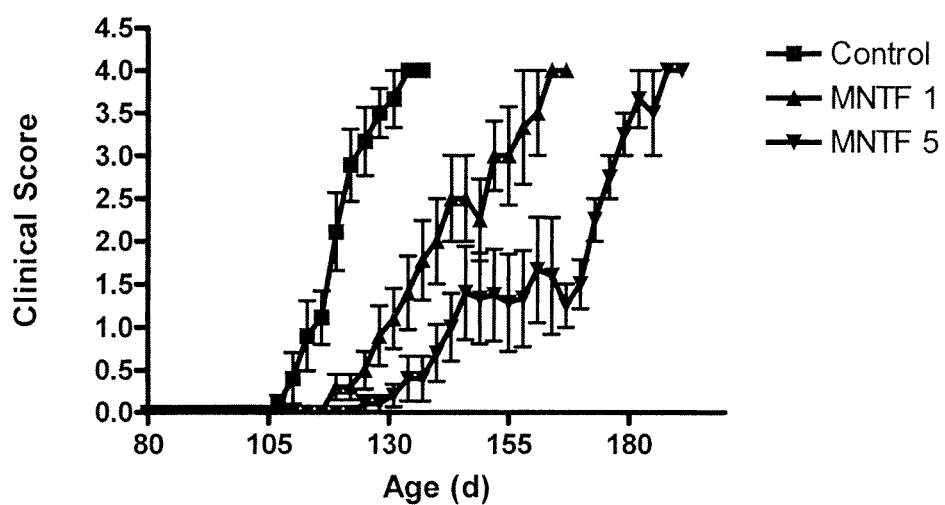

Mice were examined for their clinical score during the progression of the disease and in the presence of GM604. The ALS mice treated with GM604 showed a significant delay in the decrease in clinical score when compared to the control mice (FIG. 16B and Table 11). Overall, the mice treated with 1 or 5 mg/kg of GM604 performed better in than the control animals.

TABLE 11

Clinical score in the ALS mice.

| Group | Dose | Compound | Age (median) | Percent increase in clinical score | P-value |
|---|---|---|---|---|---|
| 1 | 0 | Vehicle | 113 | 0 | |
| 2 | 1 mg | GM604 | 139 | 23% | 0.001* |
| 3 | 5 mg | GM604 | 173 | 53% | 0.001* |

Percent increases are compared to the respective vehicle control animals.
*Compared to Group 1 (Vehicle)

MNTF is a trophic factor that can provide protection from neurological diseases and allow for regeneration of neuronal tissue following injury or grafting. The studies performed here demonstrate the ability of MNTF6mer analog GM604 to protect the spinal cord from the detrimental effects of ALS in an effective and efficient way. Intravenous administration of GM604 at 1 and 5 mg/kg daily injections demonstrated a dose dependent protective effect in the mouse model of ALS by an increase in age of disease onset, age at death and behavioral parameters. These studies demonstrated that GM604 can have a beneficial effect in ALS.

When administered intravenously, GM604 was found to be protective against ALS in the mouse.

Example 5A

Mouse Parkinson's Disease Model

GM6 (FSRYAR, SEQ ID NO: 2) (CS Bio Co., Menlo Park, Calif.) was tested for efficacy in a mouse Parkinson's disease (PD) model.

In order to determine the efficacy of GM6 in PD, mice were injected with 1-methyl-4-phenyl-1,2,3,6-tetrahydropyridine (MPTP) to induce PD and then intravenously with GM6 at several different doses to determine the influence on attenuation of PD. Intravenous (i.v.) administration of GM6 (1, 5, 10 or 20 mg/kg) for five days (twice per day) was examined. Administration of GM6, demonstrated a dose dependent attenuation of PD in the mice with 20 mg/kg showing the most efficacy. Behavioral, biochemical and histological analysis demonstrated the attenuation illustrating a unique effect for GM6 in PD. These data suggest that GM6 is effective in the mouse model of PD following i.v. injection and may be a potential treatment for PD patients.

Abbreviations/Terminology for this Example.

"MNTF" means motorneuron trophic factor.

"GM6" and "6mer" each mean 6 amino acid peptide analog of MNTF.

"PD" means Parkinson's disease.

"MPTP" means 1-methyl-4-phenyl-1,2,3,6-tetrahydropyridine.

"DOPAC" means dihydroxyphenylacetic acid.

"HVA" means homovanillic acid.

"DA" means dopamine.

"Genervon" and "GB" each mean Genervon Biopharmaceuticals, LLC.

"I.V." means intravenous.

Determination of the ability of the 6 amino acid analog (GM6) of Motoneurontrophic factor (MNTF) to determine the efficacy of GM6 in a mouse model of Parkinson's disease (PD).

GM6 is a synthesized 6 amino acid peptide (MNTF). The GM6 was provided to NTS as a solid and formulation prepared by NTS (solution stored at 4° C.).

A major obstacle to treat Central Nervous System diseases and disorders is the difficulty of delivering the drug to the Central Nervous System. Determining the bioavailability of the drug and the effect on various neurological disorders is important for potential therapeutic intervention.

Assessment of the efficacy of GM6 in a mouse model of PD via intravenous injection.

Methods and Materials

Study design. Male C57BL/6 mice were injected with MPTP as described below and examined for the protection from PD by GM6 at the indicated doses. Animals were examined for behavioral manifestations, biochemical and histological changes.

MPTP treatment. C57BL/6 mice were injected (i.p., 20 mg/kg in 0.1 ml water at 2 hour intervals for 4 doses of 1-methyl-4-phenyl-1,2,3,6-tetrahydropyridine, MPTP, Sigma M-0896) and then examined at one week after injections. Control mice in each group received four i.p. injections of saline. Mice were kept on heated blankets for 24 h after the injections.

Administration of MNTF For MNTF (GM6) treatment, mice received twice daily (12 hr apart) intravenous injections of varying doses of MNTF of 1, 5, 10 or 20 mg/kg in saline starting 30 min after the first MPTP injection and continuing through 4 additional days after the last injection of MPTP; control mice received saline only. N=10 per group.

Behavioral testing. Male mice were used in the behavioral testing. All animals were maintained on a 12-h light-dark cycle (lights on at 0700 to 1900) and were permitted free access to food and water. To evaluate spontaneous motor activity, we used an activity monitor consisting of 4 Plexiglas cylinders (23 cm×30 cm, diameter×height) each equipped with three infrared beams and an automated counting system. The spontaneous activity test was started by placing the mouse in the cylinder. After 3 min environmental adaptation, the activity was assessed by counting the number of infrared beam crossings in the photocell apparatus per 5 min. To assess sensorimotor coordination, the mice were evaluated in the rotarod task. The rotarod unit consists of a rotating spindle (diameter 7.3 cm) and five individual compartments to test five mice at a time. After twice daily training for two successive days (speed 12 rpm on the first day and 18 rpm on the second day), the rotation speed of test was increased to 25 rpm on the third day in a test session. The time each mouse remained on the rotating bar was recorded for three trials for each mouse, at a 5-min interval and a maximum trial length of 60 s per trial. Data are presented as mean time on the rotating bar over the three test trials.

Quantification of Brain Monoamines.

Dissected brain regions were sonicated in 0.1 M perchloric acid and 0.1 mM EDTA (10 mg/100 µl). The extracts were then centrifuged for 15 min and the supernatant were collected and stored at −20° C. Monoamine (dopamine, [DA]) and metabolites (dihydroxyphenylacetic acid [DOPAC], homovanillic acid [HVA]) were measured with high-pressure liquid chromatography (HPLC) using electrochemical detection.

Immunohistochemistry. All mice (½ brain) were drop fixed in 4% PFA. The brains were fixed in 4% PFA for 12 h at 4° C., and then stored in 30% sucrose in PBS. Fifty-micrometer sections were cut and processed for immunohistochemistry using a 1:1000 dilution of a TH antibody (Sigma T-1299). Tyrosine hydroxylase (TH) immunoreactivity was visualized using a monoclonal anti-TH antibody. Preliminary quantification of TH-immunopositive cells in the substantia nigra and ventral tegmental areas were made using image analysis. Sections were dried and mounted in Depex. Cell counting was performed using a computer-assisted stereological toolbox. All cell counts were done blind to drug treatments and performed at 100-fold magnification.

Statistical analysis. The results were expressed as the mean±standard deviation (SD). The significance of difference in the data was analyzed using a t-test.

Exclusion of Animals from the Study.

Animals were excluded from the study based upon several criteria:

Animals that died prior to completion of study (at any point).

Animals developed severe complications following administration of test articles.

Treatment groups. All groups were subjected to GM6 or were controls. Animals (60 animals) were subjected to bolus i.v. dosing by tail vein of vehicle or MNTF at the indicated doses. Animals were injected 2 times per day for 5 days.

Mouse PD Model Using GM6: an Exemplary MNTF 6-mer FSRYAR SEQ ID NO: 2):

| Group C57BL/6 male mice | Compound | Dose (mg/kg) | Route |
| --- | --- | --- | --- |
| 1 (n = 10 mice) | Vehicle | 0 | IV |
| 2 (n = 10 mice) | exemplary MNTF GM6: FSRYAR | 1 mg/kg/day | IV |
| 3 (n = 10 mice) | exemplary MNTF GM6: FSRYAR | 5 mg/kg/day | IV |
| 4 (n = 10 mice) | exemplary MNTF GM6: FSRYAR | 10 mg/kg/day | IV |
| 5 (n = 10 mice) | exemplary MNTF GM6: FSRYAR | 20 mg/kg/day | IV |
| 6 (n = 10 mice) | Control | Control | NA |

Endpoints

Modulation of PD in the Mouse

All test groups have been provided to NTS; GM6 was provided as a solid material to NTS. All animals in the test groups were dosed as indicated above.

Behavioral tests. The efficacy of GM6 in a mouse model of MS was assessed. Data from mice that were i.v. administered with vehicle or GM6 (at indicated doses).

Behavioral Analysis After induction of PD with MPTP, the mice were administered GM6 at the indicated doses above. Animals were examined on day 2 and every day to determine the behavior of the animals following MPTP and GM6. Mice were injected with GM6 every day for five days starting on the day of MPTP administration. The GM6 was started 30 min after the last MPTP injection and continued for four additional days. As seen in Tables 12 and 13, the mice treated with vehicle showed a significant increase in behavioral scores (both spontaneous activity and rotarod tests Figure) compared to the control or treated animals. Treatment with GM6 showed a significant improvement (attenuation) in the behavior. GM6 at 5, 10 and 20 mg/kg showed a significant benefit, whereas the 1 mg/kg did not show any improvement.

Spontaneous Locomotor Activity

TABLE 12

Spontaneous activity

| Treatment | Number of movements/5 min |
|---|---|
| Vehicle | 67.60 ± 13.28 (NA) |
| GM6 (1 mg/kg) | 74.50 ± 19.12 (0.3610) |
| GM6 (5 mg/kg) | 121.6 ± 21.69 (<0.0001) |
| GM6 (10 mg/kg) | 161.5 ± 24.95 (<0.0001) |
| GM6 (20 mg/kg) | 254.9 ± 26.69 (<0.0001) |
| Control | 292.0 ± 33.75 (<0.0001) |

Rotarod Test

TABLE 13

Rotarod Test

| Treatment | Latent Period |
|---|---|
| Vehicle | 41.40 ± 3.645 (NA) |
| GM6 (1 mg/kg) | 42.70 ± 4.237 (0.4741) |
| GM6 (5 mg/kg) | 38.00 ± 2.331 (0.0947) |
| GM6 (10 mg/kg) | 33.90 ± 3.091 (0.0006) |
| GM6 (20 mg/kg) | 23.80 ± 1.003 (<0.0001) |
| Control | 20.29 ± 5.254 (<0.0001) |

Mortality: There were no deaths in this study.

Figure 21A:
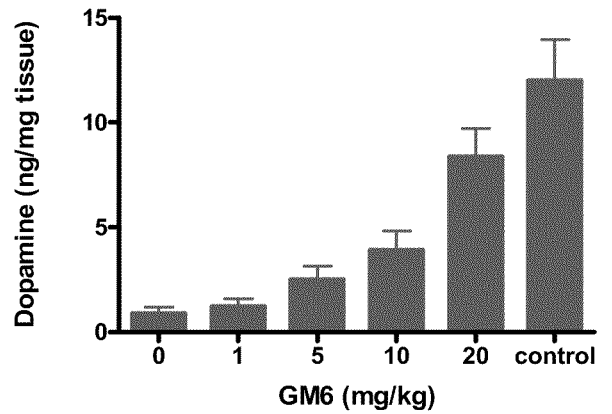
FIGS. 21A, 21B, 21C. Illustrate Monoamine and metabolite levels following MPTP treatment. Male C57BL/6 mice were injected with MPTP followed by GM6 at the indicated doses for 5 days. Animals were evaluated for monoamine and metabolite levels at the end of the study.
Figure 21B:
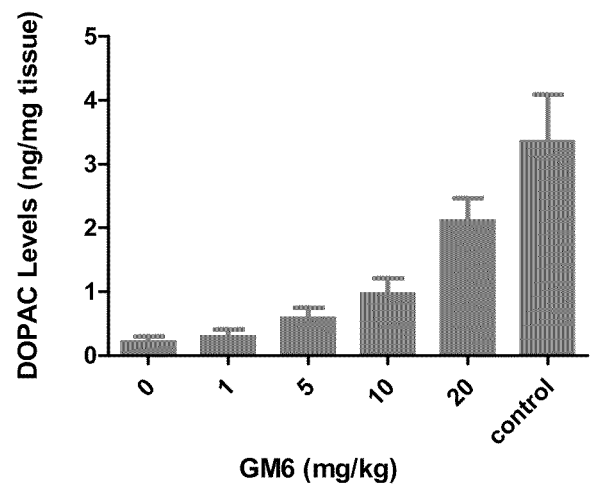
Figure 21C:
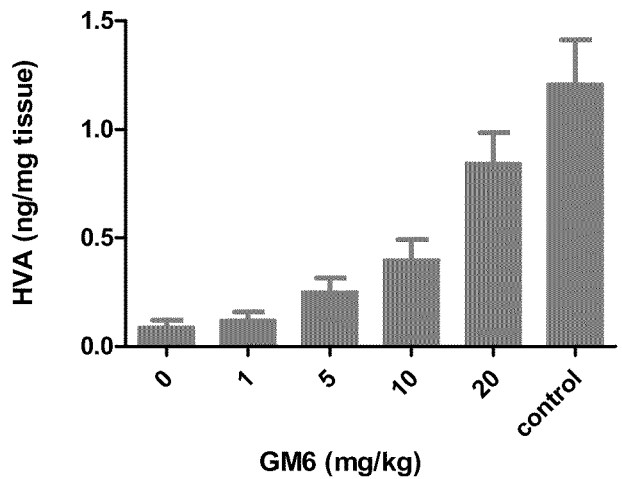

Monoamine and metabolite levels in the brains of MPTP treated animals. The efficacy of GM6 on brain monoamine and metabolite levels that change during treatment with MPTP and are markers of PD were determined. As seen in Table 14 and FIGS. 21A-21C, the levels of dopamine, DOPAC and HVA all were higher in the GM6 treat animals compared to the vehicle treated animals. 20 mg/kg/day showed the greatest protection following MPTP treatment.

TABLE 14

Monoamine and metabolite levels

| Region | Dose (mg/kg) | Levels Mean +/− SD | P value | % difference |
|---|---|---|---|---|
| Dopamine | 0 | 0.8830 ± 0.3168 | NA | NA |
| | 1 | 1.202 ± 0.3910 | 0.0074 | +136 |
| | 5 | 2.497 ± 0.6475 | <0.0001 | +283 |
| | 10 | 3.908 ± 0.9202 | <0.0001 | +443 |
| | 20 | 8.386 ± 1.344 | <0.0001 | +950 |
| | Control | 12.02 ± 1.943 | <0.0001 | +1361 |
| DOPAC | 0 | 0.2145 ± 0.08036 | NA | NA |
| | 1 | 0.3030 ± 0.09937 | 0.0037 | +141 |
| | 5 | 0.5915 ± 0.1579 | <0.0001 | +276 |
| | 10 | 0.9740 ± 0.2344 | <0.0001 | +454 |
| | 20 | 2.109 ± 0.3608 | <0.0001 | +983 |
| | Control | 3.354 ± 0.7365 | <0.0001 | +1564 |

TABLE 14-continued

Monoamine and metabolite levels

| Region | Dose (mg/kg) | Levels Mean +/− SD | P value | % difference |
|---|---|---|---|---|
| HVA | 0 | 0.08685 ± 0.03286 | NA | NA |
| | 1 | 0.1205 ± 0.03791 | 0.0048 | +139 |
| | 5 | 0.2495 ± 0.06460 | <0.0001 | +287 |
| | 10 | 0.3970 ± 0.09381 | <0.0001 | +457 |
| | 20 | 0.8440 ± 0.1399 | <0.0001 | +972 |
| | Control | 1.210 ± 0.2017 | <0.0001 | +1393 |

Figure 22:
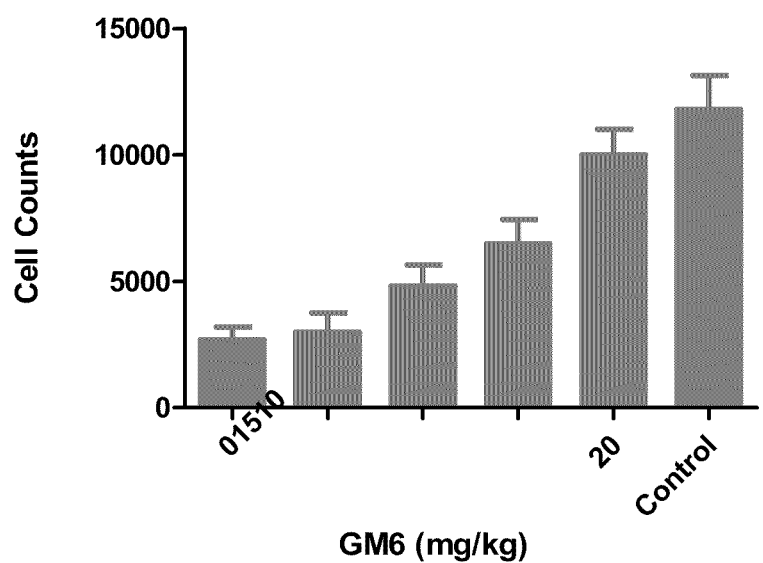
FIG. 22. Number of cells in the Substantia nigra pars compacta of mice following PD induction and GM6 treatment. Male C57BL/6 mice were injected with MPTP followed by GM6 at the indicated doses for 5 days. Animals were evaluated for cell counts at the end of the study.

Cell Counts. Following the behavioral studies, the animals were sacrificed at 7 days and ½ of the brain was taken and stained for tyrosine hydroxylase (TH) positive neurons in the substantia nigra pars compacta (SNpc). MPTP selectively kills these neurons and this is an excellent marker to determine the effect of GM6 on attenuation of the disease. The numbers of cells in the SNpc were determined by counting the TH positive neurons and are shown in Table 15 and FIG. 22. As seen in the table and figure, as the dose of GM6 increased, the number of cells (prevented the cell loss) in the brain. This suggests that GM6 protects the brain from the detrimental effects of PD induction.

TABLE 15

Cell counts

| Region | Dose (mg/kg) | Cell Counts Mean +/− SD | P value | % difference |
|---|---|---|---|---|
| SNpc | 0 | 2698 ± 510.6 | NA | NA |
| | 1 | 2988±763.3 | 0.3314 | +111 |
| | 5 | 4820±823.2 | <0.0001 | +179 |
| | 10 | 6494±944.1 | <0.0001 | +241 |
| | 20 | 9993± 1025 | <0.0001 | +370 |
| | Control | 11797±1339 | <0.0001 | +437 |

MNTF is a trophic factor that may provide protection from neurological diseases and allow for regeneration of neuronal tissue following injury or grafting. The studies performed here demonstrate the efficacy of the 6 amino analog of MNTF (GM6) to attenuate PD in a mouse model. Intravenous administration of GM6 at 1, 5, 10 and 20 mg/kg bolus dose over a five day period demonstrated and dose dependent decrease in PD behavior, biochemistry and histology. This demonstrated that GM6 is effective in limiting the extent of PD in the mouse via intravenous administration and can be beneficial for treating this disease.

When administered intravenously, GM6 was found to be efficacious in a mouse model of PD. The effectiveness of GM6 was dose dependent and indicates that GM6 can be beneficial in PD.

Example 5B

Testing of MNTF in a Cell Culture Model of Parkinson's Disease

MNTF was tested for efficacy in a cell culture model of Parkinson's disease (PD). In order to determine the efficacy of MNTF in the PD cell culture model, SH-SY5Y cells were subjected to salsolinol (100 μM) exposure for 24 hours. Cells were treated with and without MNTF at different concentrations and examined for cell viability. Salsolinol induced cell death in SH-SY5Y cells after 24 hours of exposure. Addition of MNTF to the cultures showed a dose dependent protection from salsolinol exposure. In addition, treatment with wortmannin (PI3K inhibitor) abrogated the effects of MNTF. These data demonstrated that MNTF is neuroprotective in a cell culture model of PD and following administration of salsolinol and can function through a PI3K pathway.

Abbreviations/Terminology for this Example.

"MNTF" means motorneuron trophic factor.

"PD" means Parkinson's disease.

"GB" means Genervon Biopharmaceuticals, LLC.

"CV" means cell viability.

"GM" means MNTF.

"WRT" means wortmannin.

"Sal" means salsolinol.

A number of studies have demonstrated the efficacy of the MNTF in various rat nerve systems, including the peripheral sciatic nerve, the peripheral musculocutaneous nerve, the cranial facial nerve, the cranial hypoglossal nerve, and the portion of the spinal cord that controls muscles in the neck, chest and upper limbs (Wang et al., 1995). Additionally, the wobbler mice (NIH) with double recessive genes given one dose of 35 ng MNTF at the age of six weeks stopped the neurodegenerative genetic disease in this strain.

Independent research groups using their own established assays and protocols conducted the following CNS and PNS experiments: 1. In a study of GM6 blood brain barrier penetration, intravenous administration of GM6 at 0.2 and 2 mg/kg single bolus dose demonstrated a dose dependent increase in GM6 levels in the brain after 4 hours. 2. In a middle cerebral artery occlusion (MOAC) mouse stroke model, post treatment of GM6 by IV injection reduced infarct volume in the brain and reduced neurological deficit in a dose response manner. High dose of GM6 reduced brain infarct volume by 74% compared with vehicle and reduced neurological deficits significantly, $p<0.0001$. 3. L-2-hydroxyglutaric acid (LGA) induces oxidative stress and apoptosis in the nervous system. In a zebrafish bioassay GM6 protected LGA-induced apoptosis in the CNS and reduced apoptosis by 85% in the midbrain. 4. In a rat sciatic nerve transection with a 8 mm gap study, GM6 treated animals have significant improvement of motoneuron regeneration in a dose response manner ($p<0.0002$ at the optimal dose) and promoted DRG neurons regeneration. 5. In a transected femoral nerve rat model, the number of motoneurons projected correctly to muscle in the GM6 treated animals in a dose response manner. At the optimal dose, the number of motoneurons projected correctly to muscle is three times the number of motoneurons projected incorrectly to the skin ($p<0.0001$). 6. In a zebrafish bioassay GM6 protected LGA-induced apoptosis in the PNS and reduced apoptosis by 49% in the peripheral neuromuscular junctions. 7. Cerebrospinal fluid (CSF) from patients with CNS disorders contains soluble factors, which induce neurite breakdown and neuronal death. GM6 enhanced cell survival significantly in the CSF of patients with Huntington Disease (271%), MS (246%), Stroke (205%), Parkinson (198%), Alzheimer (191%) and ALS (175%). These data suggest that MNTF is capable of protecting neuronal cells against cell death stimulated by CSF of patients with neurological disorders, a strong confirmation of our animal findings.

The efficacy of GMP grade GM6 (referred to as MNTF in this report) in a cell culture model of Parkinson's disease (Shavali et al., 2003). This study was performed to test the ability of MNTF to protect the SH-SY5Y cells from damage. The MNTF was provided as a solid and formulation was prepared (solution stored at 4° C.).

Methods and Materials

Cells

SH-SY5Y cells were purchased from American Type Culture Collection (Manassas, Va.) and cultured in a complete media containing minimum essential media, Hams F-12 media and Hanks Balanced Salt Solution Gibco-BRL) in a ratio of 2:1:1. The media also contained 10% fetal bovine serum along with penicillin (50 U/ml) and streptomycin (50 mg/ml). The cells were cultured in flasks and kept in a humidified incubator containing 5% CO2 in air at 37° C. The media was changed every 2-3 days.

Experimental Groups

Prior to manipulation, cultures were assigned to different treatment groups based on a randomized block design. The investigators were blinded to the treatment groups.

Induction of Cell Model of Parkinson's Disease.

For cell viability experiments, SH-SY5Y cells (0.5×105/well) were cultured in a 96-well cell culture plate and treated with (±) SAL (Sigma, St. Louis, Mo.) alone or along with different concentrations of (GM6) (Genervon), with or without Wortmannin (WRT) (Sigma, St. Louis, Mo.), a phosphatidylinositol-3-kinase (PI-3 kinase) inhibitor, for 24 h. Cell viability was determined by Thiazolyl blue (MTT) assay.

Statistical Analysis

The results were expressed as mean±SD and the statistical significance was calculated by the Student's t-test using Sigma-stat software, where $P<0.05$ was considered a significant value.

PD Cell Culture Model:

| Group | No. of cultures | Compound | Dose |
|---|---|---|---|
| 1 | 10 | Vehicle | 0 |
| 2 | 10 | GM6 | 0.1 mg/ml |
| 3 | 10 | GM6 | 1 mg/ml |
| 4 | 10 | GM6 | 10 mg/ml |
| 5 | 10 | GM6/WRT | 10 mg/ml + WRT (10 µM) |
| 6 | 10 | Sal | 100 µM |
| 7 | 10 | Sal/GM6 | 100 µM/0.1 mg/ml |
| 8 | 10 | Sal/GM6 | 100 µM/1 mg/ml |
| 9 | 10 | Sal/GM6 | 100 µM/10 mg/ml |
| 10 | 10 | Sal/GM6/WRT | 100 µM/10 mg/ml + WRT (10 µM) |

Endpoints

Cell Number

All test groups have been provided to NTS; MNTF was provided as a solid material to NTS. All cultures in the test groups were dosed as indicated above. Salsolinol and Wortmannin were purchased from Sigma. GM6 Exemplary MNTF FSRYAR SEQ ID NO: 2.

Results

Cell culture model of PD. PD study. The relative changes in cell viability were assessed in SH-SY5Y cells when cultured with GM6±salsolinol (Sal). Data were from cell cultures that were treated with vehicle or MNTF (GM6).

Cell Viability. Cell cultures were incubated with various concentrations of GM6 (0.1 to 10 mg/ml)±salsolinol (100 µM) and Wortmannin (WRT, 10 µM) and the cell number was determined. Based on the data obtained, GM6 showed a dose dependent increase in cell number compared to the control treated cells. At 10 mg/ml there was a 19.2% increase in the cell number compared to control treated cells. Treatment of the cells with Wortmannin at 10 mM prevented the increase in cell number suggesting a role for PI3K in the actions of GM6.

Figure 17:
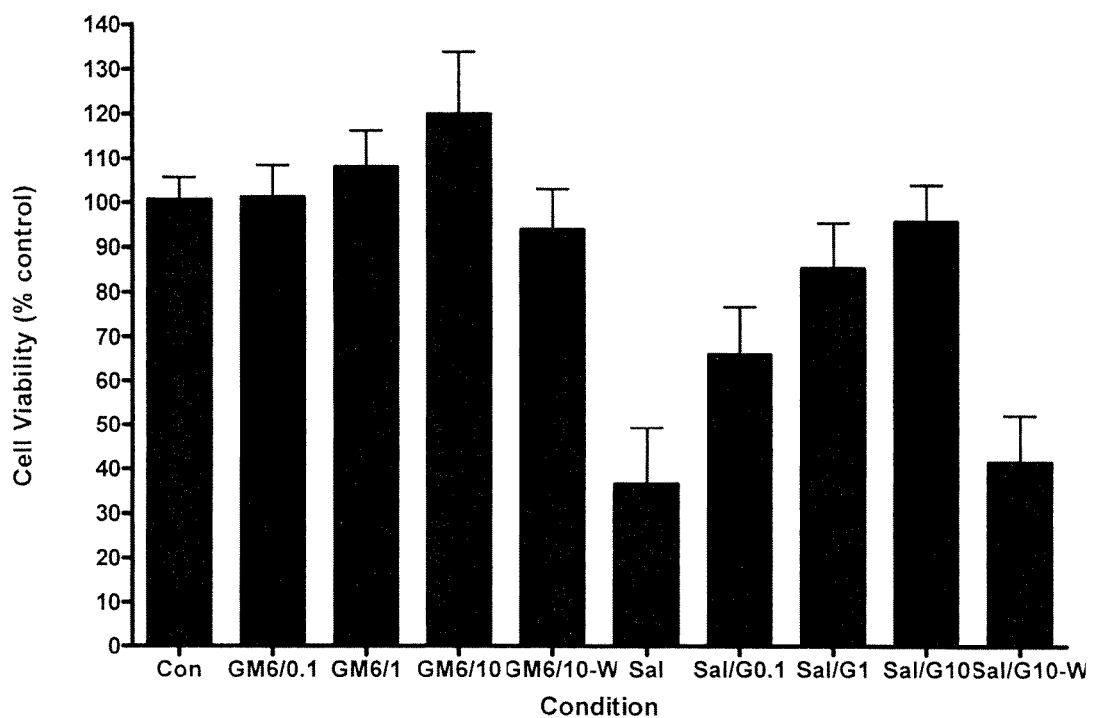
FIG. 17. Effects of exemplary MNTF peptide analog (GB test articles) on cell viability in SH-SY5Y neuronal cells following salsolinol treatment. All cultures were grown in media as outlined in the methods section. Cultures were incubated with vehicle (control), MNTF peptide analog GM6 at various concentrations, +/−salsolinol (Sal). In addition, several cultures were incubated with Wortmannin (W) to determine the mechanism of action. Cultures were incubated for 24 hours with compounds and analyzed for cell viability.

Treatment of the cells with salsolinol at 100 µM demonstrated a decreased cell viability in dopaminergic SH-SY5Y cells. There was a 63.7% decrease in the number of cells after 24 hour treatment with salsolinol. Addition of GM6 to the cells prevented Sal induced cell death and significantly increased cell survival, as assessed by MTT assay. SAL, at 100 µM concentration, decreased cell viability to 36.5%, and co-treatment with GM6 at 0.1, 1.0 and 10.0 mg/ml, increased cell viability up to 66%, 85% and 95%, respectively (FIG. 17). WRT (10 µM) blocked the neuroprotective effects of GM6 (FIG. 17).

TABLE 16

Percent change in cell viability following GM6 and Salsolinol treatment.

| Group | Dose | Treatment | Compound | Viability (% Cells) Mean ± SD | Percent Change in Cell number | P-value |
|---|---|---|---|---|---|---|
| 1 | 0 mg/ml | Vehicle | Vehicle | 100.6 ± 5.187 | NA | NA |
| 2 | 0.1 mg/ml | GM6 | Vehicle | 101.2 ± 7.260 | +0.6%** | 0.8394** |
| 3 | 1 mg/ml | GM6 | Vehicle | 108.0 ± 8.249 | +7.4%** | 0.0283** |
| 4 | 10 mg/ml | GM6 | Vehicle | 119.9 ± 14.01 | +19.2%** | 0.0007** |
| 5 | 10 mg/ml | GM6 | WRT | 93.81 ± 9.246 | −6.7%** | 0.0576** |
| 6 | 0 mg/ml | Salsolinol | Vehicle | 36.48 ± 12.78 | NA | NA |
| 7 | 0.1 mg/ml | GM6/Sal | Vehicle | 65.85 ± 10.80 | +80.5%* | <0.0001* |
| 8 | 1 mg/ml | GM6/Sal | Vehicle | 85.19 ± 10.18 | +133.5%* | <0.0001* |
| 9 | 10 mg/ml | GM6/Sal | Vehicle | 95.57 ± 8.328 | +162%* | <0.0001* |
| 10 | 10 mg/ml | GM6/Sal | WRT | 41.35 ± 10.79 | +13.4%* | 0.3689* |

*Percent change in cell number for Groups 7-10 are compared to Salsolinol treated cells (Group 6).
**Percent change in cell number for Groups 2-5 are compared to Vehicle treated cells (Group 1).

Salsolinol (Sal) was added at 100 µM, Wortmannin (WRT) was added at 10 µM. MNTF (GM) is a trophic factor that can provide protection from neurological diseases and allow for regeneration of neuronal tissue following injury or grafting. The studies performed here demonstrate the ability of MNTF to protect the dopaminergic neurons (SH-SY5Y cells) from the detrimental effects of PD (salsolinol) in an effective and efficient way. Administration of MNTF at 0.1, 1 and 10 mg/ml for 24 hours demonstrated a dose dependent protective effect in the SH-SY5Y cells against cell death by salsolinol by an increase in cell number. These studies demonstrated that MNTF can have a beneficial effect in PD.

When administered MNTF (GM6) was found to be protective against a PD cell culture model of cell death (salsolinol induced apoptosis).

Example 6

Testing of MNTF in Protection Against CSF Injury

GM6 was tested for efficacy in a model of neuronal injury. Five disease specific human patients cerebrospinal fluid (CSF) samples from control group and each of the eight neurological disorders groups were tested in primary neuronal cells to determine the effects on neuronal cell death. In addition, the effects of GM6 were examined for protection against the injury induced by the CSF. CSF from disease specific human of eight different neurological diseases induced neuronal cell death when applied as a 10% solution. GM6 provided protection from this injury. These studies demonstrate that CSF from human with neurological disorders contains certain factors that induce cell death and that GM6 can protect against these effects. These studies further demonstrate the effectiveness of GM6 in models of neurological diseases.

Abbreviations/Terminology for this Example.
"MNTF" means motorneuron trophic factor.
GM6" and "6mer" each mean exemplary 6 amino acid peptide analog of MNTF: FSRYAR (SEQ ID NO: 2).
"CSF" means cerebrospinal fluid.
"Genervon" and "GB" each mean Genervon Biopharmaceuticals, LLC.
"NCC" means neuronal cell cultures.
Testing of MNTF in Protection Against CSF Injury.

Using the post mortem CSF samples from five disease specific patients/donors of each of the nine study groups along with identification and clinical diagnosis and neuropathology diagnosis documents supplied by UCLA Human Brain and Spinal Fluid Resource Center (Los Angeles, Calif.), a study was conducted to assess the ability of MNTF peptide in protection of CSF injury. CSF samples were tested in primary neuronal cells to determine the effects on neuronal cell death. In addition, the effects of MNTF6mer/GM6 were examined for protection against the injury induced by the CSF. GM6 is chemically synthesized under GMP compliance (CS Bio Co., Menlo Park, Calif., GMP013, lot C811). This study was performed under contract with Neurological Testing Service, Inc. (NTS, Charleston, S.C.). The GM6 was provided to NTS as a solid and formulation prepared by NTS (solution stored at 4° C.).

Methods and Materials
Study Design
Sprague Dawley rat cortical neuronal cells were isolated from 18-day-old embryonic fetuses and growth in culture for 12 days. Post mortem CSF from control and various neurological disorders donors were applied to the cultures and examined for neuronal viability. In addition, MNTF was added to the cultures to protect the cells from injury.

In Vitro Methods
Neuronal cultures were prepared from 18-day-old Sprague-Dawley rat fetuses. Fetal rat midbrains were dissected and incubated for 15 min in a solution of 2 mg/mL trypsin in Ca2+- and Mg2+-free Hanks' balanced salt solution (HBSS) buffered with 10 mM HEPES (GIBCO Life Technologies, Paisley, Scotland). The tissue was then exposed for 2 min to soybean trypsin inhibitor (1 mg/mL in HBSS) and rinsed three times in HBSS. Cells were dissociated by trituration and distributed to 96-well or 24-well poly-L-lysine-coated plastic culture plates (Costar, Cambridge, Mass.). Initial plating densities were approximately 160-180 cells/mm2. At the time of plating, each well contained 0.2 ml of DMEM/F12 medium (GIBCO Life Technologies, NY) supplemented with 100 mL/L fetal bovine serum (Sigma Chemicals, St. Louis, Mo.). After a 24-hr period, the DMEM/F12 medium was replaced with 0.15 mL of 2% v/v B-27 Neurobasal medium supplemented with 2 mM GlutaMAX and 0.5% w/v D-(+) glucose (GIBCO Life Technologies). Twice a week, two-thirds of the Neurobasal medium was replaced with freshly prepared medium of the same composition. Cultures were used for neurotoxicity experiments after 12 days in culture. The research investigators at NTS were unaware of the material prior to, during the study and when the preliminary data were presented to the Sponsor (GB).

UCLA Human Brain and Spinal Fluid Resource Center (Los Angeles, Calif.) supplied the post mortem CSF samples from five donors of each of the nine study groups along with identification and clinical diagnosis and neuropathology diagnosis documents. Samples were stored at −170° C. prior to shipment and were shipped with dry ice. The study groups were control (no neurological disorder), Amyotrophic Lateral Sclerosis (ALS), Neuropathy (NP), Multiple Sclerosis (MS), Alzheimer's Disease (AD), Batten's Disease (BD), Huntington's Disease (HD), Parkinson's Disease (PD), and Cerebral Ischemia (stroke).

To test the effects of CSF on neuronal cell survival, CSF was added to the cultures in Neurobasal medium containing 10% CSF. CSF was added to the cultures and examined after 48 hours. Images of cultures were taken and then the cultures were subjected to MTT assay (see below) to determine the % cell death. Additional cultures were incubated with MNTF (100 nM) added to the cultures 2 hours prior to addition of CSF.

MTT assay. Viability of primary neurons was determined as described. The relative number of surviving cells was determined in triplicate using the value for cells stimulated with vehicles as 100%. Cell survival was assessed on the 2nd day of treatment via an MTT assay. MTT (3-[4,5-dimethylthiazol-2-yl]-2,5-diphenyltetrazolium bromide) was diluted to 200 mM in Hanks' solution (Biochrom) and added to cultures for two hours at 37° C. The MTT formazan product was released from the cells by adding dimethylsulfoxide, and measured at 570 nm in an Ultrospect III spectrophotometer (Pharmacia). Relative survival in comparison to untreated controls could then be determined.

Statistical analysis. The results are expressed as the mean±standard deviation (SD). The significance of difference in the data was analyzed using a t-test.

Treatment Groups.
Neuronal Injury Model

| Group | Compound | Dose | Route |
|---|---|---|---|
| 1 Control | CSF | 10% | In vitro |
| 2 ALS | CSF | 10% | In vitro |
| 3 NP | CSF | 10% | In vitro |
| 4 MS | CSF | 10% | In vitro |
| 5 AD | CSF | 10% | In vitro |
| 6 BD | CSF | 10% | In vitro |
| 7 HD | CSF | 10% | In vitro |
| 8 PD | CSF | 10% | In vitro |
| 9 Stroke | CSF | 10% | In vitro |

MNTF Effects

| Group | Compound | Dose | Route |
|---|---|---|---|
| 1 Control + MNTF | CSF | 10% (100 nM) | In vitro |
| 2 ALS + MNTF | CSF | 10% (100 nM) | In vitro |
| 3 NP + MNTF | CSF | 10% (100 nM) | In vitro |
| 4 MS + MNTF | CSF | 10% (100 nM) | In vitro |
| 5 AD + MNTF | CSF | 10% (100 nM) | In vitro |
| 6 BD + MNTF | CSF | 10% (100 nM) | In vitro |
| 7 HD + MNTF | CSF | 10% (100 nM) | In vitro |
| 8 PD + MNTF | CSF | 10% (100 nM) | In vitro |
| 9 Stroke + MNTF | CSF | 10% (100 nM) | In vitro |

*Parentheses indicates dose of MNTF.

Code
"ALS" means amyotrophic lateral sclerosis.
"NP" means neuropathic pain.
"MS" means multiple sclerosis.
"AD" means Alzheimer's disease.
"BD" means Batten's disease.
"HD" means Huntington's disease.
"PD" means Parkinson's disease.
"Stroke" means Cerebral ischemia.

Results

CSF in neuronal cell cultures—Study. The effects of CSF on neuronal cell death were assessed in an in vitro model of neuronal cell injury. CSF was added to primary rat neuronal cell cultures at 10% of total volume. Cells were examined by microscopic analysis and by MTT assay for cell death.

Microscopic Analysis

Neuronal cell cultures were treated with 10% CSF from control or various neurological disorders donors for 48 hours and then assessed for cell loss. Control CSF did not have a significant effect on cell survival, while treatment of cells with CSF from neurological disorders induced cell death.

MTT Assay

Figure 18:
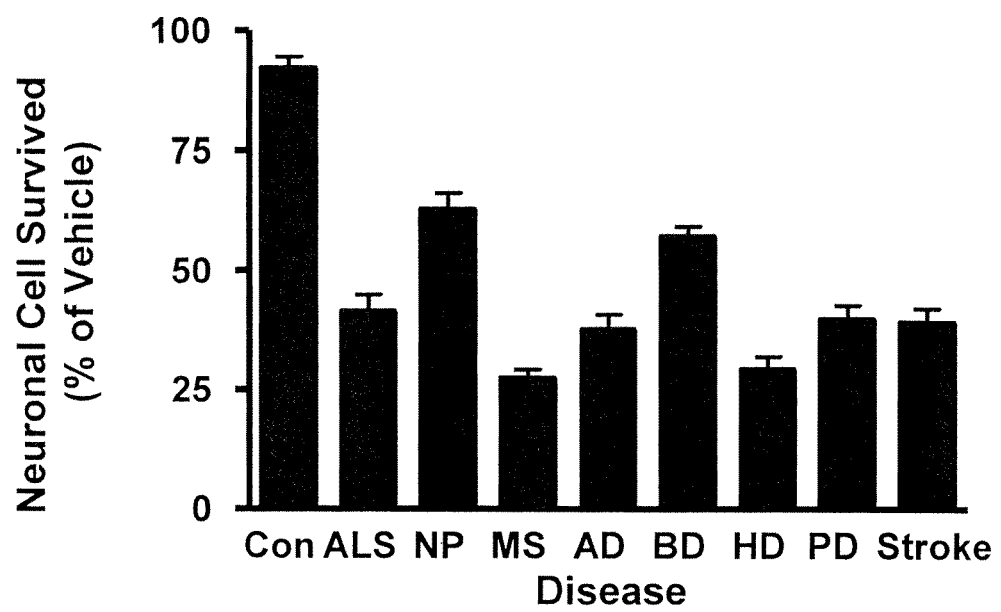
FIG. 18. Induction of cell death in primary neuronal cell cultures by CSF. CSF from control and various neurological disorders was applied to primary rat neuronal cell cultures for 2 days after 12 days in culture. The indicated test articles were administered at time 0 and the cultures were examined by MTT assay for cell viability.

To measure the percent of cell loss induced by CSF in rat primary neuronal cell cultures, cultures were analyzed by MTT assay. As seen in FIG. 18, CSF from control patients did not induce any appreciable cell death when compared to control samples. However, the CSF from the various neurological disorders induced cell death resulted in varying degrees of cell loss (Table 17 and FIG. 18). As seen in the figure and table, MS induced the greatest cell loss (70%) while NP induced the least amount of cell death (32%). These data suggest that neurological disorders stimulate or result in the release of compounds that induce or exacerbate neuronal cell loss.

TABLE 17

Neuronal cell loss induced by CSF.

| CSF | Dose | % Cell Survived (Mean ± SD) | P value (% decrease) |
|---|---|---|---|
| Control | 10% | 92.00 ± 9.181 | 0 (0) |
| ALS | 10% | 41.33 ± 13.76 | <0.0001 (55) |
| NP | 10% | 62.73 ± 13.42 | <0.0001 (32) |
| MS | 10% | 27.40 ± 7.149 | <0.0001 (70) |
| AD | 10% | 37.53 ± 12.45 | <0.0001 (59) |
| BD | 10% | 57.00 ± 8.443 | <0.0001 (38) |
| HD | 10% | 29.40 ± 10.35 | <0.0001 (68) |
| PD | 10% | 39.67 ± 11.45 | <0.0001 (57) |
| Stroke | 10% | 39.07 ± 11.13 | <0.0001 (57.5) |

Effects of MNTF on CSF in neuronal cell cultures. The effects of MNTF on CSF on neuronal cell death were assessed in an in vitro model of neuronal cell injury. MNTF was added at 100 nM to the cell cultures 2 hours prior to the addition of CSF. CSF was added to primary rat neuronal cell cultures at 10% of total volume. Cells were examined by microscopic analysis and by MTT assay for cell death.

Microscopic Analysis

Neuronal cell cultures were treated with 100 nM MNTF for 2 hours then 10% CSF from control or various neurological disorders was added for 48 hours and then assessed for cell loss. MNTF did have a significant effect on cell survival with prior treatment of cells to CSF.

MTT Assay

Figure 2B:
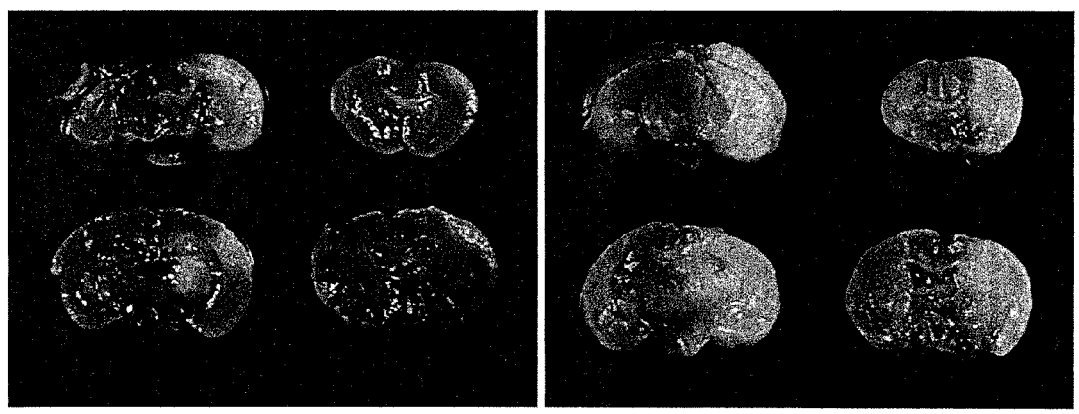
FIG. 2B. Images of two brains subject to ischemia/reperfusion injury followed by IV injection of one dose of GM602 (4 sections of the treated brained on left) showing very little damage (white area) or vehicle (4 sections of the control brain on right) showing extensive damage in the brain. Representative pictures of brains from mice subject to 1 hr ischemia and 24 hr reperfusion. Animals were injected with GM602 (5 mg/kg) or vehicle at the end of ischemia.
Figure 3:
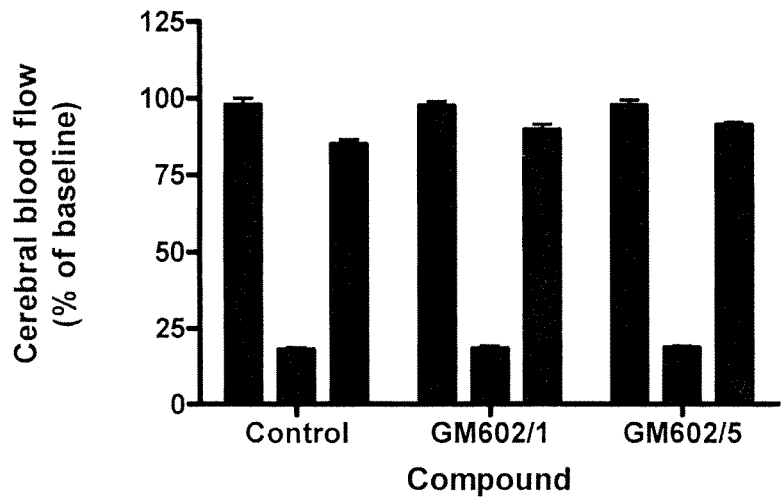
FIG. 3. Illustrates the data from the assessment of the cerebral blood flow from animals subjected to ischemia/reperfusion injury. All mice were subjected to 1 hour of cerebral ischemia followed by 24 hours of reperfusion. Animals were injected with vehicle (control) or GM602 at 1 mg/kg or 5 mg/kg intravenously at the end of ischemia. For each study group, blood flow was measured before ischemia (first column), during ischemia (second column) and after injection of test articles (third column).
Figure 4:
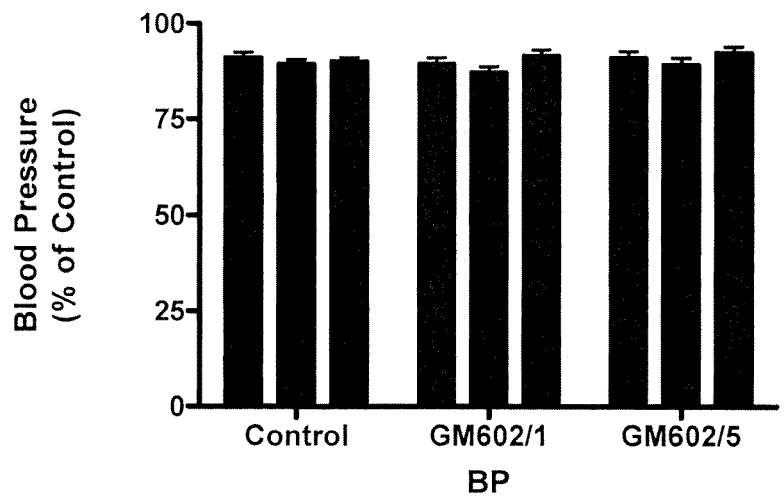
FIG. 4. Blood pressure measurement in mice subjected to ischemia/reperfusion injury. All mice were subjected to 1 hour of cerebral ischemia followed by 24 hours of reperfusion. Animals were injected with vehicle (control) or GM602 at 1 mg/kg or 5 mg/kg intravenously at the end of ischemia. For each study group, blood pressure was measured before ischemia (first column), during ischemia (second column) and after injection of test article (third column).
Figure 5:
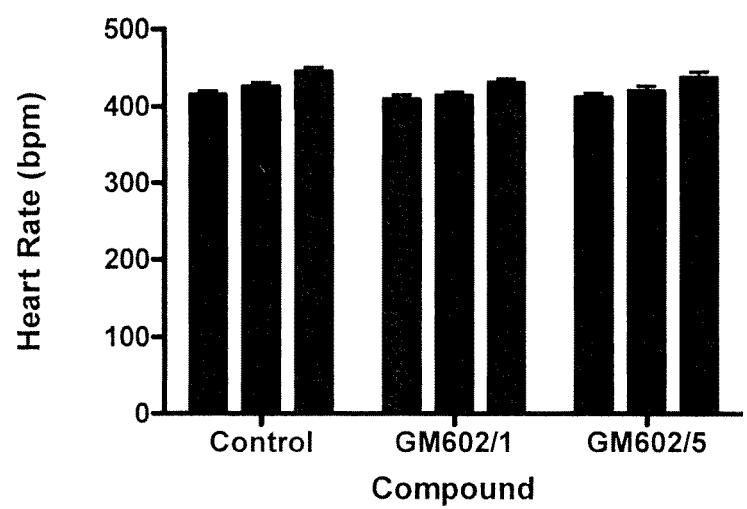
FIG. 5. Heart rate measurements in mice subject to ischemia/reperfusion injury. All mice were subjected to 1 hour of cerebral ischemia followed by 24 hours of reperfusion. Animals were injected with vehicle (control) or GM602 at 1 mg/kg or 5 mg/kg intravenously at the end of ischemia. For each study group, heart rate was measured before ischemia (first column), during ischemia (second column) and after injection of test article (third column).
Figure 7:
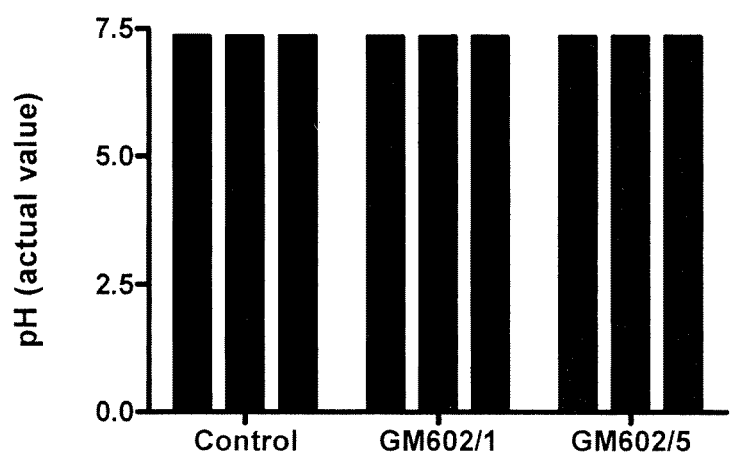
FIG. 7. pH measurement in mice subject to ischemia/reperfusion injury. All mice were subjected to 1 hour of cerebral ischemia followed by 24 hours of reperfusion. Animals were injected with vehicle (control) or GM602 at 1 mg/kg or 5 mg/kg intravenously at the end of ischemia. For each study group, pH was measured before ischemia (first column), during ischemia (second column) and after injection of test article (third column).
Figure 19:
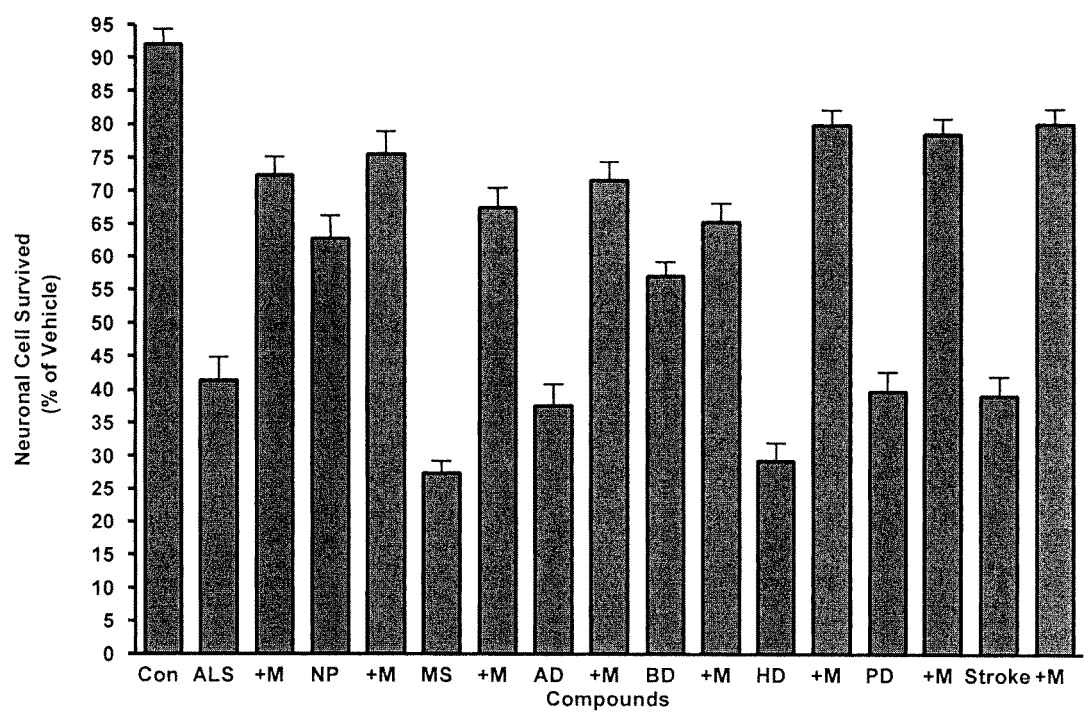
FIG. 19. Protective effects of an exemplary MNTF peptide against neuronal cell loss in CSF induced cell death. CSF from control and various neurological disorders was applied to primary rat neuronal cell cultures for 2 days after 12 days in culture. MNTF (+M) was added 2 hours prior to the addition of CSF. The indicated test articles were administered at time 0 and the cultures were examined by MTT assay for cell viability.
Figure 20A:
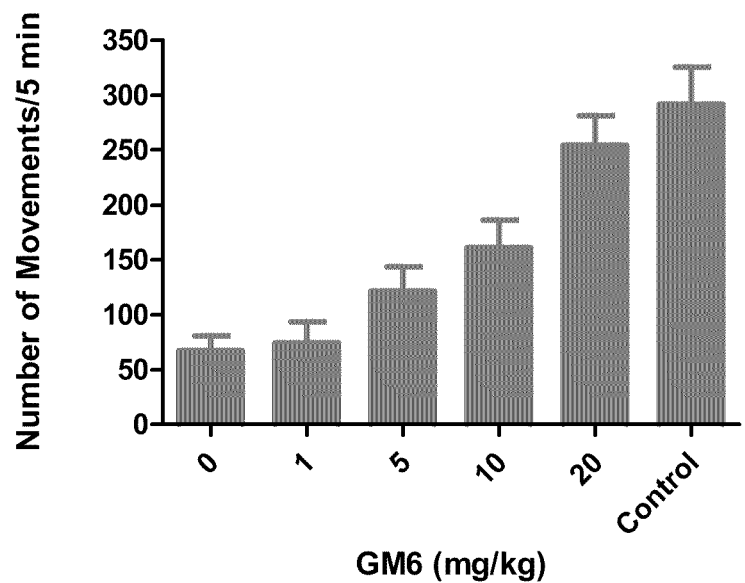
FIGS. 20A and 20B. Behavioral determinations in mice following PD induction and GM6 treatment. Male C57BL/6 mice were injected with MPTP followed by GM6 at the indicated doses for 5 days. Animals were evaluated for behavioral changes.
Figure 20B:
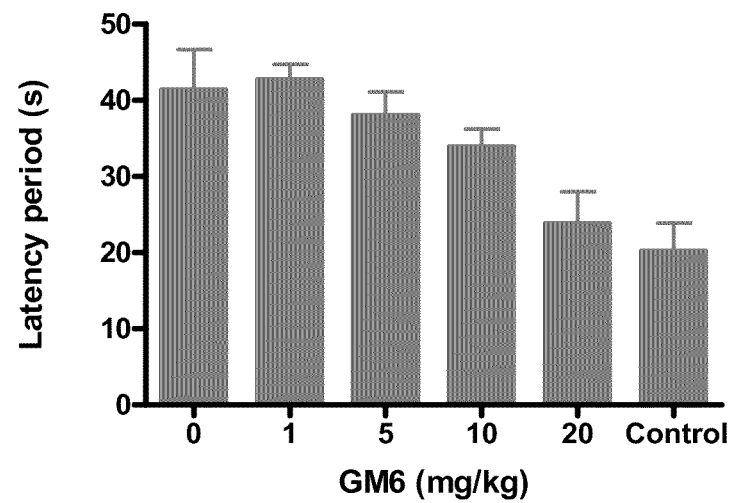

To measure the percent of cell protection induced by MNTF on CSF treated rat primary neuronal cell cultures, cultures were analyzed by MTT assay. As seen in FIG. 2, MNTF provided a level of protection to the neuronal cell cultures on cell death induced by CSF from control patients with neurological disorders (Table 18 and FIG. 19). As seen in the FIG. 19 and Table 18, MNTF enhanced cell survival the greatest in HD CSF (271%), significantly in the CSF of MS (246%), Stroke (205%), Parkinson (198%), Alzheimer (191%) and ALS (175%), while MNTF enhanced cell survival the least in BD CSF (114%). These data suggest that MNTF is capable of protecting neuronal cells against cell death stimulated by CSF of patients with neurological disorders.

TABLE 18

Neuronal cell protection elicited by MNTF.

| CSF | Dose | % Cell Survived (Mean ± SD) | P value (% decrease (↓) or increase (↑)) |
|---|---|---|---|
| Control | 10% | 92.00 ± 9.181 | 0 (0) |
| ALS | 10% | 41.33 ± 13.76 | <0.0001 (55↓) |
| ALS + MNTF | 10% + 100 nM | 72.33 ± 10.83 | <0.0001 (175↑) |
| NP | 10% | 62.73 ± 13.42 | <0.0001 (32↓) |
| NP + MNTF | 10% + 100 nM | 75.47 ± 13.22 | <0.014 (120↑) |
| MS | 10% | 27.40 ± 7.149 | <0.0001 (70↓) |
| MS + MNTF | 10% + 100 nM | 67.33 ± 11.65 | <0.0001 (246↑) |
| AD | 10% | 37.53 ± 12.45 | <0.0001 (59↓) |
| AD + MNTF | 10% + 100 nM | 71.53 ± 10.81 | <0.0001 (191↑) |
| BD | 10% | 57.00 ± 8.443 | <0.0001 (38↓) |
| BD + MNTF | 10% + 100 nM | 65.20 ± 11.04 | <0.03 (114↑) |
| HD | 10% | 29.40 ± 10.35 | <0.0001 (68↓) |
| HD + MNTF | 10% + 100 nM | 79.80 ± 8.768 | <0.0001 (271↑) |
| PD | 10% | 39.67 ± 11.45 | <0.0001 (57↓) |
| PD + MNTF | 10% + 100 nM | 78.53 ± 8.806 | <0.0001 (198↑) |
| Stroke | 10% | 39.07 ± 11.13 | <0.0001 (57.5↓) |
| Stroke + MNTF | 10% + 100 nM | 80.07 ± 8.548 | <0.0001 (205↑) |

MNTF is a trophic factor that may provide protection from neurological diseases and allow for regeneration of neuronal tissue following injury or grafting. The studies performed here demonstrate the ability of the 6 amino analog of MNTF (GM6) to protect against the detrimental effects of neurological disorder CSF on neuronal injury. In vitro application of GM6 at 100 nM dose demonstrated protection of neuronal cells in most cases. This demonstrated that GM6 has a protective effect against a variety of neurological disorders.

When administered in vitro to neuronal cells, GM6 was found to be protective against CSF from neurological diseases.

Example 7

MS Model

GM6 (CS Bio Co., Menlo Park, Calif.) was tested for efficacy in a mouse multiple sclerosis (MS) model. In order to determine the efficacy of GM6 in MS, mice were injected with myelin proteolipid protein (PLP) to induce MS and then intravenously with GM6 at several doses to determine the influence on attenuation of MS. Intravenous (i.v.) administration of GM6 (1, 5, 10 or 20 mg/kg) at seven doses (once per day) was examined. Administration of GM6, demonstrated a dose dependent attenuation of MS in the mice with 20 mg/kg showing the most efficacy. Both clinical and histological analysis demonstrated the attenuation illustrating a unique effect for GM6 in MS. These data suggest that GM6 is effective in the mouse model of MS following i.v. injection and may be a potential treatment for MS patients. Abbreviations/Terminology for this Example.

"MNTF" means motorneuron trophic factor.

"GM6" and "6mer" each mean exemplary 6 amino acid peptide analog of MNTF.

"MS" means multiple sclerosis.

"EAE" means experimental autoimmune encephalomyelitis.

"PLP" means myelin proteolipid protein.

"Genervon" and "GB" each mean Genervon Biopharmaceuticals, LLC.

"I.V." means intravenous.

This experimental design is to assess the ability of the 6 amino acid analog (GM6) of Motoneurontrophic factor (MNTF) to determine the efficacy of GM6 in a mouse model of multiple sclerosis. GB test article is a synthesized 6 amino acid peptide (MNTF) (CS Bio Co., Menlo Park, Calif.).

Assessment of the efficacy of GM6 in a mouse model of MS via intravenous injection.

Methods and Materials

Study design. Female SJL/J mice were injected with PLP as described below and examined for the protection from EAE induced MS by GM6 at the indicated doses. Animals were examined for clinical manifestations and histological changes.

Experimental Autoimmune Encephalomyelitis (EAE) Induction. Female SJL/J mice (8-10 weeks old, the Jackson Laboratory) were used in the experiments. EAE induction and treatment Myelin proteolipid protein (PLP) (p 139-151, HSLGKWLGHPDKF, SynPep Corporation) was used for immunization. EAE was induced in female SJL/J mice by subcutaneous injection with 25 μg PLP dissolved in complete Freund's adjuvant (CFA, Difco Laboratories). On the day of immunization and 48 h later, pertussis toxin (PT, List Biological laboratories, Inc) 200 ng in phosphate buffered saline (PBS) was injected into the mouse tail vein.

Administration of MNTF. Mice were randomly divided into: MNTF treatment groups (n=10/group): MNTF were administered intravenously for 7 consecutive days starting on the day of clinical symptom onset (score≥1), which makes this treatment protocol clinically relevant. The dose of MNTF was 1, 5, 10 or 20 mg/kg based on preliminary studies. EAE control group (n=10): EAE mice were treated with the same volume of saline used as experimental groups.

Clinical Observations. Mice were observed for clinical signs of EAE daily and weighed every second day. Clinical score was designated as follows: 0, no detectable signs of EAE; 1, affected tail tonus; 2, tail paralysis; 3, mild hindleg paresis; 4, severe hindleg paresis; 5, one hindleg paralysis; 6, complete hindleg paralysis; 7, complete hindleg paralysis and foreleg paresis; and 8, death.

For clinical EAE evaluation, the following parameters were used: day of onset was defined for each animal as the day of first appearance of EAE symptoms. EAE duration was calculated as the number of days each animal was scored sick divided by the total number of scored days and expressed as a percentage. Cumulative incidence was defined as the percentage of animals that developed EAE during the experimental period. Mean score over experimental period was calculated for each animal as the sum of all individual scores divided by the number of measurements. Maximum score was defined as the highest clinical score for each animal during the experimental period. If mice died from EAE throughout the course of the experiment, these mice were assigned a score of 8 at all following time points. If mice died before clear onset of EAE symptoms, these mice were excluded from the experiment. All animals, including severely EAE-affected animals, had access to food and water throughout the experiments.

Histology. Brains and spinal cords were removed 20 days later and fixed with 10% buffered formalin (Sigma). Paraffin-embedded sections (6 μm thick) were stained with H & E to assess the number of lesions in the brain and spinal cord. These were scored and recorded.

Statistical analysis. The results were expressed as the mean±standard deviation (SD). The significance of difference in the data was analyzed using a t-test.

Exclusion of Animals From the Study. Animals were excluded from the study based upon several criteria:

Animals that died prior to completion of study (at any point).

Animals developed severe complications following administration of test articles.

Treatment groups. All groups were subjected to GM6 or were controls. Animals (50 animals) were subjected to bolus i.v. dosing by tail vein of vehicle or MNTF at the indicated doses.

Mouse MS Model:

| Group SJL female mice | Compound | Dose (mg/kg) | Route |
|---|---|---|---|
| 1 (n = 10 mice) | Vehicle | 0 | IV |
| 2 (n = 10 mice) | MNTF | 1 mg/kg/day | IV |
| 3 (n = 10 mice) | MNTF | 5 mg/kg/day | IV |
| 4 (n = 10 mice) | MNTF | 10 mg/kg/day | IV |
| 5 (n = 10 mice) | MNTF | 20 mg/kg/day | IV |

Endpoints

Modulation of MS in the Mouse

All test groups have been provided to NTS; GM6 was provided as a solid material to NTS. All animals in the test groups were dosed as indicated above.

Results

Clinical Score. The efficacy of GM6 in a mouse model of MS was assessed. Data from mice that were i.v. administered with vehicle or GM6 (at indicated doses).

Clinical Analysis

Figure 23:
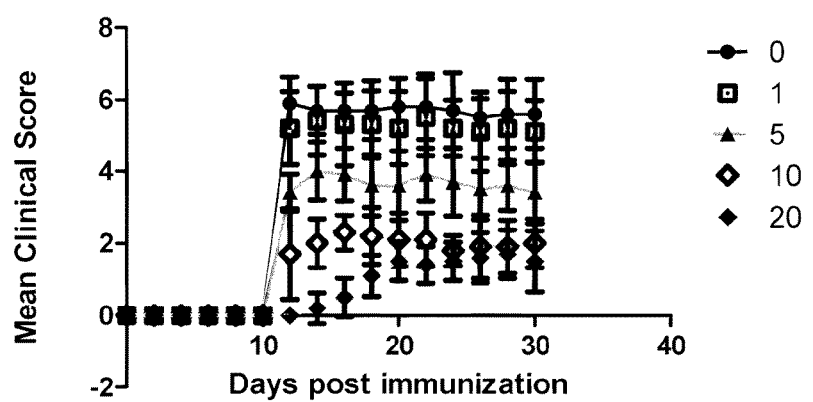
FIG. 23. Mean clinical scores in mice following MS induction and GM6 treatment. Female JJL/J mice were injected with PLP followed by GM6 at the indicated doses for 7 days. Animals were evaluated for clinical scores every other day.

GM6: After induction of MS with PLP, the mice were administered GM6 at the indicated doses (FIG. 23). Animals were examined at every other day starting on day 0 to determine the clinical score of the animals. Mice were injected with GM6 every day for seven days starting on the day of PLP injection. As seen in FIG. 23, the mice treated with vehicle showed a significant increase in clinical score. Treatment with GM6 showed a significant improvement (attenuation) of the disease (FIG. 23). GM6 at 5, 10 and 20 mg/kg showed a significant benefit, whereas the 1 mg/kg did not show any restitution. Table 20 shows the number of mice that developed acute disease following treatment with GM6. As seen in the table, the 10 and 20 mg/kg showed a reduction in the total number of mice in the acute disease state but not the chronic state.

TABLE 19

Significance of GM6 administration compared to Vehicle treated animals

| Treatment | P value |
|---|---|
| Vehicle | NA |
| GM6 (1 mg/kg) | NA |
| GM6 (5 mg/kg) | <0.01 |
| GM6 (10 mg/kg) | <0.001 |
| GM6 (20 mg/kg) | <0.001 |

TABLE 20

Mice with clinical signs/total number of mice (%) - acute disease

| Treatment | P value |
|---|---|
| Vehicle | 10/10 (100%) |
| GM6 (1 mg/kg) | 10/10 (100%) |
| GM6 (5 mg/kg) | 10/10 (100%) |
| GM6 (10 mg/kg) | 7/10 (70%) |
| GM6 (20 mg/kg) | 0/10 (0%) |

TABLE 21

Mice with clinical signs/total number of mice (%) - chronic disease

| Treatment | P value |
|---|---|
| Vehicle | 10/10 (100%) |
| GM6 (1 mg/kg) | 10/10 (100%) |
| GM6 (5 mg/kg) | 10/10 (100%) |
| GM6 (10 mg/kg) | 10/10 (100%) |
| GM6 (20 mg/kg) | 10/10 (100%) |

Mortality: There were no deaths in this study.

Figure 24A:
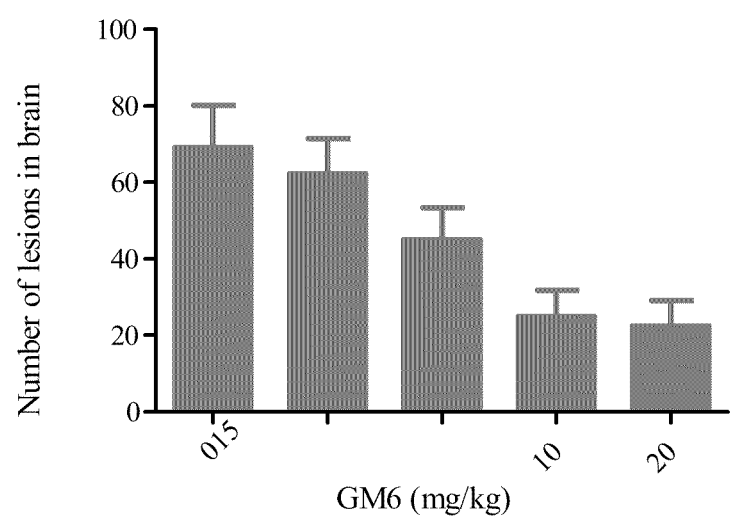
FIG. 24A, 24B: 24A. Number of lesions in the brains of mice following MS induction and GM6 treatment. Female JJL/J mice were injected with PLP followed by GM6 at the indicated doses for 7 days. Animals were evaluated for brain lesions at the end of the study. 24B. Number of lesions in the spinal cord of mice following MS induction and GM6 treatment. Female JJL/J mice were injected with PLP followed by GM6 at the indicated doses for 7 days. Animals were evaluated for spinal cord lesions at the end of the study.
Figure 24B:
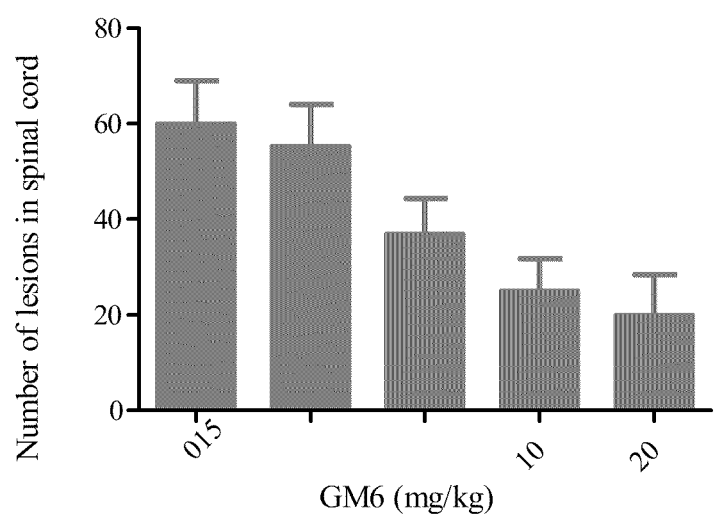

Lesion Number. The number of lesions in the brain and spinal cord were determined by counting and are shown in FIGS. 24A and 24B. As the dose of GM6 increased, the number of lesions in the brain and spinal cord decrease. This suggests that GM6 protects the brain and spinal cord from the detrimental effects of MS induction.

TABLE 22

| Region | Dose (mg/kg) | Lesion # Mean +/− SD | P value | % difference |
|---|---|---|---|---|
| Brain | 0 | 69.20 ± 10.99 | NA | NA |
| | 1 | 62.30 ± 9.202 | 0.1454 | −10 |
| | 5 | 45.00 ± 8.367 | <0.0001 | −35 |
| | 10 | 24.90 ± 6.871 | <0.0001 | −64 |
| | 20 | 22.40 ± 6.687 | <0.0001 | −68 |
| Spinal Cord | 0 | 59.90 ± 9.098 | NA | NA |
| | 1 | 55.20 ± 8.817 | 0.2560 | −8 |
| | 5 | 36.90 ± 7.385 | <0.0001 | −38 |
| | 10 | 24.50 ± 6.671 | <0.0001 | −59 |
| | 20 | 19.90 ± 8.517 | <0.0001 | −67 |

MNTF is a trophic factor that may provide protection from neurological diseases and allow for regeneration of neuronal tissue following injury or grafting. The studies performed here demonstrate the efficacy of the 6 amino analog of MNTF (GM6) to attenuate MS in a mouse model. Intravenous administration of GM6 at 1, 5, 10 and 20 mg/kg bolus dose over a seven day period demonstrated and dose dependent decrease in MS clinical scores and histology. This demonstrates that GM6 is effective in limiting the extent of MS in the mouse via intravenous administration and can be beneficial for treating this disease.

When administered intravenously, GM6 was found to be efficacious in a mouse model of MS. The effectiveness of GM6 was dose dependent which indicates that GM6 can be beneficial in the treatment of MS.

Example 8

Testing of GM602 (MNTF6mer) in the Mouse Model of Middle Cerebral Artery Occlusion Genervon Biopharmaceuticals, LLC test article GM602 was tested for efficacy in the middle cerebral artery occlusion (MCAO) mouse model. In order to determine the efficacy of GM602 in the MCAO mouse model, mice were subjected to 1 hour of ischemia and 14 days of reperfusion. Mice were injected intravenously bolus via tail vein with GM602 at 0, 3, 6, 12 and 24 hours after the start of reperfusion and examined for changes in cerebral blood flow (CBF), heart rate (HR), blood pressure (BP), $pO_2$, $pCO_2$, pH, neurological deficits (ND) and infarct volume (IFV). Intravenous (i.v.) administration of GM602 (5 mg/kg) at the indicated times following ischemia and every day for 3 days was examined for neuroprotection. Administration of GM602, demonstrated no changes in CBF, HR, BP, $pO_2$% $pCO_2$, or pH. Changes were detected in ND and IFV, which was time dependent. GM602 at 5 mg/kg showed a significant protection from infarct damage at 0, 3, 6 and 12 hours, which translated to preservation of neurological deficits. These data suggest that GM602 is neuroprotective to the brain following i.v. injection in the mouse model of MCAO.

Abbreviations/Terminology

| Abbreviations/Terminology | Definition |
|---|---|
| MNTF | Motoneuronotrophic factor |
| MNTF6mer | 6-amino acid peptide analog of MNTF |
| GM602 | 6-amino acid peptide analog of MNTF for Stroke |
| MCAO | Middle Cerebral Artery Occlusion |
| GB | Genervon Biopharmaceuticals LLC |
| I.V. | Intravenous |
| CBF | cerebral blood flow |
| HR | Heart Rate |
| BP | Blood pressure |
| ND | Neurological deficits |
| IFV | Infarct volume |

Test of the ability of GB test article GM602, a 6-amino acid peptide analog of Motoneurontrophic factor (MNTF6mer; FSRYAR) to protect the brain from acute ischemia and reperfusion injury. GM602 is chemically synthesized under GMP compliance (CS Bio Co., Menlo Park, Calif., GMP013, lot C811). The GM602 was provided as a solid and formulation prepared accordingly (solution stored at 4° C.).

Methods and Materials

Animals

C57BL/6 mice (Jackson Laboratory, Bar Harbor, Me.), weighing 22-25 grams each were given free access to food and water before the experiment. The animals were anesthetized with halothane (1% in 70%/30% $NO_2/O_2$ by mask). Monitoring of mean arterial blood pressure (MABP) via tail cuff apparatus, and blood samples were collected to determine arterial pH levels and $PaCO_2$ and $PaO_2$. The MABP and heart rate was recorded using a Visitech System blood pressure monitor.

Brain temperature was monitored using a rectal thermometer and thermistor probe inserted into the temporalis muscle. The animals' body temperature was maintained at 37° C. by using a water-jacketed heating pad. Brain temperature was monitored for 1 hour prior to ischemia to 6 hours following ischemia and was recorded at 30-minute intervals.

Experimental Groups

Animals were subjected to 1.0 h ischemia and 24 h reperfusion and was divided into a vehicle group (n=10) or groups (n=10) treated with an intravenous injection of GM602 at a dose of 5 mg/kg. Formulation of GM602 (CS Bio Co., Menlo Park, Calif., CS1507, GMP013, lot C811) was performed by NTS as a stock solution by reconstituting GM602 with (100%) saline that was stored at 4° C. Vehicle control received saline solution. The bolus IV injections via tail with GM602 was initiated at times of 0, 3, 6, 12 and 24 hours after the start of reperfusion and subsequently every day for 3 days following injury. The investigators were blinded to the treatment groups.

Induction of Ischemia

This study involved a transient model of ischemia. Each mouse was anesthetized and the external carotid artery (ECA) and common carotid artery (CCA) was isolated. Thermistor probes were inserted into the rectum and temporalis muscle to monitor body and brain temperature, which was maintained at 36-37° C. by external warming. The left common carotid artery (CCA) was exposed through a midline incision in the neck. The superior thyroid and occipital arteries were electrocoagulated and divided. A microsurgical clip was placed around the origin of the external carotid artery (ECA). The distal end of the ECA was ligated with 6-0 silk and transected. A 6-0 silk was tied loosely around the ECA stump. The clip was removed and the fire-polished tip of a 5-0 nylon suture (silicone coated) was gently inserted into the ECA stump. The loop of the 6-0 silk was tightened around the stump and the nylon suture was advanced approximately 13 mm (adjusted for body weight) into and through the internal carotid artery (ICA) until it rests in the anterior cerebral artery (ACA), thereby occluding the anterior communicating and middle cerebral arteries. After the nylon suture was in place for 1 hour, it was pulled back into the ECA and the incision closed.

Histological Examination

For histological examination, the animals were anesthetized with an intraperitoneal injection of sodium pentobarbital (50 mg/kg) 14 days after ischemia was induced. The brains were transcardially perfused with 4° C., 10% phosphate-buffered saline (PBS). The brains were removed and chilled for 15 minutes at −20° C. before being placed in a Rodent Brain Matrix. Coronal sections (1-mm thickness) were prepared and subjected to 2% triphenyltetrazolium chloride (TTC) staining at 37° C. Seven serial one-mm thick coronal sections through the rostral to caudal extent of the infarction were obtained from each brain, beginning two-mm from the frontal pole. The TTC stained sections were placed in 10% neutral buffered formalin and kept in darkness at 4° C. for at least 24 hours. The infarct area in each section was determined with a computer-assisted image analysis system, consisting of a Power Macintosh computer equipped with a Quick Capture frame grabber card, Hitachi CCD camera mounted on an Olympus microscope and camera stand. NIH Image Analysis Software, v. 1.55 was used. The images were captured and the total area of damage determined over the seven sections. A single operator blinded to treatment status performed all measurements. The infarct volume was calculated by summing the infarct volumes of the sections. Infarct size (%) was calculated by using the following formula: (contralateral volume−ipsilateral undamaged volume)×100/contralateral volume to eliminate effects of oedema.

Measurement of Cerebral Blood Flow

Cerebral blood flow (CBF) was monitored by using a laser Doppler flowmeter. The CBF values were determined as a percentage, because the values displayed by the laser Doppler flowmeter were not absolute. As described above, the animals were anesthetized with halothane (1% in 70%/30% $NO_2/O_2$ by mask). In the hemisphere ipsilateral to the MCA occlusion, coordinates were as follows: point a, 0.5 mm posterior to the bregma and 2 mm lateral to the midline; point B, 1 mm posterior to the bregma and 1.2 mm lateral to the midline; point D, 1 mm anterior to the bregma and 1.7 mm lateral to the midline; and point C in the contralateral hemisphere, 1 mm posterior to the bregma and 2 mm from the midline. CBF was measured prior to the onset of ischemia and continue for two hours after the end of infusion. Measurements were taken before injection of compounds and post injection (continuous measurements were taken from 15 minutes prior to ischemia to 30 minutes after the end of injection of the compound and recorded every 30 minutes). The mean values after MCA occlusion and before administration were taken as baseline and the data thereafter were expressed as percentages of the baseline value.

Behavioral Assessment

Behavioral analysis (neurological deficit) was determined in the mice before and after ischemic injury. Neurological scores were as follows: 0, normal motor function; 1, flexion of torso and contralateral forelimb when animal was lifted by the tail; 2, circling to the contralateral side when held by tail on flat surface, but normal posture at rest; 3, leaning to the contralateral side at rest; 4, no spontaneous motor activity.

Exclusion of Animals from the Study

Animals were excluded from the study based upon several criteria:

Animals die prior to completion of study (at any point). Data collected to the time of death was provided to GB.

Cerebral blood flow did not decrease to 20±5% of baseline value (i.e., considered non-ischemic) or blood flow does not return to 90±10% of baseline value.

Animals developed seizure-like activity following ischemic injury.

Excessive bleeding was detected during or immediately following ischemia.

Statistical Analysis

The results were expressed as the mean±standard deviation (SD). The significance of difference in the physiological and histological data was analyzed using a one-way analysis of variance (ANOVA) followed by Fisher's post hoc test. Repeated-measures ANOVA were computed on the monitoring data and the significance of the difference among groups were evaluated by Fisher's post hoc test.

Treatment groups. All groups were subjected to GM602 or were controls. Animals (30 animals) were subjected to i.v. dosing of vehicle or GM602 at the indicated doses.

Mouse Stroke Model:

| Group | Compound | Dose (mg/kg) | Route |
|---|---|---|---|
| 1 (n = 10 mice) | Vehicle | 0 | IV |
| 2 (n = 10 mice) | MNTF | 5 mg/kg 0 min after ischemia | IV |
| 3 (n = 10 mice) | MNTF | 5 mg/kg 3 hr after ischemia | IV |
| 4 (n = 10 mice) | MNTF | 5 mg/kg 6 hr after ischemia | IV |
| 5 (n = 10 mice) | MNTF | 5 mg/kg 12 hr after ischemia | IV |
| 6 (n = 10 mice) | MNTF | 5 mg/kg 24 hr after ischemia | IV |

Endpoints

Effects of MNTF of neuroprotection from ischemia and reperfusion injury. Animals will be evaluated for cerebral blood flow (CBF), heart rate (HR), blood pressure (BP), $pO_2$, $pCO_2$, pH, neurological deficits (ND) and infarct volume (IFV).

All test groups have been provided to NTS; GM602 was provided as a solid material to NTS. All animals in the test groups were dosed as indicated above.

Results

Ischemia in mice study. The relative severity of ischemia in these studies was assessed. Data were from mice with ischemic injury that were intravenously injected with vehicle or GM602.

Figure 26:
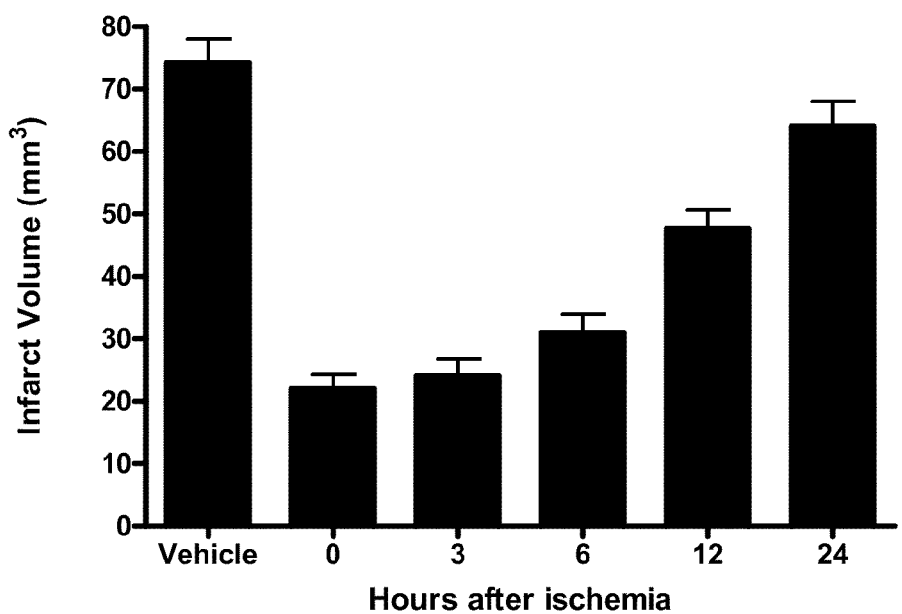
FIG. 26. Illustrates data from the study of the effects of GM602 on infarct volumes in the mouse following transient ischemia. All mice were subjected to 1 hour of cerebral ischemia followed by 14 days of reperfusion. Animals were injected with vehicle (control), GM602 at 5 mg/kg intravenously at the times indicated (3, 6, 12, 24 hrs) after the ischemia. In addition, animals were injected daily for 3 days following injury. Animals were sacrificed on day 14 and processed to determine the infarct volume.
Figure 27:
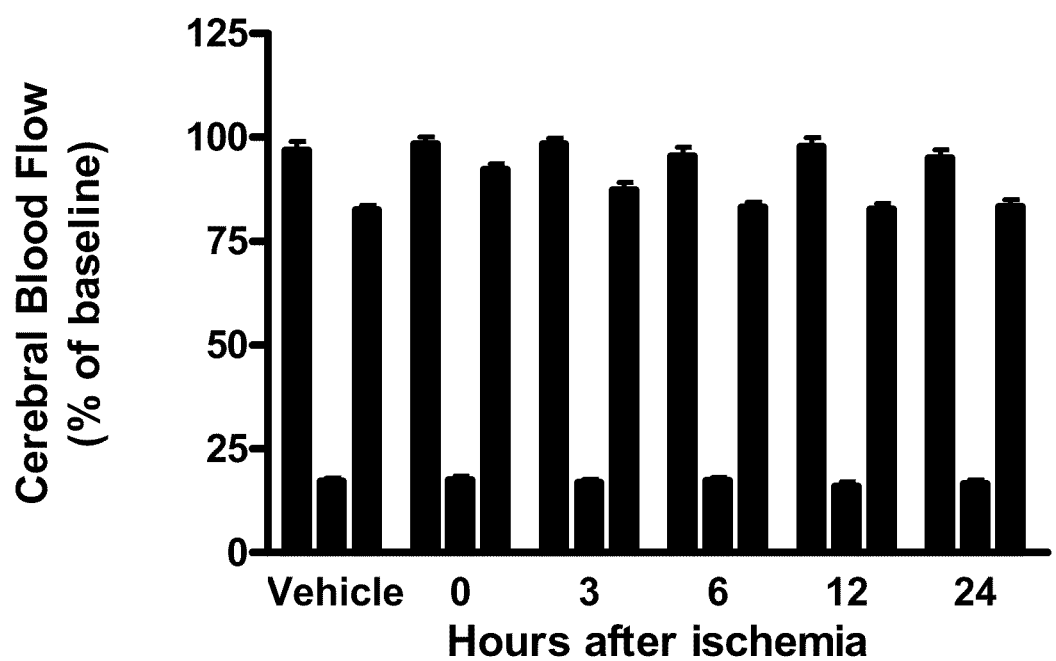
FIG. 27. Illustrates data from the study of cerebral blood flow from animals subject to ischemia/reperfusion injury. All mice were subjected to 1 hour of cerebral ischemia followed by 14 days of reperfusion. Test articles were administered at 3, 6, 12, and 24 hours after ischemia onset. Blood flow was measured before ischemia, after ischemia and after reperfusion.
Figure 28:
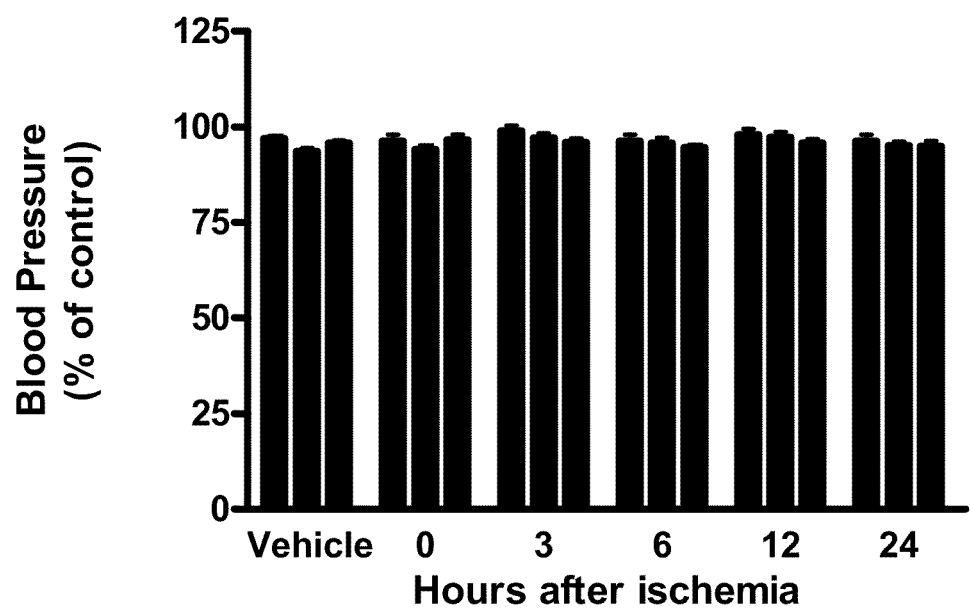
FIG. 28. Blood pressure measurement in mice subject to ischemia/reperfusion injury. All mice were subjected to 1 hour of cerebral ischemia followed by 14 days of reperfusion. Test articles were administered at 3, 6, 12, and 24 hours after ischemia onset. Blood pressure was measure prior to, during and after the end of ischemia.
Figure 29:
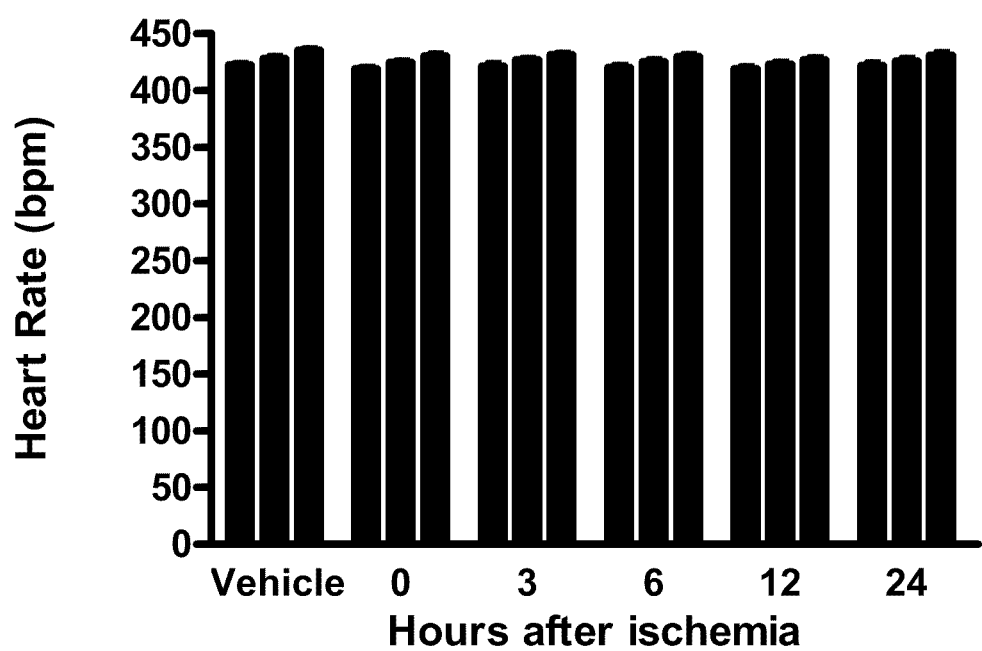
FIG. 29. Heart rate measurement in mice subject to ischemia/reperfusion injury. All mice were subjected to 1 hour of cerebral ischemia followed by 14 days of reperfusion. Test articles were administered at 3, 6, 12, and 24 hours after ischemia onset. Heart rate was measured prior to, during and after the end of ischemia.
Figure 30A:
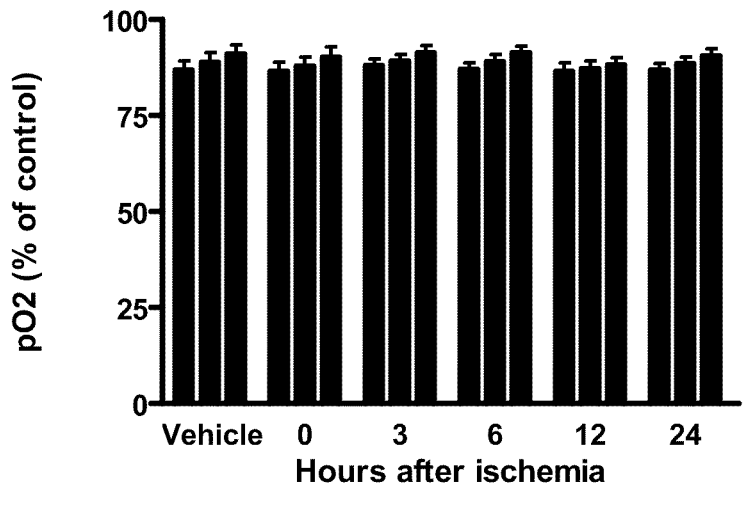
FIGS. 30A and 30B. Blood gas measurement in mice subject to ischemia/reperfusion injury. All mice were subjected to 1 hour of cerebral ischemia followed by 14 days of reperfusion. Test articles were administered at 3, 6, 12, and 24 hours after ischemia onset. Blood gases $pO_2$ (30A) and $pCO_2$ (30B) were measured prior to, during and after the end of ischemia.
Figure 30B:
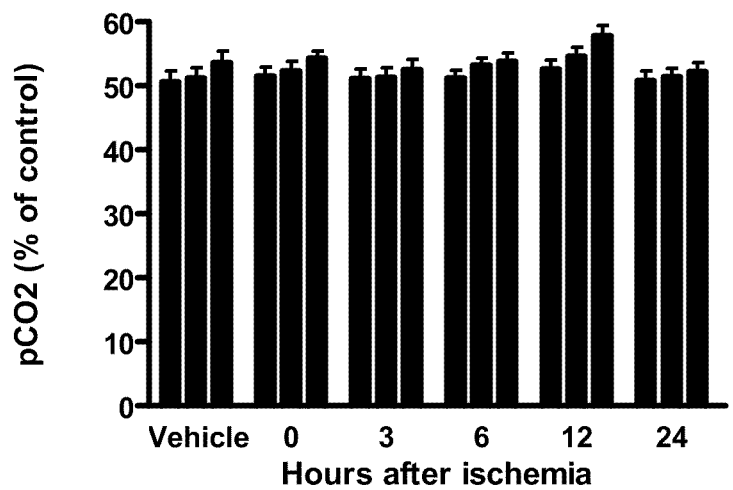
Figure 31:
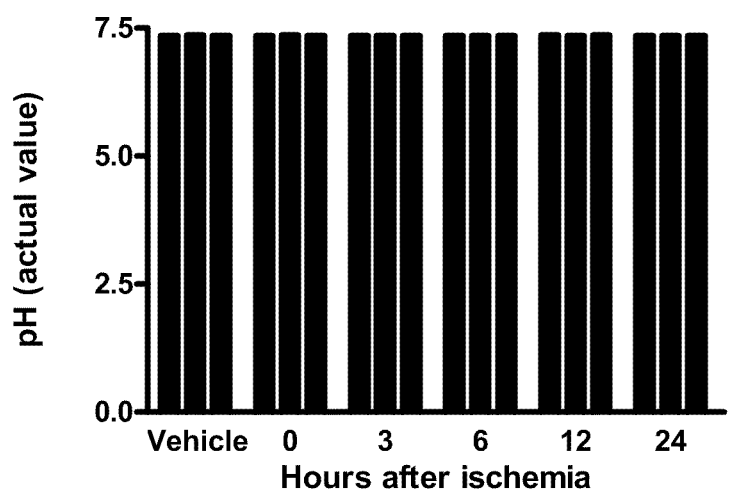
FIG. 31. pH measurement in mice subject to ischemia/reperfusion injury. All mice were subjected to 1 hour of cerebral ischemia followed by 14 days of reperfusion. Test articles were administered at 3, 6, 12, and 24 hours after ischemia onset. pH was measured prior to, during and after the end of ischemia.

Infarct Volume: Compared with the vehicle-injected group, the infarct volume in the brains was significantly decreased with the GM602 groups (0, 3, 6, and 12 hours). GM602 showed a time dependent reduction in infarct volume from 0 to 12 hours following ischemia (Table 1). Infarct volumes are plotted in FIG. 26. The percent decrease in infarct volume present in the brains is presented in Table 23. As shown in the table, GM602 at 0, 3, 6 and 12 hours showed a 70, 68, 58 and 36% reduction in infarct size. The infarct volume at 24 hours, although decreased did not show a significant difference from the vehicle treated animals.

TABLE 23

Percent decrease in infarct in the brain.

| Group | Dose Mg/kg | Infarct Volume ($mm^3$) | Percent reduction in Infarct volume* | P-value* |
|---|---|---|---|---|
| 1 | 0 | 74.26 ± 12.09 | 0 | NA |
| 2 | 5 | 22.05 ± 7.292 | 70.3% | 0.001 |
| 3 | 5 | 24.15 ± 8.110 | 67.5% | 0.001 |
| 4 | 5 | 31.03 ± 9.255 | 58.2% | 0.001 |
| 5 | 5 | 47.72 ± 9.118 | 35.7% | 0.001 |
| 6 | 5 | 64.13 ± 12.51 | 13.4% | 0.0821 |

Percent decreases are compared to the respective vehicle control animals.
*Compared to Group 1 (Vehicle)

Mortality: There were no deaths in this study.

Physiological parameters. There were no significant differences in physiological parameters (cerebral blood flow, mean arterial pressure, blood $pO_2$, $pCO_2$, and pH) between the vehicle and treated mice at baseline, during ischemia, or after reperfusion (FIGS. 27-31).

Figure 32:
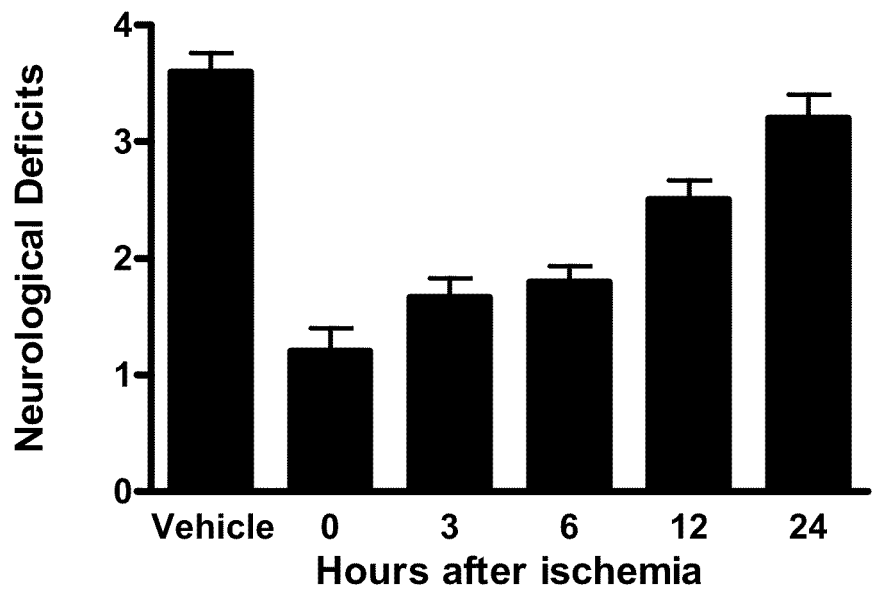
FIG. 32. Neurological deficit measurements in mice subject to ischemia/reperfusion injury. All mice were subjected to 1 hour of cerebral ischemia followed by 14 days of reperfusion. Test articles were administered at 3, 6, 12, and 24 hours after ischemia onset. Neurological deficits were measured at the end of reperfusion.

Behavioral Measurements. Animals were assessed for neurological deficits based on a scale of 0 to 4. Animals treated with GM602 showed a time dependent decrease in neurological deficits (data also shown in FIG. 32).

TABLE 24

| Compound (Group) | Neurological Deficits | P value compare to vehicle |
|---|---|---|
| 1 - Vehicle | 3.600 ± 0.163 | NA |
| 2 - GM602 | 1.200 ± 0.200 | p = 0.001 |
| 3 - GM602 | 1.667 ± 0.167 | p = 0.001 |
| 4 - GM602 | 1.800 ± 0.133 | p = 0.001 |
| 5 - GM602 | 2.500 ± 0.167 | p = 0.002 |
| 6 - GM602 | 3.200 ± 0.200 | p = 0.1387 |

Stroke is the third most common cause of death and the main cause of disability in the United States. The outcome and infarction size after focal cerebral ischemia is determined by both "necrotic" (paraptosis) cell death and by delayed neuronal cell loss in the borderzone of ischemia (programmed cell death or apoptosis). Recent therapies have emerged to treat ischemic stroke, however, these treatments mostly dealt with dissolving the blood clot but did not address neuroprotection or reduction of behavioral deficit or brain infarct volume once the neuronal cell death cycle has been triggered. Understanding the basic mechanisms that influence cell loss will help in the design of drugs and applications to reduce cell death associated with ischemic injury.

MNTF is a trophic factor that may provide protection from neurological diseases and allow for regeneration of neuronal tissue following injury or ischemic stroke. The studies performed here demonstrate the ability of GM602, the 6-amino acid analog of MNTF to protect the brain from the detrimental effects of cerebral ischemia and reperfusion injury in an effective and efficient way. Intravenous administration of GM602 at 5 mg/kg at various times following ischemic injury demonstrated a time dependent protective effect in the brain against ischemia/reperfusion injury by a decrease in infarct volume and behavioral attributes. These studies suggest that GM602 may have a beneficial effect in stroke.

When administered intravenously, GM602 was found to be neuroprotective against ischemia/reperfusion injury in the mouse.

Example 9

Testing of GM602 (MNTF6mer) in the Rat Model of Permanent Middle Cerebral Artery Occlusion Genervon Biopharmaceuticals, LLC test article GM602 was tested for efficacy in the permanent middle cerebral artery occlusion (MCAO) rat model (Kindy, Study #2C Stroke). In order to determine the efficacy of GM602 in the permanent MCAO rat model, rats were subjected to permanent ischemia followed for 28 days. Rats were injected intravenously bolus via tail vein with GM602 at 3 hours after the start of ischemia. Rats were examined for changes in cerebral blood flow (CBF), heart rate (HR), blood pressure (BP), $pO_2$, $pCO_2$, pH, neurological deficits (ND) and infarct volume (IFV). While administration of GM602 demonstrated no changes in HR, BP, $pO_2$, $pCO_2$, or pH, GM602-demonstrated an increase in CBF when administered at 3 hours after ischemia. More importantly, significant decrease in ND, IFV, TNF (inflammation biomarker) and Fluoro-Jade (neuron degeneration biomarker) were observed, in a dose dependent fashion following GM602 administration. IV injection of GM602 at 2.5, 10 or 20 mg/kg showed a significant protection from infarct damage when administered, which translated to preservation of neurological deficits. These data suggest that IV injection of GM602 during ischemia is neuroprotective to the brain in the permanent rat model of MCAO. The treatment with GM602 at 3 hours after the onset of ischemia demonstrated a protective effect and may be feasible for clinical trials.

| Abbreviations/Terminology | Definition |
|---|---|
| MNTF | Motoneuronotrophic factor |
| MNTF6mer | 6-amino acid peptide analog of MNTF |
| GM602 | 6-amino acid peptide analog FSRYAR of MNTF for Stroke |
| MCAO | Middle Cerebral Artery Occulsion |
| GB | Genervon Biopharmaceuticals LLC |
| I.V. | Intravenous |
| CBF | Cerebral blood flow |
| HR | Heart Rate |
| BP | Blood pressure |
| ND | Neurological deficits |
| IFV | Infarct volume |
| NS | No statistical significant |

With these data in hand, the decision was made to test the ability of GB test article GM602, a 6-amino acid peptide analog of Motoneurontrophic factor (MNTF6mer), to protect the brain from chronic ischemic injury in the permanent middle cerebral artery occlusion (MCAO) rat model. GM602 is chemically synthesized under GMP compliance (CS Bio Co., Menlo Park, Calif., lot D294).

Methods and Materials

Animals

Sprague-Dawley rats (Harlan), weighing 225-250 grams each were given free access to food and water before the experiment. The animals were anesthetized with halothane (1% in 70%/30% NO2/O2 by mask). Blood samples were collected to determine arterial pH levels and PaCO2 and PaO2. The MABP and heart rate were recorded using a Visitech System.

Brain temperature was monitored using a rectal thermometer and thermistor probe inserted into the temporalis muscle. The animals' body temperature was maintained at 37° C. by using a water-jacketed heating pad. Brain temperature was monitored for 1 hour prior to ischemia to 6 hours following ischemia and will be recorded at 30-minute intervals.

Experimental Groups

All rats were subjected to permanent ischemia. Animals were randomly assigned into a vehicle group (n=10) or one of the three groups (n=10) treated with an intravenous injection of GM602 at a dose of 2.5, 10 or 20 mg/kg. The bolus IV injections via tail vein were given at 3 hours after the onset of ischemia. The investigators were blinded to the treatment groups. Formulation of GM6 was performed by NTS and reconstituted GM6 as a stock solution with normal saline solution that was stored at 4° C. Vehicle controls received saline solution.

Induction of Ischemia

This study involved a permanent model of ischemia. Each rat was anesthetized, the external carotid artery (ECA) and common carotid artery (CCA) were isolated. Thermistor probes were inserted into the rectum and temporalis muscle to monitor body and brain temperature, the rat was maintained at 36-37° C. by external warming. The left common carotid artery (CCA) was exposed through a midline incision in the neck. The superior thyroid and occipital arteries were electrocoagulated and divided. A microsurgical clip was placed around the origin of the external carotid artery (ECA). The distal end of the ECA was ligated with 6-0 silk and transected. A 6-0 silk was tied loosely around the ECA stump. The clip was removed and the fire-polished tip of a 5-0 nylon suture (silicone coated) was gently inserted into the ECA stump. The loop of the 6-0 silk was tightened around the stump and the nylon suture was advanced approximately 17 mm (adjusted for body weight) into and through the internal carotid artery (ICA) until it rests in the anterior cerebral artery (ACA), thereby occluding the anterior communicating and middle cerebral arteries. The wound was closed immediately after insertion of the nylon suture using surgical staples. The sutures remained in placed for 28 days.

Histological Examination

For histological examination, the animals were anesthetized with an intraperitoneal injection of sodium pentobarbital (50 mg/kg) 28 days after ischemia was induced. The brains were transcardially perfused with 4° C., 10% phosphate-buffered saline (PBS) followed by 4% paraformaldehyde (4° C.). The brains were removed and fixed overnight in 4% paraformaldehyde followed by 30% sucrose for 24 hours at 4° C. The tissue was embedded in OCT medium and frozen on dry ice (stored at −80° C.). These were used for histological and immunocytochemical analysis. Brains were collected 28 d after the onset of ischemia, frozen, and sectioned into 16-µm sections. Coronal sections were stained with hematoxylin and eosin to clearly delineate the extent of ischemic injury. The volume of infarct was calculated by integrating the area of injury on 16-µm stained coronal sections collected from the bregma points +2.46, +1.66, +0.86, +0.06, 0.74, 1.54, 2.34, and 3.14 mm of each brain. Total, cortical, striatal, and hippocampal infarct volumes was quantified with a computer-assisted imaging system (NIH IMAGE, Version 1.6). A single operator blinded to treatment status performed all measurements. The infarct volume was calculated by summing the infarct volumes of the sections. Infarct size (%) was calculated by using the following formula: (contralateral volume−ipsilateral undamaged volume)×100/contralateral volume to eliminate effects of oedema.

Measurement of Cerebral Blood Flow

Cerebral blood flow (CBF) was monitored by using a laser Doppler flowmeter. The CBF values were determined as a percentage, because the values displayed by the laser Doppler flowmeter are not absolute. As described above, the animals were anesthetized with halothane (1% in 70%/30% NO2/O2 by mask). In the hemisphere ipsilateral to the MCA occlusion, coordinates were as follows: point A, 0.5 mm posterior to the bregma and 2 mm lateral to the midline; point B, 1 mm posterior to the bregma and 1.2 mm lateral to the midline; point D, 1 mm anterior to the bregma and 1.7 mm lateral to the midline; and point C in the contralateral hemisphere, 1 mm posterior to the bregma and 2 mm from the midline. CBF was measured prior to the onset of ischemia, three hours after induction of ischemia but prior to administration of test articles, and 1 hour after administration of test articles. The mean values before MCA occlusion were taken as baseline and the data thereafter was expressed as percentages of the baseline value.

Behavioral Assessment

Animals were handled for 10 min each day for 3 days before ischemic injury. The day prior to injury, animals were examined for behavioral changes.

All behavioral tests were administered just before stroke surgery and then 28 days after administration of test articles. At each session, animals were allowed to adapt to the testing room for 30 min before testing began.

Forelimb placing test—Separate scores were obtained for each forelimb. For the visual placing subtest, the animal was held upright by the examiner and brought close to a table top. Normal placing of the limb on the table were scored as 0, delayed placing (<2 s) were scored as 1, and no or very delayed placing (>2 s) were scored as 2. Separate scores were obtained first as the animal was brought forward and then again the animal was brought sideways to the table (maximum score per limb, 4; in each case, higher numbers denoted greater deficits). For the tactile placing subtest, the animal was held so that it cannot see or touch the tabletop with its whiskers. The dorsal forepaw was touched lightly to the tabletop as the animal was first brought forward and then brought sideways to the table. Placing each time was scored as above (maximum score per limb, 4). For the proprioceptive placing subtest, the animal was brought forward only, and greater pressure was applied to the dorsal forepaw; placing was scored as above (maximum score per limb, 2). These subscores were added to give the total forelimb placing score per limb (range, 0-10).

Hindlimb placing test—The hindlimb placing test will be conducted in the same manner as above for the hindlimbs, but will involve only tactile and proprioceptive subtests (maximal scores 4 and 2, respectively; total score range, 0-6).

Modified balance beam test—The modified beam balance test examined vestibulomotor reflex activity as the animal balances on a narrow beam (30×1.3 cm) for 60 s. Ability to balance on the beam was scored as follows: animal balances with all four paws on the top of beam, 1; animal puts paws on side of beam or wavers on beam, 2; one or two limbs slipped off beam, 3; three limbs slipped off beam, 4; animal attempts to balance with paws on beam but fell off, 5; animal drapes over beam, then fell off, 6; animal fell off beam without an attempt to balance, 7. Animals received three training trials before surgery; the score of the last of these was taken as the baseline score.

Spontaneous motor activity—Animals were placed in a narrow glass cylinder (16.5×25 cm) and videotaped for 10 min on the day before surgery and at one week after. Animals were scored for spontaneous movements. Scoring was as follows: 0, no movement; 1, little or no exploration (limited movement); 2, some exploration (some restricted movement); 3, unrestricted movement (control, normal exploration).

Biomarker Analysis

Coronal sections 16 µm in thickness were mounted then dried on microscope slides. The slides were immersed in a solution containing 1% sodium hydroxide in 80% alcohol (20 mL of 5% NaOH added to 80 mL absolute alcohol) for 5 minutes. Then followed by 2 minutes in 70% alcohol and 2 minutes in distilled water. The slides were transferred to a solution of 0.06% potassium permanganate for 10 minutes. The slides were rinsed in distilled water for 2 minutes. The staining solution was prepared from a 0.01% stock solution for Fluoro-Jade® B. After 20 minutes in the staining solution, the slides were rinsed for one minute in each of three distilled water washes. Excess water was removed by briefly (about 15 s) draining the slides vertically on a paper towel. The slides were then placed on a slide warmer, set at approximately 50° C., until they were fully dry, (eg. 5-10 min). The dry slides were cleared by immersion in xylene for at least a minute before coverslipping with DPX (Fluka, Milwaukee Wis., or Sigma Chem. Co., St. Louis, Mo.), a non-aqueous non-fluorescent plastic mounting media. For cytokine analysis (TNF) tissue sections were washed in Tris buffered saline (TBS) pH 7.4 and blocked in the appropriate serum (goat). Sections were blocked overnight at 4° C. and then subjected to primary antibody overnight at 4° C. Sections were washed in TBS and secondary antibody was added and incubated for 1 hour at room temperature. After washing, the sections were incubated as instructed in the Vector ABC Elite kit and stained with diaminobenzoic acid (DAB). The reactions were stopped in water and cover slipped after treatment to xylene.

Exclusion of Animals from the Study

Animals were excluded from the study based upon several criteria:

Animals die prior to completion of study (at any point). Data collected to the time of death was provided to GB.

Cerebral blood flow did not decrease to 20±5% of baseline value after occlusion (i.e., considered non-ischemic).

Animals developed seizure-like activity following ischemic injury.

Excessive bleeding was detected during or immediately following ischemia.

Treatment groups. All groups were subjected to GM602 or were controls. Animals received IV dosing of vehicle or GM602 at 3 hours following the induction of ischemia.

Rat Stroke Model:

| Group | Compound | Dose (mg/kg) | Route |
|---|---|---|---|
| 1 (n = 10 rats) | Vehicle | 0 | IV |
| 2 (n = 10 rats) | GM602 | 2.5 mg/kg | IV |
| 3 (n = 10 rats) | GM602 | 10 mg/kg | IV |
| 4 (n = 10 rats) | GM602 | 20 mg/kg | IV |

Endpoints

Effects of GM602 on neuroprotection from ischemia and reperfusion injury. Animals will be evaluated for cerebral blood flow (CBF), heart rate (HR), blood pressure (BP), $pO_2$, $pCO_2$, pH, neurological deficits (ND), infarct volume (IFV), inflammation biomarker and neuron degeneration biomarkers.

All test groups have been provided to NTS; GM602 was provided as a solid material to NTS. All animals in the test groups were dosed as indicated above.

Statistical Analysis

The results were expressed as the mean±standard deviation (SD). The significance of difference in the physiological and histological data was analyzed using a one-way analysis of variance (ANOVA) followed by Fisher's post hoc test. Repeated-measures ANOVA were computed on the monitoring data and the significance of the difference among groups were evaluated by Fisher's post hoc test.

Results

Ischemia study in rats. The relative severity of ischemia in these studies was assessed. Data were from rats with ischemic injury that were intravenously injected with vehicle or GM602.

Figure 33:
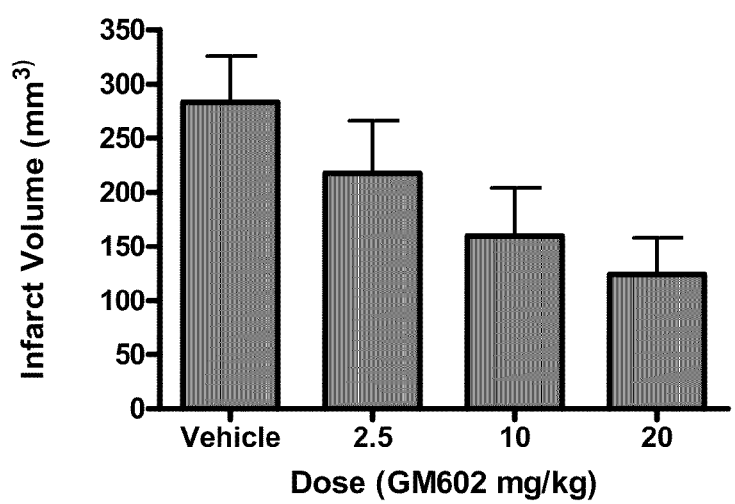
FIG. 33. Effects of GM602 on infarct volumes in the rat following ischemia. All rats were subjected to permanent cerebral ischemia for 28 days. Animals were injected with vehicle (control) or GM602 at 0, 2.5, 10 or 20 mg/kg intravenously at 3 hours following the initiation of ischemia. Animals were sacrificed on day 28 and processed to determine the infarct volume.

Infarct Volume: Infarct volumes for all study groups are plotted in FIG. 33. 3 hours post permanent ischemia IV administration of GM602 reduced the infarct volume in the animal brains. The percent decrease in infarct volume is presented in Table 25.

TABLE 25

Percent decrease in infarct in the brain.

| Group | Dose mg/kg | Infarct Volume (mm³) | % Reduction in Infarct Volume* | P-value* |
|---|---|---|---|---|
| 1 | 0 | 283.7 ± 42.66 | 0 | NA |
| 2 | 2.5 | 217.5 ± 48.44 | 23.3% | p < 0.0045 |
| 3 | 10 | 159.6 ± 44.84 | 43.6% | p < 0.0001 |
| 4 | 20 | 124.3 ± 33.82 | 56.2% | p < 0.0001 |

Percent decreases are compared to the vehicle control animals.
*Compared to Group 1 (Vehicle)

Mortality: There were no deaths in this study.

Figure 34:
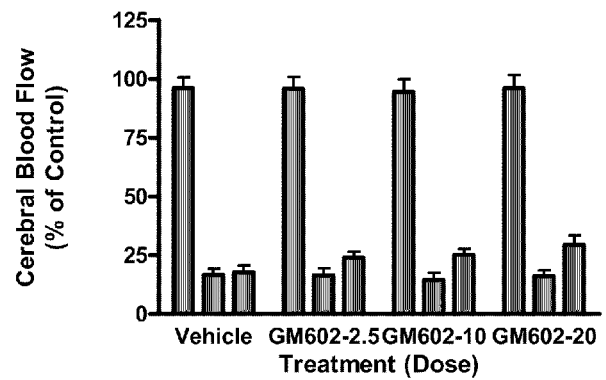
FIG. 34. Cerebral blood flow from animals subject to ischemia. All rats were subjected to cerebral ischemia followed by 28 days of recovery. At 3 hours after ischemia onset, animals were injected with vehicle (control) or GM602 at 2.5, 10 or 20 mg/kg intravenously. For each study group, blood flow was measured before ischemia (first column, CBF at pre-ischemia baseline), during ischemia (second column, CBF 3 hours after permanent ischemia but prior to administration of test articles) and after injection of test articles (third column, CBF 1 hours after test article administration).
Figure 35:
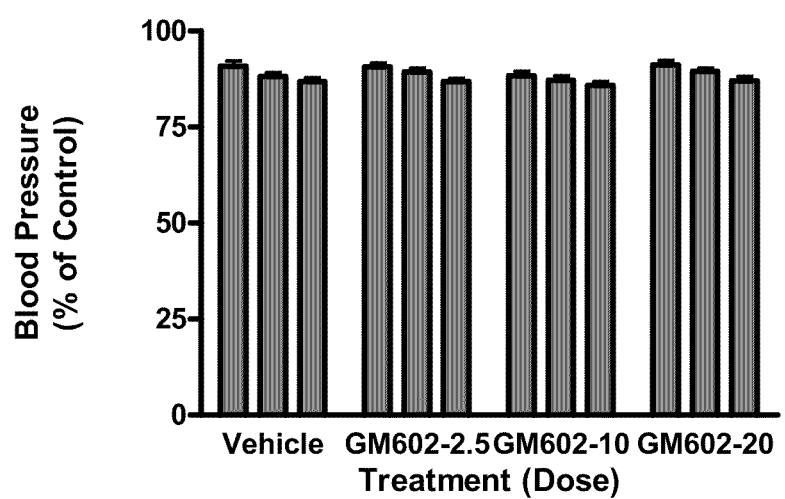
FIG. 35. Blood pressure measurement in rats subject to ischemia. All rats were subjected to permanent cerebral ischemia followed by 28 days of recovery. At 3 hours after ischemia onset, animals were injected with vehicle (control) or GM602 at 2.5, 10 or 20 mg/kg intravenously. For each study group, blood pressure was measured before ischemia (first column), during ischemia (second column) and after injection of test articles (third column).
Figure 36:
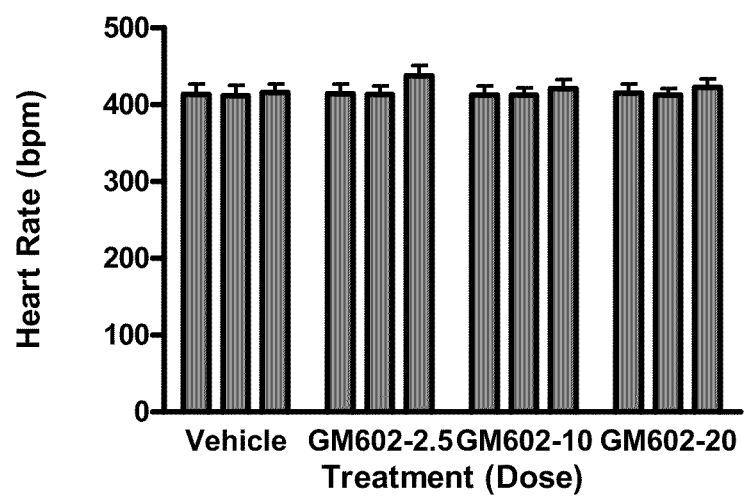
FIG. 36. Heart rate measurement in rats subject to ischemia. All rats were subjected to permanent cerebral ischemia followed by 28 days of recovery. At 3 hours after ischemia onset, animals were injected with vehicle (control) or GM602 at 2.5, 10 or 20 mg/kg intravenously. For each study group, heart rate was measured before ischemia (first column), during ischemia (second column) and after injection of test articles (third column).
Figures 37A, 37B:
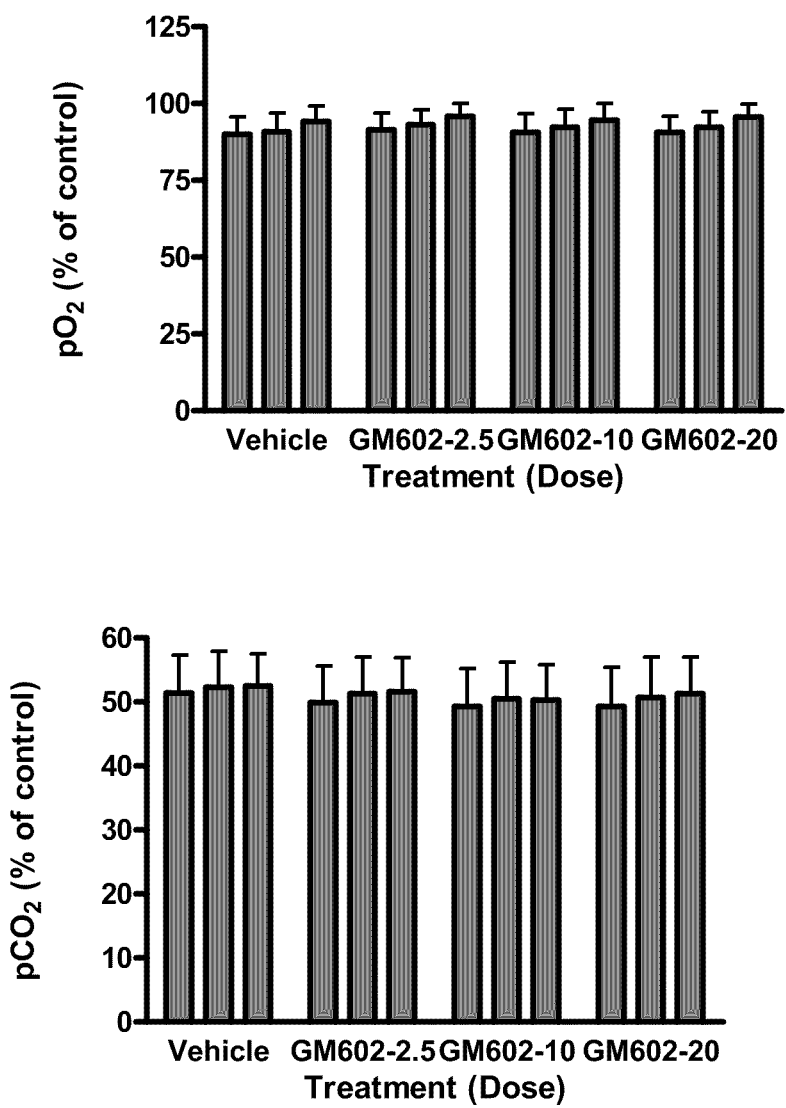
FIGS. 37A and 37B. Blood gas measurement in rats subject to ischemia. All rats were subjected to permanent cerebral ischemia followed by 28 days of recovery. At 3 hours after ischemia onset, animals were injected with vehicle (control) or GM602 at 2.5, 10 or 20 mg/kg intravenously. For each study group, blood gases $pO_2$ (FIG. 37A) and $pCO_2$ (FIG. 37B) were measured before ischemia (first column), during ischemia (second column) and after injection of test articles (third column).
Figure 38:
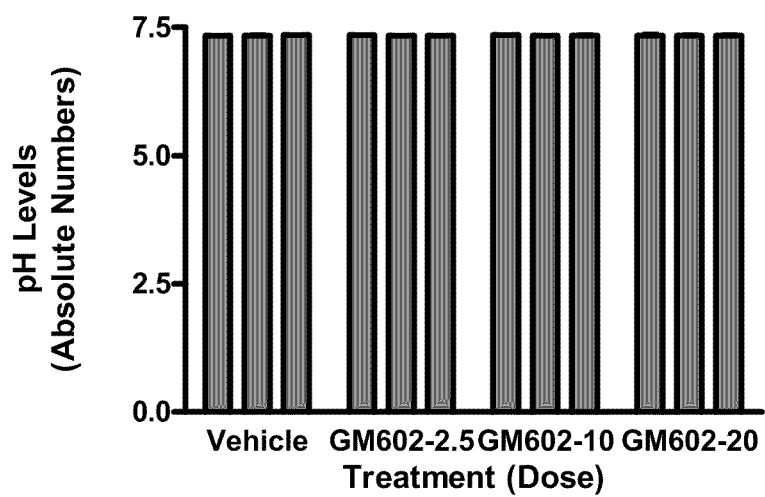
FIG. 38. pH measurement in rats subject to ischemia. All rats were subjected to permanent cerebral ischemia followed by 28 days of recovery. At 3 hours after ischemia onset, animals were injected with vehicle (control) or GM602 at 2.5, 10 or 20 mg/kg intravenously. For each study group, pH was measured before ischemia (first column), during ischemia (second column) and after injection of test articles (third column).
Figure 40:
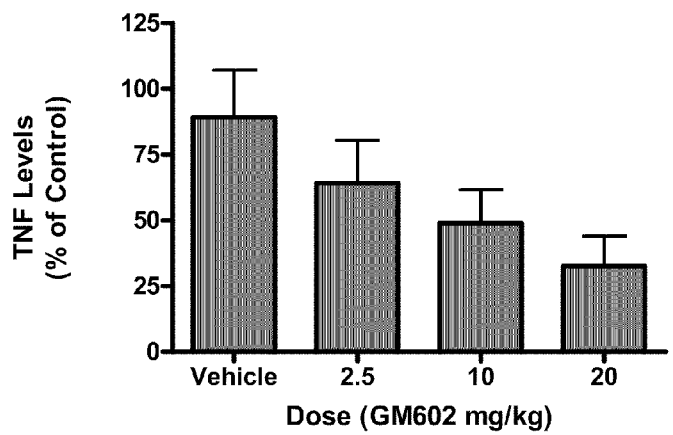
FIG. 40. Biomarker measurements in rats subject to ischemic injury. All rats were subjected to permanent cerebral ischemia followed by 28 days of recovery. At 3 hours after ischemia onset, animals were injected with vehicle (control), GM602 at 2.5, 10 or 20 mg/kg intravenously. Animals were sacrificed on day 28 and brain sections were processed for TNF immunohistochemical analysis.

Physiological parameters. There were no significant differences in physiological parameters (mean arterial pressure, blood pO2, pCO2, and pH) between the vehicle and treated mice at baseline, during ischemia, or after test drug administration (FIGS. 35-38). However, GM602-mediated significant increase in cerebral blood flow was observed in the groups treated with GM602 (FIG. 34).

TABLE 26

Increase in CBF following GM602 Administration

| Compound (Group) | CBF during ischemia | CBF after drug administration | Post ischemia pre vs post drug adm. | GM602 gp vs vehicle |
|---|---|---|---|---|
| 1 - Vehicle (saline admin.) | 16.80 ± 2.53 | 17.90 ± 2.767 | p = 0.37 | NA |
| 2 - GM602 (2.5 mg/kg) | 16.50 ± 2.99 | 24.10 ± 2.424 | p < 0.0001 | p < 0.0001 |
| 3 - GM602 (10 mg/kg) | 14.40 ± 3.20 | 25.40 ± 2.459 | p < 0.0001 | p < 0.0001 |
| 4 - GM602 (20 mg/kg) | 16.20 ± 2.49 | 29.50 ± 3.923 | p < 0.0001 | P < 0.0001 |

Behavioral Measurements. Animals were assessed for neurological deficits based on several different parameters, which are indicated below. Animals treated with GM602 showed a dose dependent decrease in neurological deficits (data also shown in FIG. 39).

TABLE 27

Forelimb placing test following GM602 Administration

| Compound (Group) | Test Score | P value compare to vehicle |
|---|---|---|
| 1 - Vehicle | 14.40 ± 2.119 | NA |
| 2 - GM602 (2.5 mg/kg) | 11.10 ± 2.514 | p < 0. |
| 3 - GM602 (10 mg/kg) | 7.800 ± 2.466 | p < 0.0001 |
| 4 - GM602 (20 mg/kg) | 6.300 ± 2.003 | P < 0.0001 |

TABLE 28

Hindlimb placing test following GM602 Administration

| Compound (Group) | Test Score | P value compare to vehicle |
|---|---|---|
| 1 - Vehicle | 5.1 ± 0.74 | NA |
| 2 - GM602 (2.5 mg/kg) | 3.9 ± 1.20 | p < 0.02 |
| 3 - GM602 (10 mg/kg) | 2.7 ± 0.95 | p < 0.0001 |
| 4 - GM602 (20 mg/kg) | 2.0 ± 0.82 | P < 0.0001 |

TABLE 29

Balance Beam test following GM602 Administration

| Compound (Group) | Test Score | P value compare to vehicle |
|---|---|---|
| 1 - Vehicle | 5.300 ± 1.059 | NA |
| 2 - GM602 (2.5 mg/kg) | 4.100 ± 0.9944 | p < 0.0177 |
| 3 - GM602 (10 mg/kg) | 3.200 ± 0.7888 | p < 0.0001 |
| 4 - GM602 (20 mg/kg) | 2.700 ± 0.4930 | P < 0.0001 |

TABLE 30

Spontaneous activity following GM602 Administration

| Compound (Group) | Test Score | P value compare to vehicle |
|---|---|---|
| 1 - Vehicle | 0.2 ± 0.42 | NA |
| 2 - GM602 (2.5 mg/kg) | 0.9 ± 0.74 | p < 0.02 |
| 3 - GM602 (10 mg/kg) | 1.6 ± 0.52 | p < 0.0001 |
| 4 - GM602 (20 mg/kg) | 1.9 ± 0.74 | P < 0.0001 |

Biomarker Analysis. Tissue sections were collected for biomarker analysis (Fluoro-Jade and TNF).

Figure 41:
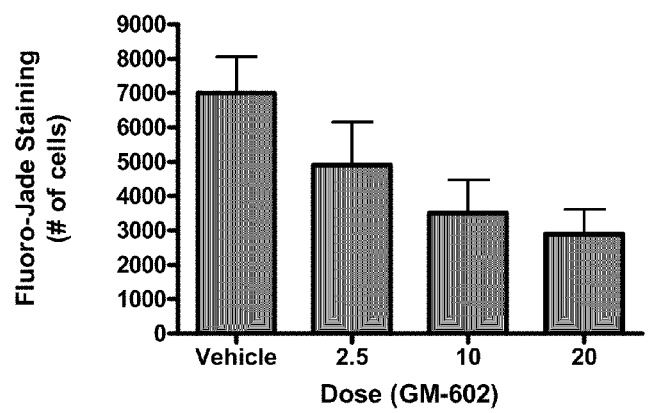
FIG. 41. Biomarker measurements in rats subject to ischemic injury. All rats were subjected to permanent cerebral ischemia followed by 28 days of recovery. At 3 hours after ischemia onset, animals were injected with vehicle (control), GM602 at 2.5, 10 or 20 mg/kg intravenously. Animals were sacrificed on day 28 and brain sections were processed for Fluoro-jade immunohistochemical analysis.

There was significant reduction in TNF staining seen in the tissue sections at 28 days in GM602 administered groups in a dose dependent manner. (Table 31 and FIG. 8). There was significant reduction in staining for Fluoro-Jade seen at 28 days following GM602 administration after permanent ischemic injury (Table 32 and FIG. 41).

TABLE 31

Decrease in TNF levels following GM602 Administration

| Compound (Group) | TNF levels (% of control) | P value compare to vehicle |
| --- | --- | --- |
| 1 - Vehicle | 89.07 ± 17.96 | NA |
| 2 - GM602 (2.5 mg/kg) | 64.24 ± 16.18 | P < 0.005 |
| 3 - GM602 (10 mg/kg) | 49.03 ± 12.60 | P < 0.0001 |
| 4 - GM602 (20 mg/kg) | 32.72 ± 11.15 | P < 0.0001 |

TABLE 32

Decrease in Fluoro-jade levels following GM602 Administration

| Compound (Group) | Fluoro-jade (# of cells) | P value compare to vehicle |
| --- | --- | --- |
| 1 - Vehicle | 7007 ± 1054 | NA |
| 2 - GM602 (2.5 mg/kg) | 4899 ± 1248 | p = 0.0007 |
| 3 - GM602 (10 mg/kg) | 3504 ± 959.4 | p < 0.0001 |
| 4 - GM602 (20 mg/kg) | 2889 ± 719.6 | p < 0.0001 |

Stroke is the third most common cause of death and the main cause of disability in the United States. The outcome and infarction size after focal cerebral ischemia is determined by both "necrotic" (paraptosis) cell death and by delayed neuronal cell loss in the borderzone of ischemia (programmed cell death or apoptosis). Recent therapies have emerged to treat ischemic stroke. However, these treatments mostly dealt with dissolving the blood clot but did not address neuroprotection, reduction of behavioral deficit or brain infarct volume once the neuronal cell death cycle has been triggered. Understanding the basic mechanisms that influence cell loss will help in the design of drugs and applications to reduce cell death associated with ischemic injury.

MNTF is a trophic factor that may provide protection from neurological diseases and allow for regeneration of neuronal tissue following injury or ischemic stroke. The studies performed here demonstrate the ability of GM602, the 6-amino acid analog of MNTF, to protect the brain from the detrimental effects of permanent cerebral ischemic injury in the rat in an effective and efficient way. Intravenous administration of GM602 at 2.5, 10 or 20 mg/kg at 3 hours following ischemic injury demonstrated a dose dependent protective effect in the brain against ischemic injury by a decrease in infarct volume, improved behavioral attributes, an increase in cerebral blood flow and decrease in inflammation and neuron degeneration. These studies suggest that GM602 may have a beneficial effect in permanent stroke.

When administered intravenously, GM602 was found to be neuroprotective against ischemic injury in the rat.

All patents, publications, scientific articles, web sites, and other documents and materials referenced or mentioned herein are indicative of the levels of skill of those skilled in the art to which this disclosure pertains, and each such referenced document and material is hereby incorporated by reference to the same extent as if it had been incorporated by reference in its entirety individually or set forth herein in its entirety. Applicants reserve the night to physically incorporate into this specification any and all materials and information from any such patents, publications, scientific articles, web sites, electronically available information, and other referenced materials or documents.

The specific methods and compositions described herein are representative of some embodiments and are exemplary and not intended as limitations on the scope of the appended claims. Other objects, aspects, and embodiments will occur to those skilled in the art upon consideration of this specification, and are encompassed within the spirit of the disclosure as defined by the scope of the claims. It will be readily apparent to one skilled in the art that varying substitutions and modifications may be made to the technology disclosed herein without departing from its scope and spirit. The technology illustratively described herein suitably may be practiced in the absence of any element or elements, or limitation or limitations, which is not specifically disclosed herein as essential. Thus, for example, in each instance herein, in embodiments or examples of the present technology, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the technology as claimed. Thus, it will be understood that although the present technology has been specifically disclosed by certain embodiments and optional features, modification and variation of the concepts herein disclosed may be resorted to by those skilled in the art, and that such modifications and variations are considered to be within the scope of the invention defined by the appended claims.

The technology has been described broadly and generically herein. Each of the narrower species and subgeneric groupings falling within the generic disclosure also form part of the disclosure. This includes the generic description of the technology with a proviso or negative limitation removing any subject matter from the genus, regardless of whether or not the excised material is specifically recited herein.

Other embodiments are within the following claims. In addition, where features or aspects of the technology are described in terms of Markush groups, those skilled in the art will recognize that the technology is also thereby described in terms of any individual member or subgroup of members of the Markush group.

What is claimed is:

1. A method of alleviating cerebral ischemia or a stroke in a mammal afflicted with the disorder, the method comprising administering to the mammal a motoneuronotropic factor (MNTF) analog having an amino acid sequence according to SEQ. ID NO:2 and which is capable of effectively and efficiently crossing the blood brain barrier, wherein a dosage for intravenous administration of MNTF analog is selected and the MNTF analog is administered intravenously to said mammal to result in a desired physiological outcome selected from a decrease cerebral infarct volume, ii) an increase in cerebral blood flow, iii) as reduced neurological deficit, or iv) a reduction in neural degeneration or inflammation in cerebral tissue of said mammal.

2. A method of reducing a cerebral infarct in a mammal afflicted with cerebral ischemia or a stroke, the method comprising i) selecting a dosage for intravenous administration of a motoneuronotropic factor (MNTF) analog haying an amino acid sequence according to SEQ ID NO:2 and which is capable of effectively and efficiently crossing the blood brain barrier, and ii) administering said MNTF analog intravenously according to step i) wherein there is a dose dependent decrease in cerebral infarct volume in said mammal afflicted with cerebral ischemia or a stroke.

3. A method of improving cerebral blood flow in a mammal afflicted with a neurological disorder, the method comprising i) selecting a dosage suitable for intravenous administration of a motoneuronotropic factor (MNTF) analog having an amino acid sequence according to SEQ ID NO:2 and which is capable of effectively and efficiently crossing the blood brain barrier, and ii) administering said MNTF intravenously according to step i) in a manner effective to increase cerebral blood, flow in said mammal.

4. A method of reducing a neurological deficit in a mammal afflicted with cerebral ischemia or a stroke, the method comprising ii selecting a dosage for intraveneous administration of a motoneuronotropic factor (MNTF) analog having an amino acid sequence according to SEQ ID NO:2 and which capable of effectively and efficiently crossing the blood brain barrier, and ii) administering said MNTF intravenously according to step i) in a manner effective to prevent or reduce a neurological deficit.

5. A method of reducing neural degeneration or inflammation in a mammal afflicted with cerebral ischemia or a stroke, the method comprising i) selecting a dosage suitable for intravenous administration of a motoneuronotropic factor (MNTF) analog haying an amino acid sequence according to SEQ ID NO:2 and which is capable of effectively and efficiently crossing the blood brain barrier, and ii administering said MNTF intravenously according to step i) in a manner effective to reduce neural degeneration or inflammation in cerebral tissue in the mammal.

6. A method according to claim 1, wherein the mammal is a human.

7. A method according to claim 1, wherein the MNTF analog dose is administered within 48 hours from the onset of ischemia.

8. A method according to claim 1, wherein the analog dose is administered within about 3, 6, or 12 hours from the onset of ischemia.

9. A method according to claim 1, wherein the MNTF dose is administered daily.

10. A method according to claim 1, wherein the MNTF analog is administered intravenously at a dosage of from 1 mg/kg to 10 mg/kg of body weight.

11. A method according to claim 10, wherein the intravenous dose of MNTF is administered within about 3, 6, or 12 hours from the onset of ischemia.

12. A method according to claim 10, wherein the mammal is a hum aft and the MNTF dosage is converted to human equivalent dosing.

13. A method according to claim 1, wherein said cerebral ischemia is characterized by acute or progressive loss of functional neural tissues.

14. A method according to claim 1, wherein said cerebral ischemia is associated with an immune or inflammatory response to an initial injury to nerve tissue, a trauma to nerve tissue, an autoimmune dysfunction, a neoplastic lesion, an infection, a chemical or mechanical trauma, a disease, an interruption of blood flow to the neurons or glial cells, a hypoxia, a brain tumor, or by other trauma to the nerve or surrounding material.

15. A method according to claim 1, wherein said motoneuronotropic factor (MNTF) analog acts as a neuroprotective for said cerebral ischemia.

16. A method according to claim 1, wherein said motoneuronotropic factor (MNTF) analog acts to protect the brain from acute ischemia and reperfusion injury.

17. A method according to claim 1, wherein the mammal is a human and the MNTF dosage is converted to human equivalent dosing.

18. A method according to claim 1, wherein the method is performed in conjunction with another therapy or MNTF is administered in combination with another therapeutic agent.

19. A method according to claim 1, wherein the MNTF analog is administered intravenously at a dosage of from 1 mg/kg 5 mg/kg of body weight.

20. A method according to claim 1, wherein the MNTF analog is administered intravenously at a dosage of from 1 mg/kg to 20 mg/kg of body weight.

21. A method according to claim 1, wherein the MNTF analog dose is administered within 18 or 24 hours from the onset of ischemia.

* * * * *

SEQUENCE LISTING

```
<160> NUMBER OF SEQ ID NOS: 142

<210> SEQ ID NO 1
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 1

Leu Gly Thr Phe Trp Gly Asp Thr Leu Asn Cys Trp Met Leu Ser Ala
1               5                   10                  15

Phe Ser Arg Tyr Ala Arg Cys Leu Ala Glu Gly His Asp Gly Pro Thr
            20                  25                  30

Gln

<210> SEQ ID NO 2
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 2

Phe Ser Arg Tyr Ala Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 3

Trp Met Leu Ser Ala Phe Ser
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 4

Met Leu Ser Ala Phe Ser Arg Tyr Ala Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 5

Phe Ser Arg Tyr Ala Arg Cys Leu Ala Glu Gly
1               5                   10

<210> SEQ ID NO 6
<211> LENGTH: 13
<212> TYPE: PRT
<213> ORGANISM: Artificial Sequence
<220> FEATURE:
```

-continued

<223> OTHER INFORMATION: Synthetic Sequence

<400> SEQUENCE: 6

Cys Trp Met Leu Ser Ala Phe Ser Arg Tyr Ala Arg Cys
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 7

Met Leu Ser Ala Phe Ser Arg Tyr Ala Arg Cys Leu Ala Glu Gly His
1               5                   10                  15

Asp Gly Pro Thr Gln
            20

<210> SEQ ID NO 8
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 8

Met Leu Ser Ala Phe Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 9

Leu Ser Ala Phe Ser Arg Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 10

Ser Ala Phe Ser Arg Tyr Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 11

Ala Phe Ser Arg Tyr Ala Arg
1               5

<210> SEQ ID NO 12
<211> LENGTH: 7
<212> TYPE: PRT
<213> ORGANISM: Artificial Sequence

```
<220> FEATURE:
<223> OTHER INFORMATION: Synthetic Sequence

<400> SEQUENCE: 12

Phe Ser Arg Tyr Ala Arg Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 13

Cys Trp Met Leu Ser Ala Phe Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 14

Trp Met Leu Ser Ala Phe Ser Arg
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 15

Met Leu Ser Ala Phe Ser Arg Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 16

Leu Ser Ala Phe Ser Arg Tyr Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 17

Ser Ala Phe Ser Arg Tyr Ala Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Sequence
```

```
<400> SEQUENCE: 18

Ala Phe Ser Arg Tyr Ala Arg Cys
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 19

Phe Ser Arg Tyr Ala Arg Cys Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 20

Asn Cys Trp Met Leu Ser Ala Phe Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 21

Cys Trp Met Leu Ser Ala Phe Ser Arg
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 22

Trp Met Leu Ser Ala Phe Ser Arg Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 23

Met Leu Ser Ala Phe Ser Arg Tyr Ala
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 24
```

```
Leu Ser Ala Phe Ser Arg Tyr Ala Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 25

Ser Ala Phe Ser Arg Tyr Ala Arg Cys
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 26

Ala Phe Ser Arg Tyr Ala Arg Cys Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 27

Phe Ser Arg Tyr Ala Arg Cys Leu Ala
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 28

Leu Asn Cys Trp Met Leu Ser Ala Phe Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 29

Asn Cys Trp Met Leu Ser Ala Phe Ser Arg
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 30

Cys Trp Met Leu Ser Ala Phe Ser Arg Tyr
```

```
<210> SEQ ID NO 31
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 31

Trp Met Leu Ser Ala Phe Ser Arg Tyr Ala
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 32

Leu Ser Ala Phe Ser Arg Tyr Ala Arg Cys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 33

Ser Ala Phe Ser Arg Tyr Ala Arg Cys Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 34

Ala Phe Ser Arg Tyr Ala Arg Cys Leu Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 35

Phe Ser Arg Tyr Ala Arg Cys Leu Ala Glu
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 36

Thr Leu Asn Cys Trp Met Leu Ser Ala Phe Ser
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 37

```
Leu Asn Cys Trp Met Leu Ser Ala Phe Ser Arg
1               5                   10
```

<210> SEQ ID NO 38
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 38

```
Asn Cys Trp Met Leu Ser Ala Phe Ser Arg Tyr
1               5                   10
```

<210> SEQ ID NO 39
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 39

```
Cys Trp Met Leu Ser Ala Phe Ser Arg Tyr Ala
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 40

```
Trp Met Leu Ser Ala Phe Ser Arg Tyr Ala Arg
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 41

```
Met Leu Ser Ala Phe Ser Arg Tyr Ala Arg Cys
1               5                   10
```

<210> SEQ ID NO 42
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 42

```
Leu Ser Ala Phe Ser Arg Tyr Ala Arg Cys Leu
1               5                   10
```

<210> SEQ ID NO 43

```
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 43

Ser Ala Phe Ser Arg Tyr Ala Arg Cys Leu Ala
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 44

Ala Phe Ser Arg Tyr Ala Arg Cys Leu Ala Glu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 45

Asp Thr Leu Asn Cys Trp Met Leu Ser Ala Phe Ser
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 46

Thr Leu Asn Cys Trp Met Leu Ser Ala Phe Ser Arg
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 47

Leu Asn Cys Trp Met Leu Ser Ala Phe Ser Arg Tyr
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 48

Asn Cys Trp Met Leu Ser Ala Phe Ser Arg Tyr Ala
1               5                   10

<210> SEQ ID NO 49
<211> LENGTH: 12
<212> TYPE: PRT
```

```
<213> ORGANISM: Artificial Sequence
<220> FEATURE:
<223> OTHER INFORMATION: Synthetic Sequence

<400> SEQUENCE: 49

Cys Trp Met Leu Ser Ala Phe Ser Arg Tyr Ala Arg
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 50

Trp Met Leu Ser Ala Phe Ser Arg Tyr Ala Arg Cys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 51

Met Leu Ser Ala Phe Ser Arg Tyr Ala Arg Cys Leu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 52

Leu Ser Ala Phe Ser Arg Tyr Ala Arg Cys Leu Ala
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 53

Ser Ala Phe Ser Arg Tyr Ala Arg Cys Leu Ala Glu
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 54

Ala Phe Ser Arg Tyr Ala Arg Cys Leu Ala Glu Gly
1               5                   10

<210> SEQ ID NO 55
<211> LENGTH: 12
<212> TYPE: PRT
<213> ORGANISM: Artificial Sequence
<220> FEATURE:
```

<223> OTHER INFORMATION: Synthetic Sequence

<400> SEQUENCE: 55

Phe Ser Arg Tyr Ala Arg Cys Leu Ala Glu Gly His
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 56

Gly Asp Thr Leu Asn Cys Trp Met Leu Ser Ala Phe Ser
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 57

Asp Thr Leu Asn Cys Trp Met Leu Ser Ala Phe Ser Arg
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 58

Thr Leu Asn Cys Trp Met Leu Ser Ala Phe Ser Arg Tyr
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 59

Leu Asn Cys Trp Met Leu Ser Ala Phe Ser Arg Tyr Ala
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 60

Asn Cys Trp Met Leu Ser Ala Phe Ser Arg Tyr Ala Arg
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic Sequence

```
<400> SEQUENCE: 61

Trp Met Leu Ser Ala Phe Ser Arg Tyr Ala Arg Cys Leu
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 62

Met Leu Ser Ala Phe Ser Arg Tyr Ala Arg Cys Leu Ala
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 63

Met Leu Ser Ala Phe Ser Arg Tyr Ala Arg Cys Leu Ala Glu
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 64

Leu Ser Ala Phe Ser Arg Tyr Ala Arg Cys Leu Ala Glu Gly
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 65

Ser Ala Phe Ser Arg Tyr Ala Arg Cys Leu Ala Glu Gly His
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 66

Ala Phe Ser Arg Tyr Ala Arg Cys Leu Ala Glu Gly His Asp
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 67
```

-continued

```
Phe Ser Arg Tyr Ala Arg Cys Leu Ala Glu Gly His Asp Gly
1               5                   10
```

<210> SEQ ID NO 68
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 68

```
Trp Gly Asp Thr Leu Asn Cys Trp Met Leu Ser Ala Phe Ser
1               5                   10
```

<210> SEQ ID NO 69
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 69

```
Gly Asp Thr Leu Asn Cys Trp Met Leu Ser Ala Phe Ser Arg
1               5                   10
```

<210> SEQ ID NO 70
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 70

```
Asp Thr Leu Asn Cys Trp Met Leu Ser Ala Phe Ser Arg Tyr
1               5                   10
```

<210> SEQ ID NO 71
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 71

```
Thr Leu Asn Cys Trp Met Leu Ser Ala Phe Ser Arg Tyr Ala
1               5                   10
```

<210> SEQ ID NO 72
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 72

```
Leu Asn Cys Trp Met Leu Ser Ala Phe Ser Arg Tyr Ala Arg
1               5                   10
```

<210> SEQ ID NO 73
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 73

```
Asn Cys Trp Met Leu Ser Ala Phe Ser Arg Tyr Ala Arg Cys
1               5                   10
```

```
<210> SEQ ID NO 74
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 74

Cys Trp Met Leu Ser Ala Phe Ser Arg Tyr Ala Arg Cys Leu
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 75

Trp Met Leu Ser Ala Phe Ser Arg Tyr Ala Arg Cys Leu Ala
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 76

Met Leu Ser Ala Phe Ser Arg Tyr Ala Arg Cys Leu Ala Glu
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 77

Leu Ser Ala Phe Ser Arg Tyr Ala Arg Cys Leu Ala Glu Gly
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 78

Ser Ala Phe Ser Arg Tyr Ala Arg Cys Leu Ala Glu Gly His
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 79

Ala Phe Ser Arg Tyr Ala Arg Cys Leu Ala Glu Gly His Asp
1               5                   10
```

```
<210> SEQ ID NO 80
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 80

Phe Ser Arg Tyr Ala Arg Cys Leu Ala Glu Gly His Asp Gly
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 81

Phe Trp Gly Asp Thr Leu Asn Cys Trp Met Leu Ser Ala Phe Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 82

Trp Gly Asp Thr Leu Asn Cys Trp Met Leu Ser Ala Phe Ser Arg
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 83

Gly Asp Thr Leu Asn Cys Trp Met Leu Ser Ala Phe Ser Arg Tyr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 84

Asp Thr Leu Asn Cys Trp Met Leu Ser Ala Phe Ser Arg Tyr Ala
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 85

Thr Leu Asn Cys Trp Met Leu Ser Ala Phe Ser Arg Tyr Ala Arg
1               5                   10                  15

<210> SEQ ID NO 86
<211> LENGTH: 15
```

```
<212> TYPE: PRT
<213> ORGANISM: Artificial Sequence
<220> FEATURE:
<223> OTHER INFORMATION: Synthetic Sequence

<400> SEQUENCE: 86

Leu Asn Cys Trp Met Leu Ser Ala Phe Ser Arg Tyr Ala Arg Cys
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 87

Asn Cys Trp Met Leu Ser Ala Phe Ser Arg Tyr Ala Arg Cys Leu
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 88

Cys Trp Met Leu Ser Ala Phe Ser Arg Tyr Ala Arg Cys Leu Ala
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 89

Trp Met Leu Ser Ala Phe Ser Arg Tyr Ala Arg Cys Leu Ala Glu
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 90

Met Leu Ser Ala Phe Ser Arg Tyr Ala Arg Cys Leu Ala Glu Gly
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 91

Leu Ser Ala Phe Ser Arg Tyr Ala Arg Cys Leu Ala Glu Gly His
1               5                   10                  15

<210> SEQ ID NO 92
<211> LENGTH: 15
<212> TYPE: PRT
<213> ORGANISM: Artificial Sequence
```

```
<220> FEATURE:
<223> OTHER INFORMATION: Synthetic Sequence

<400> SEQUENCE: 92

Ser Ala Phe Ser Arg Tyr Ala Arg Cys Leu Ala Glu Gly His Asp
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 93

Ala Phe Ser Arg Tyr Ala Arg Cys Leu Ala Glu Gly His Asp Gly
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 94

Phe Ser Arg Tyr Ala Arg Cys Leu Ala Glu Gly His Asp Gly Pro
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 95

Thr Phe Trp Gly Asp Thr Leu Asn Cys Trp Met Leu Ser Ala Phe Ser
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 96

Phe Trp Gly Asp Thr Leu Asn Cys Trp Met Leu Ser Ala Phe Ser Arg
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 97

Trp Gly Asp Thr Leu Asn Cys Trp Met Leu Ser Ala Phe Ser Arg Tyr
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Synthetic Sequence
```

<400> SEQUENCE: 98

Gly Asp Thr Leu Asn Cys Trp Met Leu Ser Ala Phe Ser Arg Tyr Ala
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 99

Asp Thr Leu Asn Cys Trp Met Leu Ser Ala Phe Ser Arg Tyr Ala Arg
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 100

Thr Leu Asn Cys Trp Met Leu Ser Ala Phe Ser Arg Tyr Ala Arg Cys
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 101

Leu Asn Cys Trp Met Leu Ser Ala Phe Ser Arg Tyr Ala Arg Cys Leu
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 102

Asn Cys Trp Met Leu Ser Ala Phe Ser Arg Tyr Ala Arg Cys Leu Ala
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 103

Cys Trp Met Leu Ser Ala Phe Ser Arg Tyr Ala Arg Cys Leu Ala Glu
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 104

Trp Met Leu Ser Ala Phe Ser Arg Tyr Ala Arg Cys Leu Ala Glu Gly
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 105

Met Leu Ser Ala Phe Ser Arg Tyr Ala Arg Cys Leu Ala Glu Gly His
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 106

Leu Ser Ala Phe Ser Arg Tyr Ala Arg Cys Leu Ala Glu Gly His Asp
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 107

Ser Ala Phe Ser Arg Tyr Ala Arg Cys Leu Ala Glu Gly His Asp Gly
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 108

Ala Phe Ser Arg Tyr Ala Arg Cys Leu Ala Glu Gly His Asp Gly Pro
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 109

Phe Ser Arg Tyr Ala Arg Cys Leu Ala Glu Gly His Asp Gly Pro Thr
1               5                   10                  15

<210> SEQ ID NO 110
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 110

Gly Thr Phe Trp Gly Asp Thr Leu Asn Cys Trp Met Leu Ser Ala Phe

```
1               5                   10                  15
Ser

<210> SEQ ID NO 111
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 111

Thr Phe Trp Gly Asp Thr Leu Asn Cys Trp Met Leu Ser Ala Phe Ser
1               5                   10                  15
Arg

<210> SEQ ID NO 112
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 112

Phe Trp Gly Asp Thr Leu Asn Cys Trp Met Leu Ser Ala Phe Ser Arg
1               5                   10                  15
Tyr

<210> SEQ ID NO 113
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 113

Trp Gly Asp Thr Leu Asn Cys Trp Met Leu Ser Ala Phe Ser Arg Tyr
1               5                   10                  15
Ala

<210> SEQ ID NO 114
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 114

Gly Asp Thr Leu Asn Cys Trp Met Leu Ser Ala Phe Ser Arg Tyr Ala
1               5                   10                  15
Arg

<210> SEQ ID NO 115
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 115

Asp Thr Leu Asn Cys Trp Met Leu Ser Ala Phe Ser Arg Tyr Ala Arg
1               5                   10                  15
Cys
```

```
<210> SEQ ID NO 116
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 116

Thr Leu Asn Cys Trp Met Leu Ser Ala Phe Ser Arg Tyr Ala Arg Cys
 1               5                  10                  15
Leu

<210> SEQ ID NO 117
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 117

Leu Asn Cys Trp Met Leu Ser Ala Phe Ser Arg Tyr Ala Arg Cys Leu
 1               5                  10                  15
Ala

<210> SEQ ID NO 118
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 118

Asn Cys Trp Met Leu Ser Ala Phe Ser Arg Tyr Ala Arg Cys Leu Ala
 1               5                  10                  15
Glu

<210> SEQ ID NO 119
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 119

Cys Trp Met Leu Ser Ala Phe Ser Arg Tyr Ala Arg Cys Leu Ala Glu
 1               5                  10                  15
Gly

<210> SEQ ID NO 120
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 120

Trp Met Leu Ser Ala Phe Ser Arg Tyr Ala Arg Cys Leu Ala Glu Gly
 1               5                  10                  15
His

<210> SEQ ID NO 121
<211> LENGTH: 17
<212> TYPE: PRT
<213> ORGANISM: Artificial Sequence
<220> FEATURE:
```

<223> OTHER INFORMATION: Synthetic Sequence

<400> SEQUENCE: 121

Met Leu Ser Ala Phe Ser Arg Tyr Ala Arg Cys Leu Ala Glu Gly His
1               5                   10                  15

Asp

<210> SEQ ID NO 122
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 122

Leu Ser Ala Phe Ser Arg Tyr Ala Arg Cys Leu Ala Glu Gly His Asp
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 123

Ser Ala Phe Ser Arg Tyr Ala Arg Cys Leu Ala Glu Gly His Asp Gly
1               5                   10                  15

Pro

<210> SEQ ID NO 124
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 124

Ala Phe Ser Arg Tyr Ala Arg Cys Leu Ala Glu Gly His Asp Gly Pro
1               5                   10                  15

Thr

<210> SEQ ID NO 125
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 125

Phe Ser Arg Tyr Ala Arg Cys Leu Ala Glu Gly His Asp Gly Pro Thr
1               5                   10                  15

Gln

<210> SEQ ID NO 126
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 126

Leu Gly Thr Phe Trp Gly Asp Thr Leu Asn Cys Trp Met Leu Ser Ala

```
                    1               5                  10                 15
Phe Ser

<210> SEQ ID NO 127
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 127

Gly Thr Phe Trp Gly Asp Thr Leu Asn Cys Trp Met Leu Ser Ala Phe
1               5                   10                  15

Ser Arg

<210> SEQ ID NO 128
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 128

Thr Phe Trp Gly Asp Thr Leu Asn Cys Trp Met Leu Ser Ala Phe Ser
1               5                   10                  15

Arg Tyr

<210> SEQ ID NO 129
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 129

Phe Trp Gly Asp Thr Leu Asn Cys Trp Met Leu Ser Ala Phe Ser Arg
1               5                   10                  15

Tyr Ala

<210> SEQ ID NO 130
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 130

Trp Gly Asp Thr Leu Asn Cys Trp Met Leu Ser Ala Phe Ser Arg Tyr
1               5                   10                  15

Ala Arg

<210> SEQ ID NO 131
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 131

Gly Asp Thr Leu Asn Cys Trp Met Leu Ser Ala Phe Ser Arg Tyr Ala
1               5                   10                  15

Arg Cys
```

```
<210> SEQ ID NO 132
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 132

Asp Thr Leu Asn Cys Trp Met Leu Ser Ala Phe Ser Arg Tyr Ala Arg
1               5                   10                  15

Cys Leu

<210> SEQ ID NO 133
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 133

Thr Leu Asn Cys Trp Met Leu Ser Ala Phe Ser Arg Tyr Ala Arg Cys
1               5                   10                  15

Leu Ala

<210> SEQ ID NO 134
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 134

Leu Asn Cys Trp Met Leu Ser Ala Phe Ser Arg Tyr Ala Arg Cys Leu
1               5                   10                  15

Ala Glu

<210> SEQ ID NO 135
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 135

Asn Cys Trp Met Leu Ser Ala Phe Ser Arg Tyr Ala Arg Cys Leu Ala
1               5                   10                  15

Glu Gly

<210> SEQ ID NO 136
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 136

Cys Trp Met Leu Ser Ala Phe Ser Arg Tyr Ala Arg Cys Leu Ala Glu
1               5                   10                  15

Gly His

<210> SEQ ID NO 137
<211> LENGTH: 18
<212> TYPE: PRT
<213> ORGANISM: Artificial Sequence
<220> FEATURE:
```

-continued

<223> OTHER INFORMATION: Synthetic Sequence

<400> SEQUENCE: 137

Trp Met Leu Ser Ala Phe Ser Arg Tyr Ala Arg Cys Leu Ala Glu Gly
1               5                   10                  15

His Asp

<210> SEQ ID NO 138
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 138

Met Leu Ser Ala Phe Ser Arg Tyr Ala Arg Cys Leu Ala Glu Gly His
1               5                   10                  15

Asp Gly

<210> SEQ ID NO 139
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 139

Leu Ser Ala Phe Ser Arg Tyr Ala Arg Cys Leu Ala Glu Gly His Asp
1               5                   10                  15

Gly Pro

<210> SEQ ID NO 140
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 140

Ser Ala Phe Ser Arg Tyr Ala Arg Cys Leu Ala Glu Gly His Asp Gly
1               5                   10                  15

Pro Thr

<210> SEQ ID NO 141
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 141

Ala Phe Ser Arg Tyr Ala Arg Cys Leu Ala Glu Gly His Asp Gly Pro
1               5                   10                  15

Thr Gln

<210> SEQ ID NO 142
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 142

Phe Ser Arg Tyr Ala Arg Cys Leu Ala Glu Gly His Asp Gly Pro Thr

-continued

```
1               5              10              15
Gln
```